(12) United States Patent
Rutkove et al.

(10) Patent No.: US 11,246,504 B2
(45) Date of Patent: Feb. 15, 2022

(54) ENHANCED MEASUREMENTS OF BIOIMPEDANCE

(71) Applicant: Myolex Inc., Brookline, MA (US)

(72) Inventors: Seward Rutkove, Brookline, MA (US); Elmer C Lupton, Charlestown, MA (US); Jose L. Bohorquez, Burlingame, CA (US); Haydn Taylor, Windham, NH (US); Gonzalo Cespedes, Daly City, CA (US); Cary Liberman, Oakland, CA (US); Dmitri Khrebtukov, San Francisco, CA (US); Claudio Cassina, Hollywood, FL (US); Yensy Hall, Pembroke Pines, FL (US); Stanislava Daraskevich, San Francisco, CA (US); Juan Jaramillo, San Francisco, CA (US)

(73) Assignee: Myolex Inc., Brookline, MA (US)

( * ) Notice: Subject to any disclaimer, the term of this patent is extended or adjusted under 35 U.S.C. 154(b) by 0 days.

(21) Appl. No.: 16/735,648

(22) Filed: Jan. 6, 2020

(65) Prior Publication Data

US 2020/0253503 A1    Aug. 13, 2020

Related U.S. Application Data

(63) Continuation of application No. 14/950,821, filed on Nov. 24, 2015, now abandoned, which is a
(Continued)

(51) Int. Cl.
*A61B 5/0537*    (2021.01)
*A61B 5/00*    (2006.01)

(52) U.S. Cl.
CPC .......... *A61B 5/0537* (2013.01); *A61B 5/4519* (2013.01); *A61B 5/4872* (2013.01);
(Continued)

(58) Field of Classification Search
CPC .......... A61B 2562/043; A61B 2562/02; A61B 2562/0214; A61B 2560/0431; A61B 2560/04; A61B 2560/0425; A61B 5/7425; A61B 5/742; A61B 5/7278; A61B 5/486; A61B 5/0004; A61B 5/4881;
(Continued)

(56) References Cited

U.S. PATENT DOCUMENTS 4,273,135 A * 6/1981 Larimore ........... A61B 5/04087
600/391
9,173,586 B2 * 11/2015 Deno .................. A61B 5/6886
(Continued)

FOREIGN PATENT DOCUMENTS

WO    WO-2011022068 A1 *  2/2011 ............. A61B 5/053

*Primary Examiner* — Matthew Kremer
*Assistant Examiner* — Avery M Foley
(74) *Attorney, Agent, or Firm* — Elmer C Lupton

(57) ABSTRACT

A portable device for measuring a bioimpedance-related property of tissue includes a plurality of electrodes arranged in a pattern on a surface and associated software for measuring bio-impedance related data of localized regions of tissue and calculate health-related parameters based on the measured data. These calculated parameters may be representative of muscular health of the localized tissue region.

20 Claims, 39 Drawing Sheets

Related U.S. Application Data continuation-in-part of application No. PCT/US2014/052563, filed on Aug. 25, 2014.

(60) Provisional application No. 62/083,866, filed on Nov. 24, 2014, provisional application No. 61/869,757, filed on Aug. 25, 2013, provisional application No. 61/916,635, filed on Dec. 16, 2013, provisional application No. 61/952,483, filed on Mar. 13, 2014, provisional application No. 61/012,192, filed on Dec. 7, 2007.

(52) U.S. Cl.
CPC ............ *A61B 5/0004* (2013.01); *A61B 5/486* (2013.01); *A61B 5/7278* (2013.01); *A61B 5/742* (2013.01); *A61B 2560/0425* (2013.01); *A61B 2562/0214* (2013.01); *A61B 2562/043* (2013.01)

(58) Field of Classification Search
CPC ... A61B 5/4878; A61B 5/4875; A61B 5/4869; A61B 5/4872; A61B 5/4538; A61B 5/4519; A61B 5/45; A61B 5/063; A61B 5/053; A61B 5/0531; A61B 5/0537
See application file for complete search history.

(56) References Cited

U.S. PATENT DOCUMENTS

| | | | |
|---|---|---|---|
| 2004/0054298 A1* | 3/2004 | Masuo | A61B 5/4872 600/547 |
| 2004/0059242 A1* | 3/2004 | Masuo | A61B 5/0537 600/547 |
| 2009/0201172 A1* | 8/2009 | Edell | A61B 5/0002 340/870.3 |
| 2012/0157802 A1* | 6/2012 | Chou | A61B 5/0404 600/324 |
| 2012/0245436 A1* | 9/2012 | Rutkove | A61B 5/053 600/301 |
| 2013/0150687 A1* | 6/2013 | Kato | A61B 5/14552 600/324 |
| 2013/0172775 A1* | 7/2013 | Ozawa | A61B 5/0537 600/547 |
| 2014/0070957 A1* | 3/2014 | Longinotti-Buitoni | G06F 3/011 340/870.01 |
| 2015/0109105 A1* | 4/2015 | Shimizu | A61B 5/1171 340/5.82 |

* cited by examiner

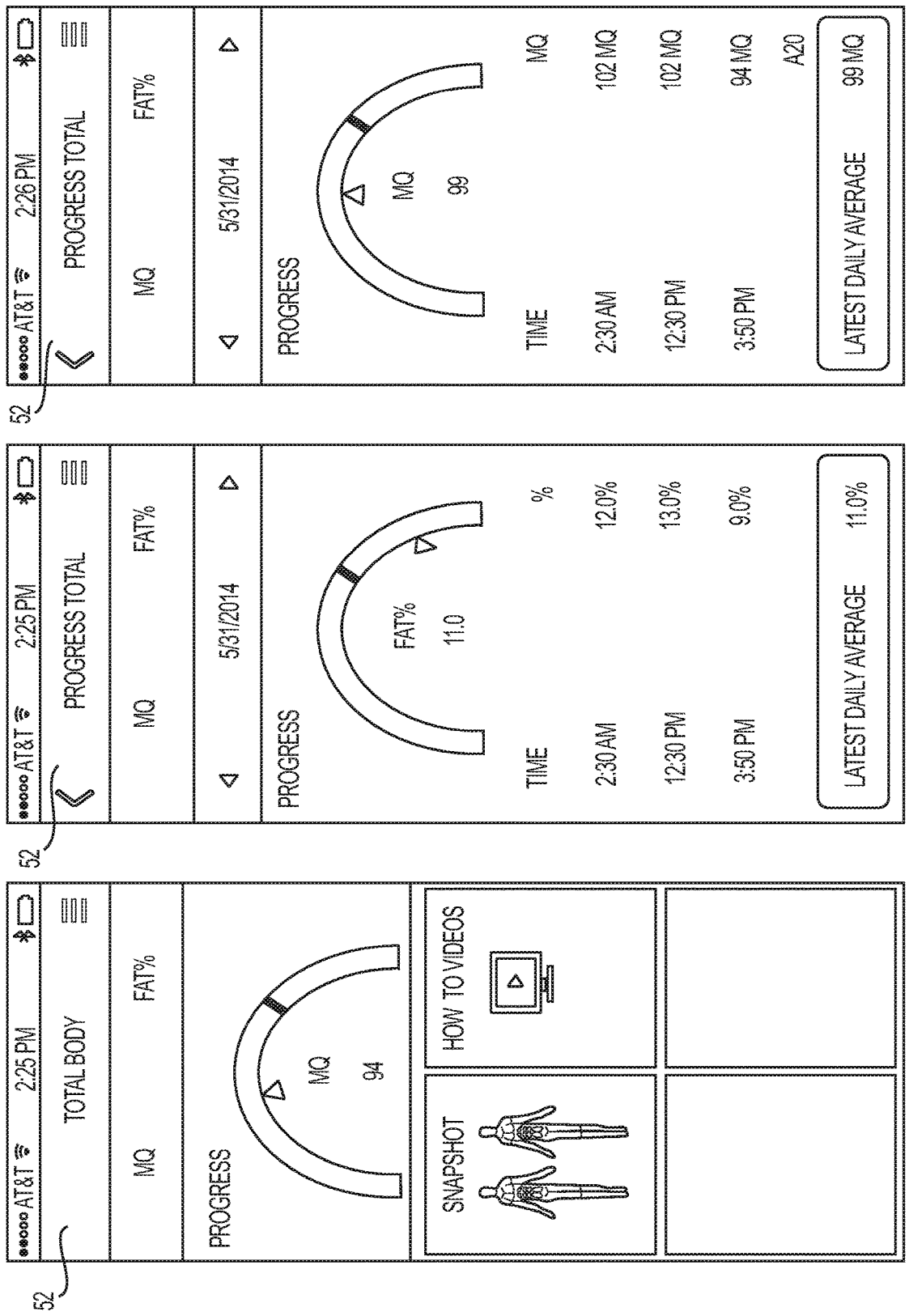

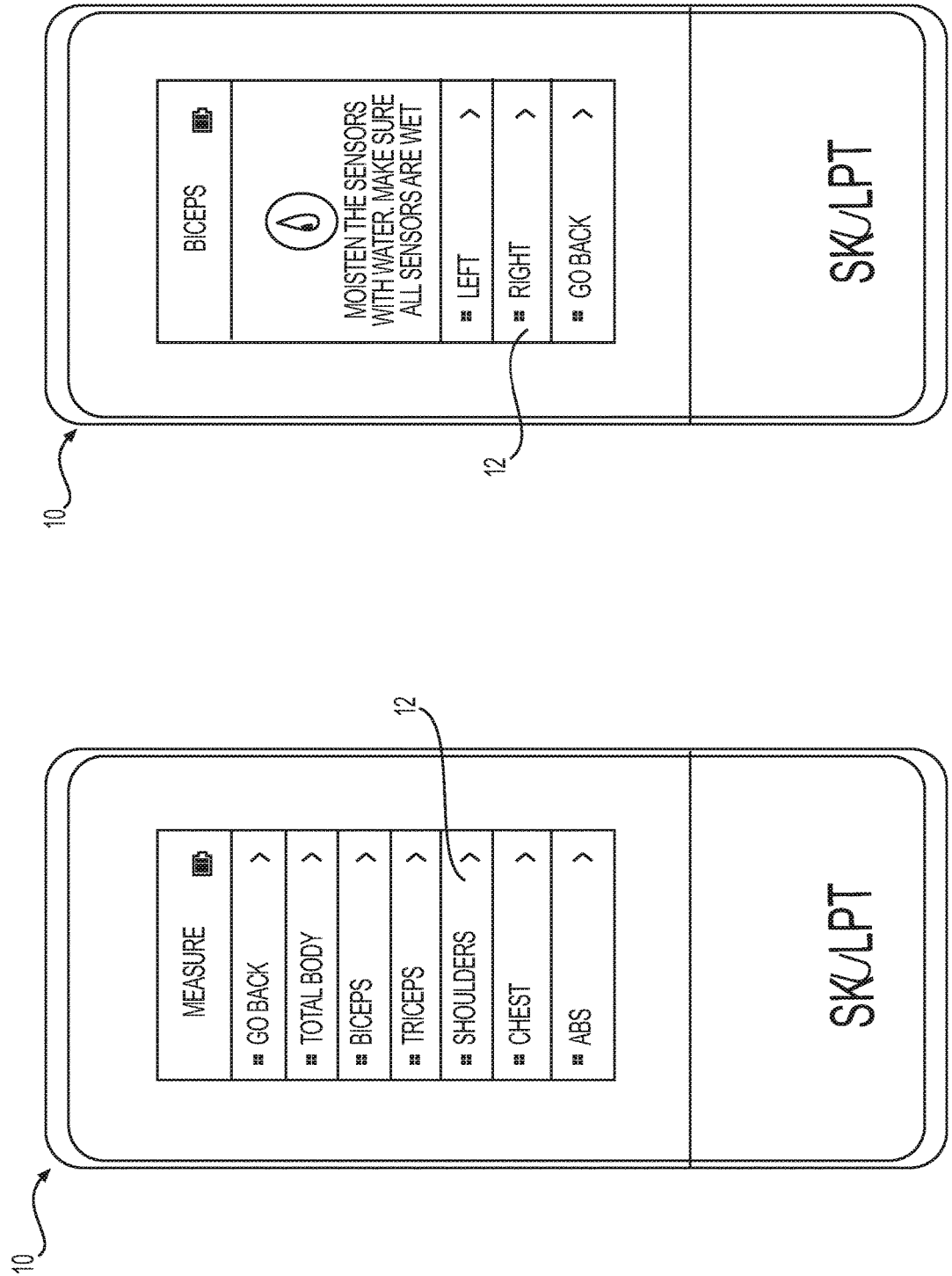

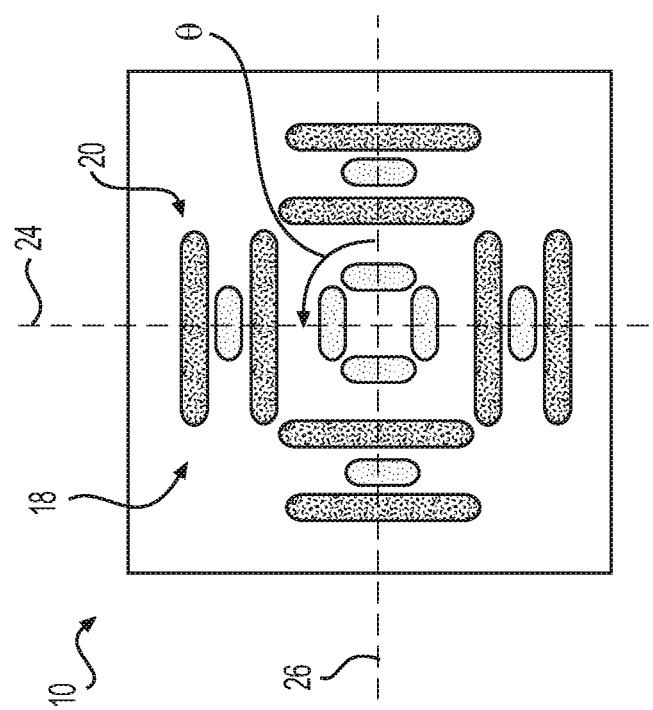
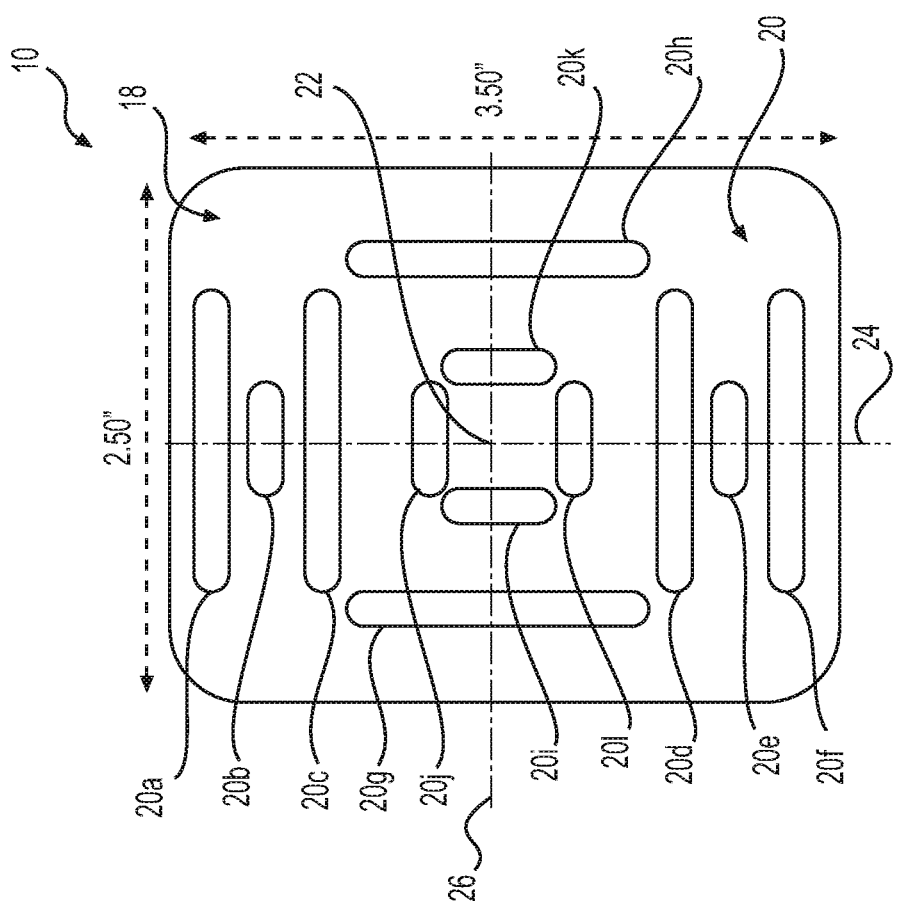
FIG. 10B
FIG. 10A

| TIME (MIN) | MQ  |
|------------|-----|
| 0          | 106 |
| 10         | 106 |
| 20         | 106 |
| 30         | 107 |
| 40         | 107 |
| 50         | 107 |
| 60         | 106 |
| 70         | 107 |
| 80         | 106 |
| 85         | 116 |
| 88         | 127 |
| 90         | 117 |
| 92         | 107 |
| 94         | 97  |
| 96         | 86  |
| 98         | 77  |
| 100        | 74  |
| 105        | 73  |
| 110        | 72  |
| 120        | 73  |
| 130        | 77  |
| 140        | 82  |
| 150        | 86  |
| 160        | 92  |
| 170        | 98  |
| 180        | 100 |
| 190        | 105 |
| 200        | 109 |
| 210        | 111 |
| 220        | 114 |
| 230        | 115 |
| 240        | 118 |
| 250        | 119 |
| 260        | 119 |
| 270        | 118 |
| 280        | 119 |
| 290        | 117 |
| 300        | 118 |
| 310        | 116 |
| 320        | 117 |
| 330        | 116 |
| 340        | 114 |
| 350        | 115 |
| 360        | 116 |
| 370        | 113 |
| 380        | 113 |
| 390        | 112 |
| 400        | 112 |
| 410        | 113 |
| 420        | 111 |
| 430        | 111 |
| 440        | 110 |
| 450        | 111 |
| 460        | 110 |
| 470        | 110 |
| 480        | 109 |
| 490        | 108 |
| 500        | 108 |
| 510        | 108 |
| 520        | 109 |
| 530        | 109 |
| 540        | 108 |
| 550        | 106 |
| 560        | 107 |
| 570        | 108 |
| 580        | 107 |
| 590        | 108 |
| 600        | 107 |
| 610        | 106 |
| 620        | 108 |
| 630        | 108 |
| 640        | 106 |
| 650        | 107 |
| 660        | 107 |
| 670        | 107 |
| 680        | 106 |
| 690        | 106 |
| 700        | 107 |
| 710        | 106 |
| 720        | 106 |
| 730        | 107 |
| 740        | 108 |
| 750        | 107 |
| 760        | 107 |
| 770        | 107 |

*FIG. 18*

| SUBJECT# | 1 | 2 | 3 | 4 | 5 | 6 | 7 | 8 | 9 | 10 |
|---|---|---|---|---|---|---|---|---|---|---|
| GENDER | M | M | M | M | M | F | F | F | F | F |
| WEIGHT (LBS) | 160 | 162 | 140 | 163 | 188 | 142 | 114 | 131 | 115 | 150 |
| MUSCLE MQ | | | | | | | | | | |
| TOTAL BODY | 144 | 140 | 139 | 132 | 125 | 110 | 96 | 90 | 88 | 87 |
| BICEPS | 128 | 131 | 126 | 125 | 126 | 113 | 103 | 95 | 93 | 92 |
| TRICEPS | 155 | 129 | 116 | 118 | 117 | 104 | 83 | 75 | 70 | 78 |
| ABS | 144 | 151 | 147 | 141 | 132 | 116 | 105 | 105 | 107 | 97 |
| QUADS | 148 | 149 | 148 | 143 | 124 | 101 | 89 | 88 | 82 | 81 |
| SHOULDER | 136 | 122 | 130 | 120 | 124 | 95 | 86 | 89 | 87 | 72 |
| FOREARM | 129 | 127 | 112 | 113 | 126 | 114 | 106 | 102 | 86 | 98 |
| CHEST | 135 | 144 | 137 | 139 | 136 | | | | | |
| UPPER BACK | 108 | 109 | 120 | 113 | 118 | 95 | 88 | 82 | 91 | 79 |
| LOWER BACK | 124 | 117 | 105 | 123 | 113 | 92 | 80 | 70 | 74 | 76 |
| HAMSTRINGS | 134 | 119 | 122 | 121 | 115 | 77 | 79 | 82 | 67 | 72 |
| CALVES | 115 | 113 | 113 | 106 | 96 | 63 | 73 | 78 | 67 | 88 |
| GLUTES | | | | | | | | 67 | | |
| SUBJECT# FAT PERCENT | 1 | 2 | 3 | 4 | 5 | 6 | 7 | 8 | 9 | 10 |
| TOTAL BODY | 8.8 | 7 | 11.8 | 7.6 | 9.8 | 16.9 | 26.9 | 27 | 23.3 | 29.2 |
| BICEPS | 10.7 | 10 | 10.9 | 9.5 | 9.9 | 13.5 | 19.7 | 20.2 | 18.4 | 20.8 |
| TRICEPS | 9.7 | 7.1 | 9.7 | 7.7 | 8.8 | 25 | 36.5 | 37.3 | 31.7 | 34.5 |
| ABS | 7.7 | 4.8 | 17.9 | 6.8 | 10.7 | 11.3 | 18.8 | 18.1 | 14.2 | 35.2 |
| QUADS | 7.1 | 6.1 | 6.8 | 6.4 | 9.9 | 17.5 | 31.5 | 31.5 | 28.9 | 35.2 |
| SHOULDER | 7 | 8.4 | 7.7 | 7.7 | 8.3 | 13.7 | 23.2 | 23.9 | 16.1 | 31 |
| FOREARM | 12.1 | 11.8 | 11.1 | 9.3 | 9.2 | 14.8 | 26.2 | 14 | 15.8 | 17.6 |
| CHEST | 8.4 | 5.6 | 6.6 | 7.1 | 6.3 | | | | | |
| UPPER BACK | 8.5 | 8.2 | 7.1 | 7.2 | 6.1 | 11.4 | 18.3 | 16.2 | 13.6 | 21.9 |
| LOWER BACK | 6.4 | | 7.9 | 6.2 | 7.4 | 11.4 | 16.9 | 25.6 | 16.1 | 19.2 |
| HAMSTRINGS | 9.2 | 6.6 | 7.8 | 7.4 | 8.5 | 17.4 | 23.9 | 19.5 | 24 | 27 |
| CALVES | 12.2 | 10.5 | 10.3 | 9.8 | 12.8 | 18.8 | 33 | 22 | 27.1 | 15.1 |
| GLUTES | | | | | | | | 39.8 | | |

*FIG. 19*

MEN

| NBICEPS | 38 |
|---|---|
| NCALVES | 43 |
| NCHEST | 44 |
| NHIP | 63 |
| NLOW BACK | 46 |
| NUPPER BACK | 46 |
| NTHIGH | 50 |
| NTRICEPS | 44 |
| NABS | 60 |

WOMEN

| NBICEPS | 38 |
|---|---|
| NCALVES | 43 |
| NCHEST | 44 |
| NHIP | 63 |
| NLOW BACK | 46 |
| NUPPER BACK | 46 |
| NTHIGH | 50 |
| NTRICEPS | 44 |
| NABS | 60 |

| SUBJECT# | 11 | 12 |
|---|---|---|
| GENDER | M | F |
| WEIGHT | 165.2 | 113 |
| MUSCLE MQ | | |
| BICEPS | 125 | 118 |
| CALF | 124 | 137 |
| CHEST | 142 | 161 |
| HIP | 127 | 107 |
| LOWER BACK | 130 | 126 |
| SCAPULA | 130 | 120 |
| THIGH | 134 | 124 |
| TRICEPS | 139 | 122 |
| WAIST | 105 | 129 |
| SUBJECT# FAT PERCENT | 11 | 12 |
| BICEPS | 12.7 | 18.8 |
| CALF | 11.8 | 12.5 |
| CHEST | 7.8 | 38.3 |
| HIP | 14.4 | 21.4 |
| LOWER BACK | 9.1 | 14.5 |
| SCAPULA | 9.1 | 14.5 |
| THIGH | 11.1 | 20.1 |
| TRICEPS | 9.9 | 22.6 |
| WAIST | 19.2 | 12.9 |

FIG. 20

ENHANCED MEASUREMENTS OF BIOIMPEDANCE

CROSS-REFERENCE TO RELATED APPLICATIONS

This application is a continuation of U.S. patent application Ser. No. 14/950,821 filed Nov. 24, 2015 published Jun. 9, 2016 as US Patent Publication 20160157749. U.S. patent application Ser. No. 14/950,821 claims the benefit of U.S. Provisional Application No. 62/083,866, filed Nov. 24, 2014, and also is a continuation-in-part of International Application No. PCT/US2014/052563, filed Aug. 25, 2014. International Application No. PCT/US2014/052563 claims priority to U.S. Provisional Patent Application Nos.: 61/869,757, filed on Aug. 25, 2013; 61/916,635, filed on Dec. 16, 2013; 61/952,483, filed on Mar. 13, 2014; and 62/012,192, filed on Jun. 13, 2014. The disclosures of all these applications and publications are incorporated by reference in their entirety herein.

GOVERNMENT LICENSE RIGHTS

This invention was made with U.S. Government support under grants R43NS073188, R43NS070385, R44NS070385, R44AR064142, and R41AG047021 awarded by the National Institutes of Health and 1064826 awarded by the National Science Foundation. The government has certain rights in the Invention.

FIELD OF THE DISCLOSURE

Embodiments of the present disclosure disclose systems and methods for measuring, tracking, and/or managing the health of individual body parts. In particular, the systems and devices of the present disclosure enable the measurement of health-related parameters in localized regions of a user's body.

BACKGROUND

The benefit of measuring electrical impedance of tissue as a method of assessing the health of the tissue is known. See for example: U.S. Pat. Nos. 8,892,198 and 9,113,808; and U.S. Patent Application Nos. 2010/0292603 and 2012/0245436, all of which are incorporated herein in their entirety by reference. These references discuss measurement of electrical impedance myography (EIM). Unlike standard electrophysiological approaches to measuring tissue health, EIM is less directly dependent upon inherent electrical potential of muscle or nerve tissue. EIM is based on electrical bioimpedance of tissue. It measures the effect of tissue structure and properties on the flow of extremely small, non-intrusive amounts of electrical current. Unlike standard bioimpedance approaches, using EIM, measurements can be performed over small areas of muscle. In EIM, electrical current, such as, e.g., high-frequency alternating current, may be applied to localized areas of muscle via electrodes (e.g., surface electrodes) and the consequent surface voltage patterns are analyzed.

Sustained exercise, including aerobic and anaerobic activities such as running, cycling, and weight lifting, can produce muscle fatigue. Following sustained exertion, a variety of physiological alterations occur in muscle, including the development of muscle edema (swelling), muscle fiber rupture, and hyperemia (increased blood flow). The degree and time course of recovery from these alterations depends on the type, duration, and intensity of the exercise performed. Recovery time can be short (e.g., a few minutes with minor exercise) or long (e.g., days or even weeks after sustained intense exercise) depending upon the intensity and duration of the exercise. Additionally, during the recovery phase, muscle will be at a reduced capacity. Over time, this exercise-injury-recovery cycle can actually lead to enhanced physiological condition of the muscle. However, in cases of excessive use, it can lead to overtraining and muscle injury. Other factors that can also impact recovery also include nutrition and overall health status. Thus, it may be desirable to perform EIM measurements during, or immediately after, exercise.

However, EIM measurement systems of the prior art are large and immobile, and require complex and fragile electronic equipment. Consequently, EIM measurements using such systems are relatively expensive and slow. The large size and complex circuitry of these prior art systems limit their use in EIM measurements of users who are mobile and/or engaged in exercise. The systems and methods of the present disclosure may alleviate some of the above-described deficiencies. The scope of the current disclosure, however, is defined by the attached claims, and not by its ability to solve a specific problem.

SUMMARY OF THE DISCLOSURE

The devices and methods of the current disclosure enable the calculation of health related parameters (e.g., parameters indicative of fat content, such as, e.g., fat percentage and muscle quality (MQ)) for a specific body region (e.g., arms, legs, and/or core) or muscle (e.g., biceps, abdominal muscle, etc.) by measuring the bioimpedance of that region of the body directly. Known bioimpedance measurement systems measure parameters related to global fat content (such as, e.g., regional fat %, segmental fat %, etc.) in a different way. These known systems use electrodes positioned across large regions of the body (e.g., electrodes positioned on two hands, two feet, between two feet and two hands, etc.) to measure the bioimpedance of the body between the electrodes. In contrast, in the devices and methods of the current disclosure, the fat percentage of a user's muscles, such as, e.g., the biceps, is obtained by placing a plurality electrodes (e.g., four) of the device on the biceps, measuring the bioimpedance of tissue in the biceps, and computing an estimate of the fat content from the measured parameters.

The measurements obtained, and the health parameters calculated, using the disclosed systems are significantly different from those obtained by known prior art systems. In the prior art bioimpedance measurement systems, where bioimpedance is measured by positioning electrodes across a relatively large region of the body (between one hand and the other, between one foot and the other, etc.), electrical current finds the path of least resistance. Fat tissue, however, typically has relatively higher resistance. Thus, the applied current flows into, e.g., the foot and then primarily through lean tissue which includes veins and arteries. As a result, a significant portion of the current may flow through the organs of the body between the electrode locations. Therefore, measurements obtained using these prior art systems are very dependent on multiple factors, including, but not limited to, hydration of the body and/or preexisting fat content. In the disclosed systems, electrical current is forced to flow through the subcutaneous fat and then primarily through the muscles in localized regions of the body between the relatively closely spaced electrodes. Consequently, a significant portion of the applied current flows through the most superficial part of the muscles where there are minimal amounts of veins and arteries. Therefore, the impedance values measured (and the health parameters calculated using the measured values) using the currently disclosed systems and methods are believed to be more related to the subcutaneous fat, intramuscular fat, and muscle structure and composition of the localized region, and consequently, of higher accuracy.

In some embodiments, the disclosed systems include a portable, hand-held device, and the disclosed methods include methods to assess health and fitness of localized regions of tissue. In some embodiments, the disclosed device, associated software, and associated methodology provides an instrument and method for measuring parameters related to muscle health and fitness, muscle fatigue and recovery in localized body parts. In some embodiments, the device may be wireless, hand-held, portable, wearable, or incorporated in a garment configured to be worn by a user. Some embodiments of the device may include a display or other indicators such as light-emitting diodes (LEDs), organic LEDs (OLEDs), liquid crystal display (LCD), color-changing fabrics, speaker(s), etc. for immediate feedback of the measured results. Some embodiments of the device may include switches, selectable icons, buttons, or other control mechanisms to control the operation (e.g., to initiate a measurement, configure, etc.) of the device. In some embodiments, the disclosed device may not include a display and/or control mechanisms, and control of the device and presentation of results measured by the device may be performed by an associated device (e.g., a smartphone) wirelessly connected with the disclosed device.

Several arrangements and configurations are presented for the disclosed devices. In some embodiments, the device includes multiple electrodes arranged in a pattern, and measurements may be made using multiple electrode configurations and frequencies. The data from these measurements may be used to calculate parameters related to localized bioimpedance of the measured region. These results are both unexpected and may provide a simple, noninvasive way of measuring and tracking the localized health of the measured region (e.g., muscle fatigue, recovery, etc.) over time. In various embodiments, the disclosed device may be a standalone component (i.e., operate independently of other hardware) handheld device, a device connected or wirelessly linked to an associated device (e.g., a phone, tablet, computer, exercise machine, etc.), a small wearable device integrated with, or removably attachable to, a supporting structure (e.g., belt, strap, headband, armband, etc.), and/or integrated with or removably attached to wearable garment (e.g., a shirt, shorts, or pants), etc. For example, electrodes operably linked to other portions of the disclosed apparatus and system may be suitably integrated with wearable garments using any suitable manner. In some such embodiments, the electrodes may be woven into the fabric using conductive material, and electrically connected to electronics that perform the measurements. In other embodiments, the electrodes may be screen printed or otherwise secured on, e.g., an inner a garment such as a fitted shirt. As a result, the screen printed electrodes may be held in close contact to a user's skin. Still further, the electrodes may be secured to a wearable garment via, e.g., an adhesive.

The disclosed devices and methods may be used for measuring/tracking and/or managing the health (e.g., percentage of fat and/or muscle, muscle quality, etc. in individual muscle groups) of individual body parts. The device may include an electrode array comprising a plurality or electrodes arranged at different angles and distances. To make measurements using the device, the electrode array may be placed in contact with a desired measurement location (e.g., biceps, chest, abdomen, quadriceps, triceps, gastrocnemius, forearms, back muscles, gluteus maximus, etc.) on the body of a user, and measurements initiated. Measurements may be initiated using the device (e.g., by pressing a button on the device) or using a linked associated device (e.g., by pressing a button on a computer, an icon of a software application running on a smartphone, etc.). In some embodiments, upon initiation of measurements, a multi-frequency electrical current signal is applied to the measurement location through multiple electrode pairs of the electrode array and corresponding voltage measurements are made using different multiple electrode pairs. Several exemplary methods for such measurements are described in detail in U.S. Pat. Nos. 8,892,198 and 9,113,808; and U.S. Patent Application Nos. 2010/0292603 and 2012/0245436.

In some embodiments, the device may include electrical/electronic circuits (e.g., integrated circuits such as a microprocessor, etc.) to make the measurements and to calculate health-related parameters based on the resulting data. In some embodiments, profile information (e.g., age, gender, weight, height, race, temperature, etc.) of the user may also be used in these calculations. The calculated parameters may include parameters such as muscle percentage, fat percentage, muscle quality, muscle fitness, and muscle health, etc.

In some embodiments, the calculated parameters may be displayed on a screen of the device (LED, LCD, Thin Film Transistor, Organic LED, etc.) or may be shown using other indicators such as color-changing fabrics, lights, speakers, etc. In some embodiments, the calculated parameters may be sent (wirelessly, or through wires) to an associated device (smartphone, tablet, computer, watch, etc.) and displayed on a screen of the associated device. In some embodiments, the raw data collected by the device (e.g., current, voltage, resistance, reactance, phase, impedance at multiple frequencies and multiple electrode configurations, etc.) may also be sent to the associated device. Any known wireless communication technology (e.g., Bluetooth, Wi-fi, Zigbee, etc.) may be used to transmit information (data, computed parameters, instructions, signals, etc.) between the device and its associated devices. In some embodiments, low energy Bluetooth may be used to transfer information between the devices.

In some embodiments, the disclosed device and/or the associated device may transfer some or all of the received information to a central database (e.g., on the cloud) over the internet. The central database may be configured to store the data and present results in a variety of ways. The user may access the database over the internet and review these results using a personal computer, smartphone, tablet, or a similar device. In some embodiments, the disclosed device and/or the linked associated device may be configured to transfer or output the measured data and/or the computed results to third-party health-tracking software for tracking, to participate in group health activities, etc. In some embodiments, the disclosed device and/or the linked associated device may be configured to access, download, and/or link to third-party websites (or software) to provide health-related information to the user.

Using the disclosed device and method, the user may be able to obtain and track the health of specific regions of his body, get health-related information (for example, an exercise to improve the health of any particular region), and participate in health-related group activities, etc. In some embodiments, the disclosed device and method may be capable of measuring/tracking and/or managing the level of fatigue/injury in muscles as a result of activity, as well as the rate and level of recovery. This is based on the unexpected observation that certain bioimpedance parameters change dramatically in response to muscle exertion. For example, in an experiment conducted with three healthy men between the ages of 30-35, parameters such as reactance and phase at 50 kHz increased in value slightly during exercise (5-15% increase compared to baseline), then dropped dramatically (20-50% reduction compared to baseline) within 30 minutes of exercise, and then returned gradually to values near baseline (within 10% of baseline) over the course of 8-48 hours. These results are both unexpected and important as they provide a simple, noninvasive way of measuring and tracking muscle fatigue and recovery.

In some embodiments, a portable device for measuring bioimpedance-related properties of tissue is disclosed. The device may include a portable housing, a power supply in the housing, and a plurality of electrodes on a surface of the housing. The plurality of electrodes may include a first pair of current electrodes and a corresponding first pair of voltage electrodes positioned between the first pair of current electrodes. The device may also include electronic circuitry in the portable housing. The electronic circuitry may be configured to (a) obtain data by directing current into the tissue through the first pair of current electrodes and measuring a voltage across the corresponding first pair of voltage electrodes, and (b) calculate at least one bioimpedance-related property of the tissue based on the obtained data.

Embodiments of the disclosed device may include one or more of the features described below. The portable housing may include a display configured to indicate the calculated bioimpedance-related property. The housing may include at least one indicator configured to indicate a status of the measurement to a user. At least one indicator may be configured to indicate at least one of when (a) the plurality of electrodes make contact with the tissue and (b) when the measurement is complete. Each of the first pair of current electrodes may be larger in size than the corresponding first pair of voltage electrodes. The electronic circuitry may be further configured to wirelessly transmit at least the calculated bioimpedance-related property to an associated device adapted to display the bioimpedance-related property. The associated device may include one of a cellular phone, a computer, a tablet, and an exercise machine. The electronic circuitry may be configured to calculate at least one of (i) a fat percentage of the tissue and (ii) a muscle percentage of the tissue using the obtained data. The electronic circuitry may be further configured to calculate a muscle quality of the tissue as a ratio of the muscle percentage to the fat percentage. The device may further include a light ring extending around a periphery of the device. The light ring may be configured to illuminate to indicate a status of the device.

In some embodiments, a portable device for measuring bioimpedance-related properties of tissue is disclosed. The device may include a plurality of electrodes. The plurality of electrodes may be configured to be simultaneously placed in contact with the tissue. The plurality of electrodes may include a first set of electrodes arranged along a first axis. The first set of electrodes may include a first pair of current electrodes and a first pair of voltage electrodes positioned between the first pair of current electrodes, and a second pair of current electrodes and a second pair of voltage electrodes positioned between the second pair of current electrodes. The plurality of electrodes may also include a second set of electrodes spaced apart and arranged along a second axis non-collinear with the first axis. The second set of electrodes may include a third pair of current electrodes and a third pair of voltage electrodes positioned between the third pair of current electrodes. Each electrode of the first, second, and third pairs of current electrodes and voltage electrodes may be spaced apart from the other electrodes of the first, second, and third pairs of current electrodes and voltage electrodes. The device may also include electronic circuitry configured to obtain (i) first data by directing current at multiple frequencies through the first pair of current electrodes and measuring the voltage across the first pair of voltage electrodes, and (ii) second data by directing current at multiple frequencies through the third pair of current electrodes and measuring the voltage across the third pair of voltage electrodes.

Embodiments of the disclosed device may include one or more of the features described below. The device may further include a screen configured to display a parameter related to at least the first data and the second data. The electronic circuitry may be configured to wirelessly transmit a parameter related to at least the first data and the second data to an associated device configured to display the parameter. The electronic circuitry may be further configured to (iii) obtain third data by directing current at multiple frequencies through the second pair of current electrodes and measuring the voltage across the second pair of voltage electrodes. The electronic circuitry may be further configured to calculate a bioimpedance-related property as a function of one or more of the first data, the second data, and the third data.

In some embodiments, a method of measuring a characteristic of a user's tissue is disclosed. The method may include positioning a plurality of electrodes of a portable device in contact with a first location of the tissue. The plurality of electrodes may include a first pair of current electrodes and a corresponding first pair of voltage electrodes. The method may also include obtaining data by directing a current into the first location of tissue through the first pair of current electrodes and measuring a voltage across the corresponding first pair of voltage electrodes. The method may further include calculating at least one characteristic of the tissue at the first location based on the obtained data.

Embodiments of the disclosed method may include one or more of the aspects described below. The method may further include repeating the steps of positioning, obtaining, and calculating at a plurality of locations of the tissue. Each of the plurality of locations may include a muscle group that differs from a muscle group of the other plurality of locations. The method may further include calculating a whole body characteristic of the user as a function of the at least one characteristic calculated for the plurality of locations. The whole body characteristic may include at least one of a total body fat percentage, total body muscle percentage, and total body muscle quality. The method may further comprise wetting the plurality of electrodes or the tissue prior to positioning the plurality of electrodes in contact with the tissue.

BRIEF DESCRIPTION OF THE FIGURES

The accompanying drawings, which are incorporated in and constitute a part of this specification, illustrate exemplary embodiments of the present disclosure and together with the description, serve to explain the principles of the disclosure.

FIGS. 4A-4I illustrate an exemplary process of setting up an associated device to operate the device of FIG. 2.

FIGS. 8A-8F illustrate an exemplary process of reviewing measurement results on the associated device.

FIGS. 9A-9F illustrate an exemplary processing of reviewing measurement results on the device of FIG. 2.

FIG. 10A illustrates an exemplary electrode array of the device of FIG. 2.

FIGS. 10B-10C illustrate other exemplary electrode arrays of the device of FIG. 2.

FIG. 18 is a table showing the results of FIG. 17.

FIGS. 19-20 are tables showing other exemplary results obtained by the device.

DETAILED DESCRIPTION OF THE DISCLOSURE

The present disclosure will now be described with reference to several exemplary embodiments of a disclosed device and methods of using the device. In the discussion below, some specific components and/or features of the disclosed devices are described only with reference to some embodiments. It should be noted that this is done only for the sake of brevity and convenience and not intended to limit the disclosure. A person of ordinary skill in the art would recognize that the components and/or features described with reference to one embodiment may also be present in other embodiments unless expressly indicated otherwise. It should further be noted that, although the disclosed devices and methods are described in the context of a user tracking the improvement of muscle health with exercise, this is only exemplary. A person of ordinary skill in the art would recognize that the concepts underlying the devices and methods of the current disclosure may be utilized in any device or procedure, medical or otherwise.

As used herein, the terms "comprises," "comprising," or any other variation thereof, are intended to cover a non-exclusive inclusion, such that a process, method, article, or apparatus that comprises a list of elements does not include only those elements, but may include other elements not expressly listed or inherent to such process, method, article, or apparatus. The term "exemplary" is used in the sense of "example," rather than "ideal."

Figure 1:
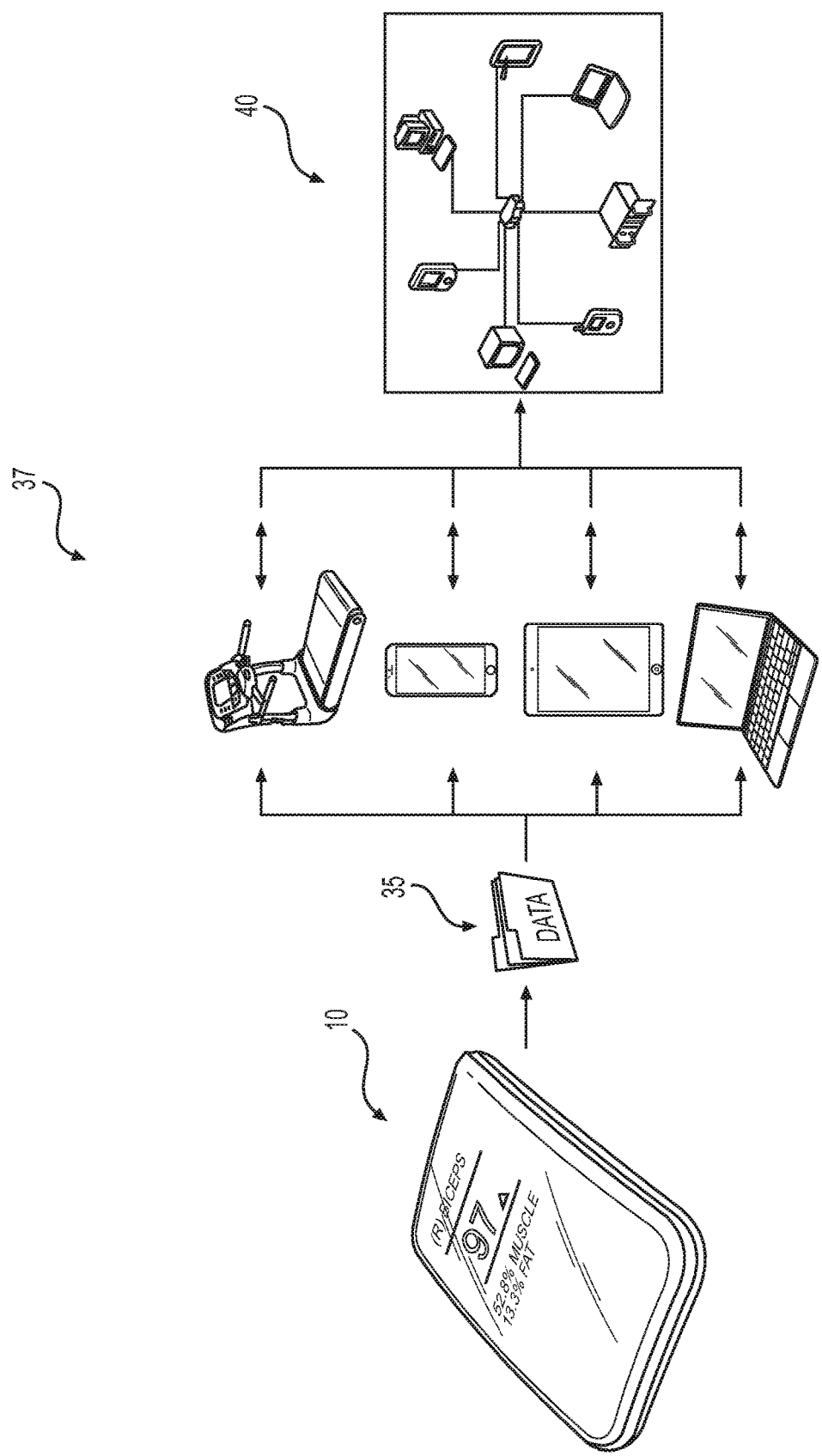
FIG. 1 illustrates an overview of the system including an exemplary aspect of the disclosed device.

FIG. 1 illustrates an overview of an exemplary system of the current disclosure. The system includes a device 10 used to measure EIM or any type of data related to the bioimpedance of a user. Bioimpedance refers to the electrical properties of a biological tissue, measured when current flows through it. Bioimpedance varies with the current frequency and tissue type, and may be used as a measure of the body composition (e.g., percentage of body fat in relation to lean body mass). EIM and other metrics related to bioimpedance may play an important part of any comprehensive health and nutrition assessment of a user. Device 10 may be a portable device. In general, device 10 may have any size and shape. In some embodiments, device 10 may have a length and width between about 0.5-6 inches. In some embodiments, device 10 may have a width of about 2.5 inches and a length of about 3.5 inches. In this disclosure, relative terms such as "about," "substantially," etc. indicate a possible variation of ten percent. It is also contemplated that, in some embodiments, the device may have a circular, oval, or other curved footprint or profile (see, for e.g., FIG. 10C). In some embodiments, device 10 may be configured to be attached (for example, strapped) to a user (for example, at the bicep) during exercise. For example, in some embodiments, device 10 may include straps (or loops or openings configured to pass a strap) that may be used to attach the device 10 snugly to the user's body. In some embodiments, a user may merely press the device 10 against his/her skin to take a measurement. In some embodiments, the electrodes may be woven into fabric on a garment such as a shirt, shorts, pants, or socks, and connected to electronics that perform the measurements, as alluded to above.

Figure 2:
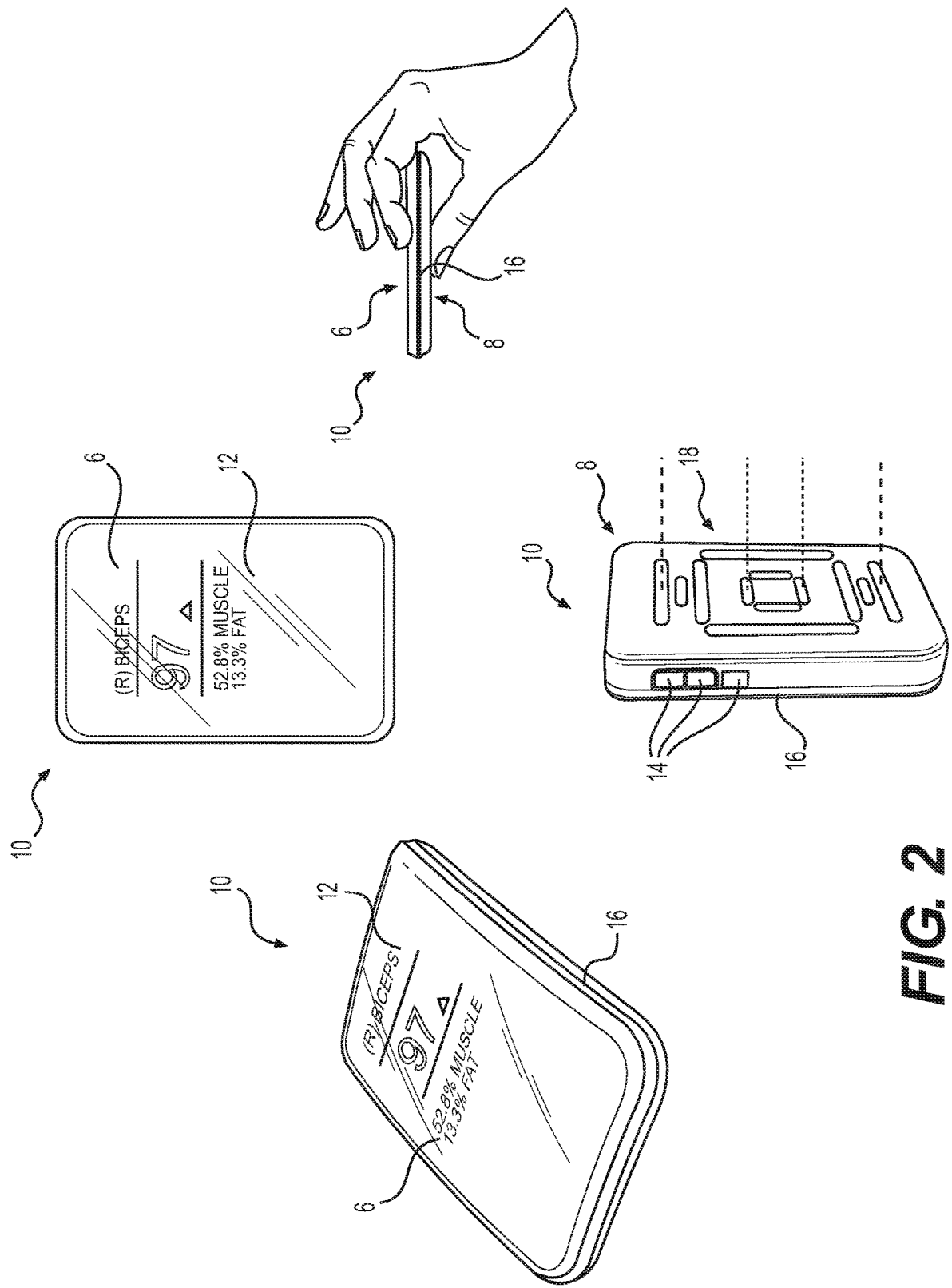
FIG. 2 illustrates several views of the device of FIG. 1.

FIG. 2 illustrates several views of an exemplary device 10. In the description that follows, reference will be made to both FIGS. 1 and 2. Device 10 may include one or more buttons 14 to navigate and control the device 10 (e.g., initiate measurements, etc.). In general, device 10 may include any number (1, 2, 3, 4, etc.) of buttons 14 positioned on any location in the device 10. In some embodiments, the number of buttons 14 may be three. Although physical buttons are illustrated in these figures, it should be noted that in some embodiments, some or all of these buttons 14 may be software-generated icons that appear on a display screen of the device 10. Device 10 may include a display screen (display 12) configured to display data. Display 12 may be of any type (e.g., thin film transistor (TFT), liquid crystal display (LCD)), organic light emitting diode (OLED), etc.). In a preferred embodiment, an OLED display may be used. Display 12 may have any size and shape, and may be positioned at any location on the device. In some embodiments, the display 12 may be positioned on a front-side 6 (or a non skin contacting side) of the device. In some embodiments, the display 12 may extend substantially over the entire front-side 6 of the device 10. Device 10 may be powered by a battery (not shown). In some embodiments, the battery may be a rechargeable battery.

In some aspects, device 10 may be configured to initiate measurements automatically when the device 10 senses that the electrodes are making proper contact with a user's skin. For example, one or more electrodes of device 10 may be configured to continuous or periodically deliver relatively small amounts of current. It is contemplated that once the electrodes are properly positioned on the user's skin, these small amounts of current may be transmitted through the user's skin and detected by other electrodes 18, to confirm correct positioning on the user's skin. Once suitable amounts of the delivered current is detect by one or more electrodes 18, device 10 may be configured to initiate measurements In some embodiments, measurements are made periodically to detect changes in the tissue over time. That is, a plurality of measurements may be made with one or more predetermined time delays between each measurement of the plurality of measurements. In some embodiments, however, the measurements may be made continuously. That is, a plurality of measurements may be made in succession with little to no time delay between each measurement. Furthermore, in aspects of the present disclosure, sensed data may be stored in a local memory on the device. The data may be analyzed on the device via a suitable processor and/or transmitted wirelessly to another device or a database, for later analysis. Those of ordinary skill will recognize that some or all of the obtained data (e.g., data for a particular set of measurements, data spanning a particular time period, data falling within certain predefine criteria or threshold) may be transmitted wirelessly to linked device or database. If necessary, the linked device or database may be configured to request additional such as a complete set of data relating to all measurements.

Device 10 may include a plurality of electrodes 18 to measure data associated with the bioimpedance of a body part of the user. In general, these electrodes 18 may be positioned at any location on the device 10. In some embodiments, the electrodes 18 may be positioned on the side opposite front-side 6. That is, the electrodes 18 may be positioned on the back-side 8 (or a skin contacting side) of the device 10. Although FIG. 2 illustrates the electrodes 18 as being positioned on a side opposite the display 12, this is not a requirement. For example, in some embodiments, the electrodes 18 may be positioned alongside the display 12, or on a side adjacent to the display 12. In use, the electrodes 18 may be kept in contact with a region of the user's body (e.g., bicep, thigh, etc.) and the measurement initiated.

The measurement may be initiated by any method. In some embodiments, a measurement may be initiated by pressing a button 14 of device 10. In some embodiments, the measurement may be initiated by pressing a button or an icon (e.g., in an software app) of an associated device 37 (see FIG. 1). In some embodiments, the measurement may be initiated automatically when the device recognizes that sensors are making proper contact. The associated device 37 may be any type of electronic device that is configured to exchange information (data, signals, etc.) with device 10. In some embodiments, the associated device 37 may be a smartphone, tablet, smartwatch, computer, exercise machine (e.g., treadmill, elliptical), etc. that is communicatively coupled to device 10 for exchange of information. In general, information may be exchanged by any method (wirelessly, using a wired connection, optical, transferred using a physical medium such as a memory stick, etc.) between devices 10 and 37. In some embodiments, information may be exchanged wirelessly using any wireless or mobile phone communication technology (Bluetooth, WiMax, Wi-Fi, ZigBee, Microwave, Infrared, 3G, 4G, etc.). The measurement of each region may take any amount of time. In some embodiments, each measurement may take less than 2 seconds. After completion of the measurement of one region (e.g., bicep), the device 10 may be moved to another region (e.g., thigh) to take measurements.

After the completion of a measurement, the device 10 may inform the user of the completion. The device 10 may use any method to inform the user (for example, by emitting a sound, vibration, light, display changing color, etc.). In some embodiments, device 10 may include a light or an indicator to relay measurement status information (e.g., status of electrode contact to the user's body, measurement has been initiated, measurement is completed, etc.) to the user. For example, the light may be activated to indicate that all electrodes 18 have made good contact with the skin, etc. In some embodiments, a light ring 16 positioned around the device 10 may be used to relay measurement status information (e.g., when the device is ready to take a measurement, when a measurement is complete, etc.) to the user. In a preferred embodiment, the light ring 16 may be used to inform the user that good contact is made, a measurement has been initiated, and a measurement has been completed. In some embodiments, vibration, sound, or another signal that can be sensed by the user may indicate the measurement status. In some embodiments, the device 10 may also inform the user when a measured parameter is outside an expected range. For example, the device 10 may beep (i.e., alert by emitting a sound), vibrate, activate light ring 16, etc. when the results of a measurement are outside of a normal range and/or outside an expected range (e.g., based on past measurements). A measurement outside an expected range may, in some cases, indicate an error in the measurement. In some embodiments, device 10 may be designed to be splash proof or otherwise water resistant. That is, device 10 may include a hermetically sealed outer case to protect, e.g., internal electronics. In a preferred embodiment, device 10 may be fully submersible and thus water-proof.

Although FIG. 2 illustrates an embodiment of a device 10 integrated with electrodes 18 and display 12 in a single housing, this is only exemplary. In some embodiments, some of these components may be eliminated or may be incorporated in separate housings. For example, in some embodiments, the device 10 may include the electrodes 18 for making measurements, and the display 12 may be integrated with another device (e.g., associated device 37) that is linked (e.g., wirelessly connected) to the device 10. In such embodiments, measured data may be transmitted from device 10 to the linked associated device 37 for computation and/or display. In some embodiments, the electrodes 18 (or device 10 itself) may be in the form of one or more detachable sensors that are attached to the user or to garments (e.g., headband, wristband, strap, chest band, shirt, shoes, shorts, socks, etc.) worn by the user. These detachable sensors may connect (wirelessly or through a wired connection) to the device 10 or the associated device 37 and transfer the data measured by the sensors. In some embodiments, initiation of measurements of these detachable sensors may be made using the associated device 37 (e.g., using a software application running on the associated device 37). It is also contemplated that, in some such embodiments, the device 10 and/or the electrodes 18 may be in the form of one or more flexible components (e.g., electrodes 18 and related circuitry patterned on a flexible substrate) that may be attached to desired locations (e.g., bicep, chest, etc.) of a user like a sticker.

The device 10 may measure data and display the measured data on display 12. In some embodiments, as will be described in more detail below, the device 10 may analyze the measured data and compute health parameters 35 (see FIG. 1) related to the health of the user. The health parameters 35 may include metrics related to the user's physical heath (e.g., muscle percentage, fat percentage, muscle quality (MQ), etc.). The device 10 may display all or a portion of these computed parameters 35 on display 12. Additionally or alternatively, in some embodiments, the device 10 may direct some (or all) of the measured data and computed parameters 35 to the associated device 37. As described previously, device 10 may send the parameters 35 to the associated device 37 by any method (over a wire, wirelessly, or transferred in a transferable storage medium, etc.). In some embodiments, the device 10 and associated device 37 may communicate wirelessly. The parameters 35 may be formatted (or configured) in a manner suitable to be viewed using the associated device 37 having a suitable application installed therein.

In some embodiments, the associated device 37 may transmit some or all of the parameters 35 to a computer system 40 for storage and/or further analysis (e.g., trend analysis, etc.). Any type of known computer (e.g., desktop, laptop, networked computers, server, etc.) may serve as computer system 40. In some embodiments, networked servers connected over the internet may serve as computer system 40. In some embodiments, a plurality of networked computers may serve as computer system 40. In some embodiments, an associated device 37 may itself function as the computer system 40. Computer system 40 may include a storage medium with a database having parameters 35 from previous measurements stored therein. Although the computer system 40 is described as including the storage medium with a database, it should be noted that the storage medium may be distributed across multiple networked computers (e.g., on a server farm) and the database may be stored in a cloud (e.g., a cloud computing system). Computer system 40 may store the transferred health parameters 35 in the database and, in some embodiments, perform analysis on the stored data. Computer system 40 may include known electronic devices (microprocessor, math processing unit, etc.) and circuitry configured to perform the analysis. The analysis may include tracking the variation of the user's health parameters 35 over time, etc. In some embodiments, the user may access the computer system 40 (e.g., over the internet) to review the results of the analysis. In some embodiments, the results of the analysis performed by the computer system 40 may be retransmitted to and displayed on display 12 of the device 10.

Figure 3:
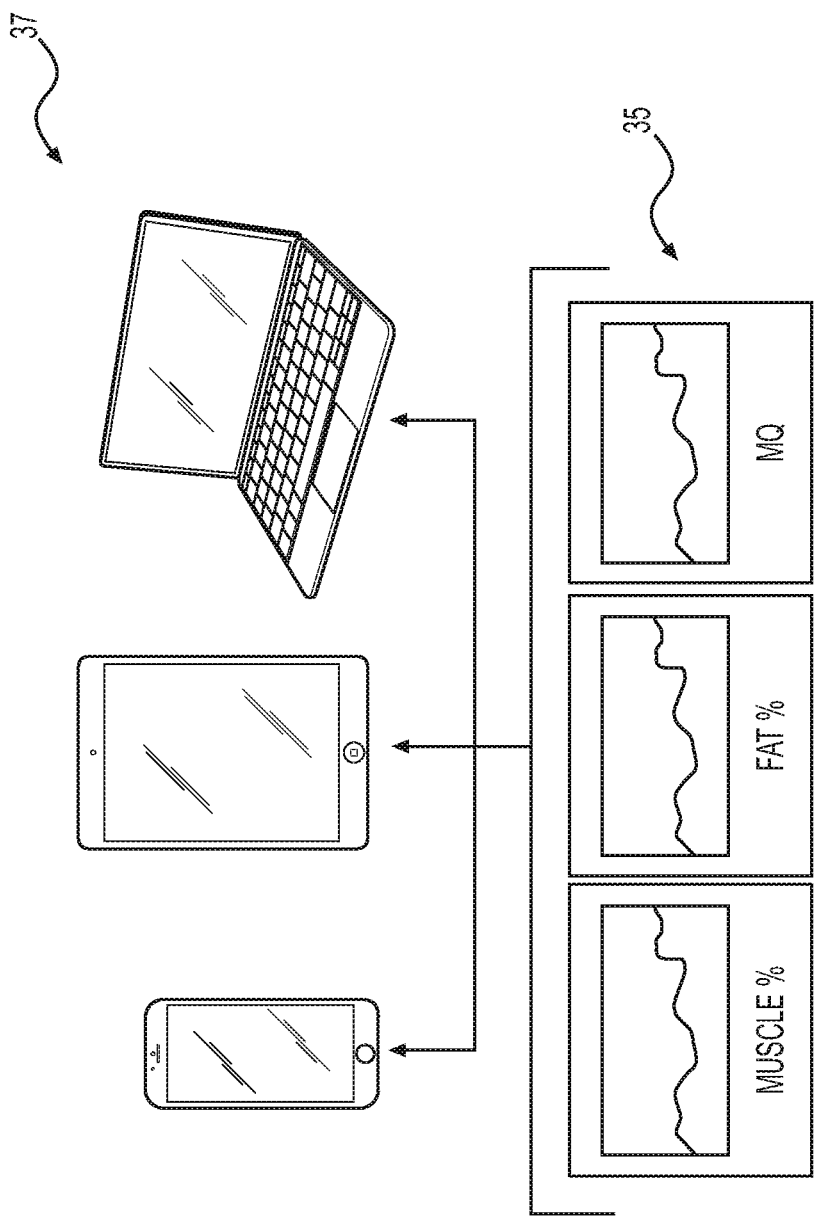
FIG. 3 illustrates how data stored in the system can be reviewed using any associated device.

A user may log into computer system 40 to view the calculated parameters 35 and/or the trend analysis performed by the computer system 40 (e.g., variation of MQ over time). In some embodiments, as illustrated in FIG. 3, a user may access the computer system 40 using an associated device 37 to view the parameters 35 (and/or other health-related data). In addition to the database and software configured to perform analysis on the measured data, computer system 40 and/or the associated device 37 may also include software configured to control operation of the device 10. A user may use this software to operate the device 10 (e.g., set up a personal account, manage the account, setup and customize the device, initiate measurements, etc.). The user may access the software (e.g., using device 10, associated device 37, a web application, a desktop client, etc.) to setup the device 10 and to setup a profile. The profile may allow the user to enter user specific information such as age, gender, weight, height, etc. In some embodiments, the system may enable multiple users to create profiles (for example, guest profiles) in a single device 10. Each user may access and modify their profiles and view their measured health parameters 35.

The software associated with computer system 40 and/or the associated device 37 may also enable the user to view exercise videos/tutorials and set motivational goals. The software also may be configured to enable sharing of the parameters 35 and other data with friends directly or through social network sites to compare results. In some embodiments, the computer system 40 and/or the associated device 37 may be configured to access the Application Programming Interface (API) of companies that provide complementary information (such as sleep patterns, nutritional information, and other fitness information) and combine this information with the data stored in the computer system 40. The system may compare and/or combine this third-party information with individual user data to educate the user on their health and well-being (for example, compare the user's metrics to known risk factors for disease, data from studies, etc.). Using the measured health parameters 35 of a user, the system may customize exercise routines for the user to follow, and inform the user about maintenance of their health and fitness.

In some embodiments, during setup, the user may be asked to manually select each body part via display 12 of the device 10 and/or the display (e.g., display 52 in FIGS. 4A-9F as described below) of an associated device 37, and to measure the corresponding muscle on their body. These measurements may be used as a baseline for subsequent measurements. In some embodiments, after the initial setup, the device 10 may be trained to recognize individual muscles so that measurement can begin as soon as the electrodes 18 come in contact with the user's skin. In some embodiments, measurements taken on the device 10 may be automatically synced with the user's profile on computer system 40 and/or the associated device 37 so that real time parameters 35 may be accessible to the user. Although in the description above all the health parameters 35 are described as being computed in the device 10, this is only exemplary. In some embodiments, some or all of the health parameters 35 may be computed on the computer system 40 and/or the associated device 37 or by a third party having access to information obtained by device 10. In some embodiments, computer system 40 and/or the associated device 37 may allow the user to customize the device 10 (e.g., change the appearance and/or the type of information displayed on display 12, color of the light ring 16 and/or the display 12, etc.).

Figure 4B:
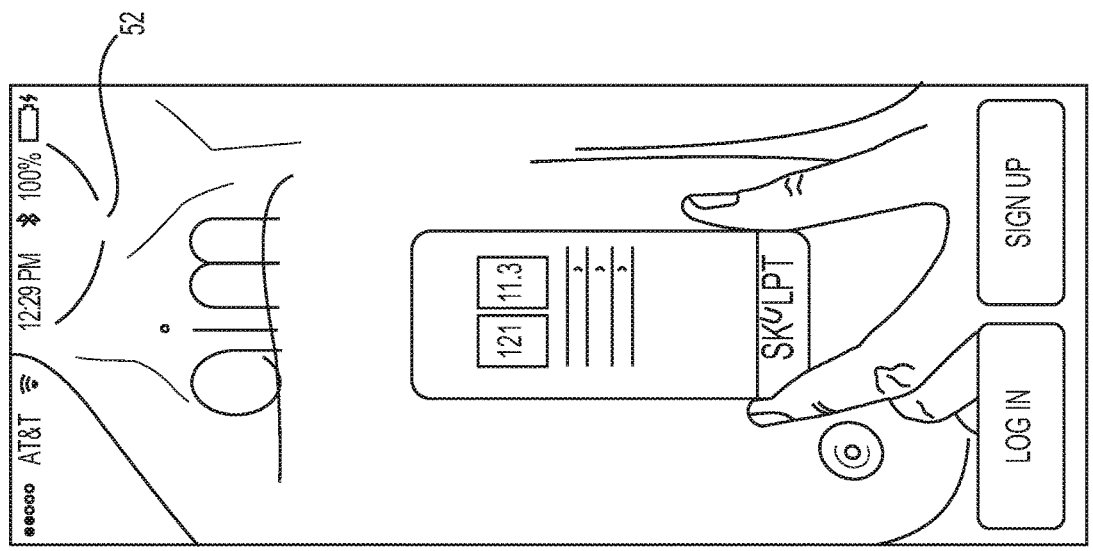
Figure 4A:
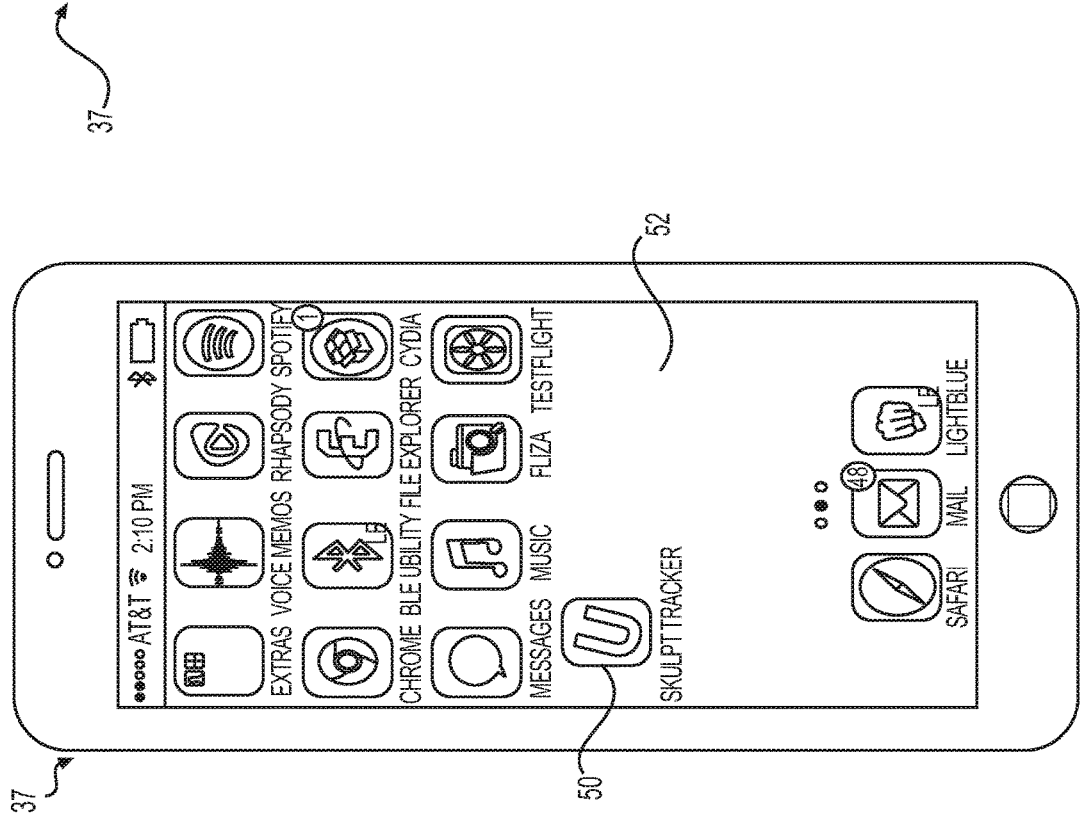
Figures 4C, 4D, 4E:
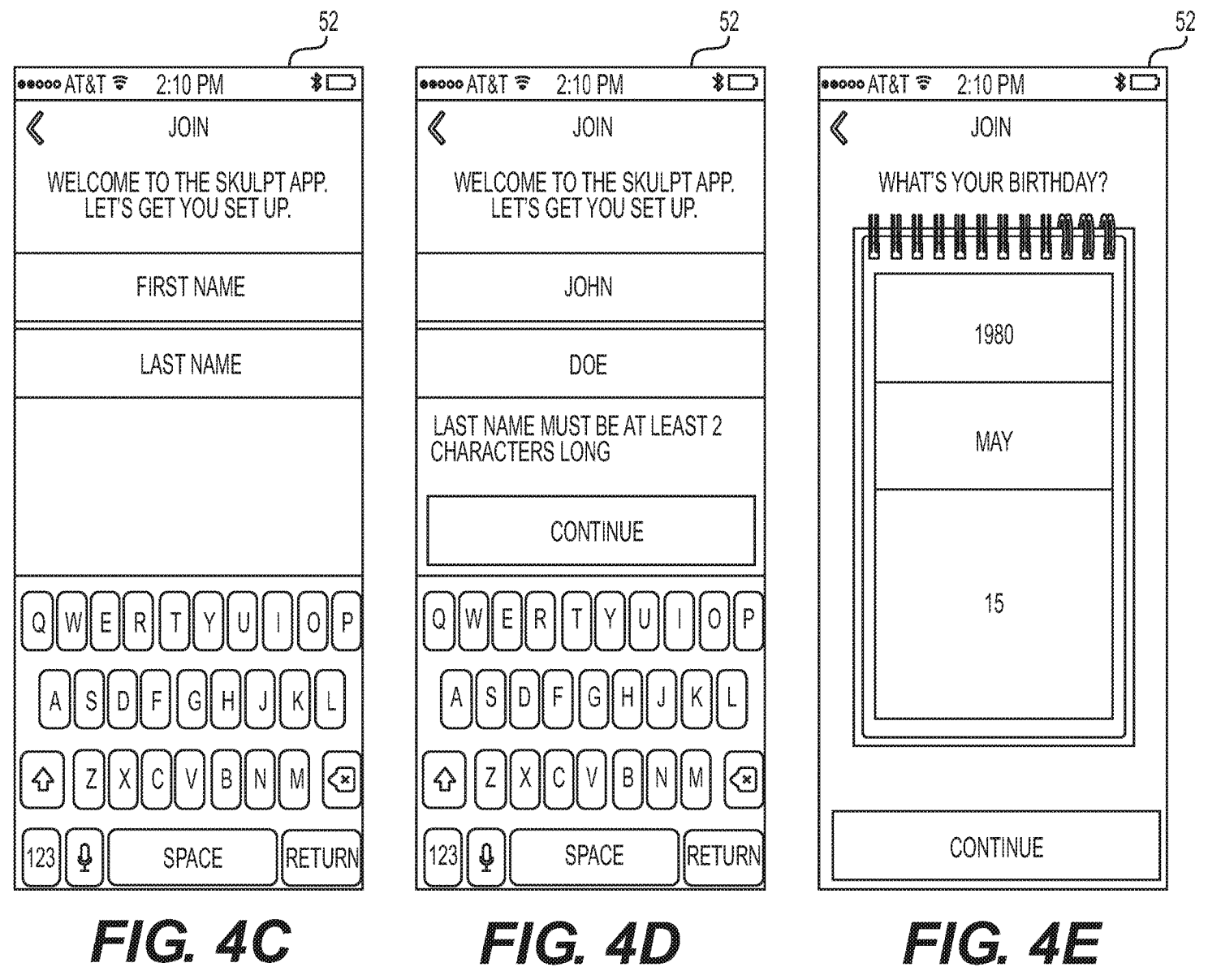
Figure 4H:
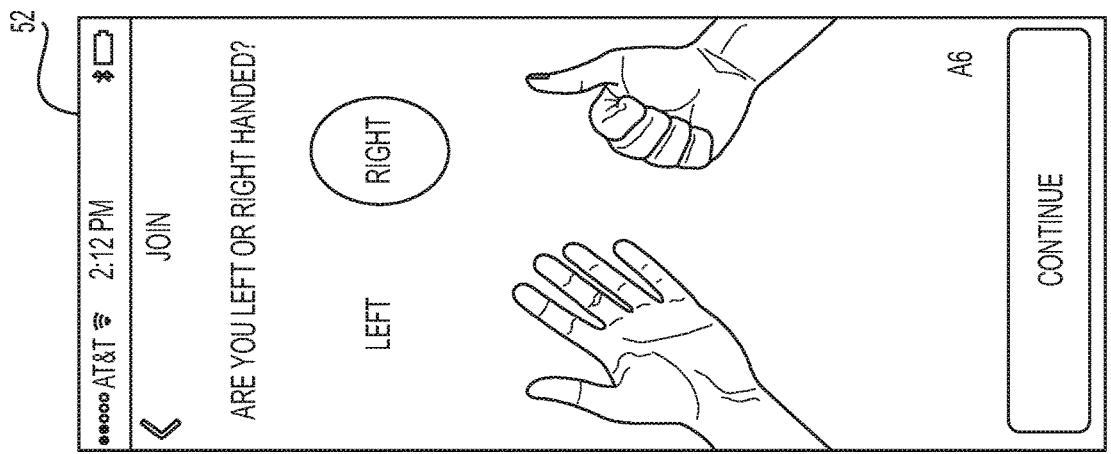
Figure 4G:
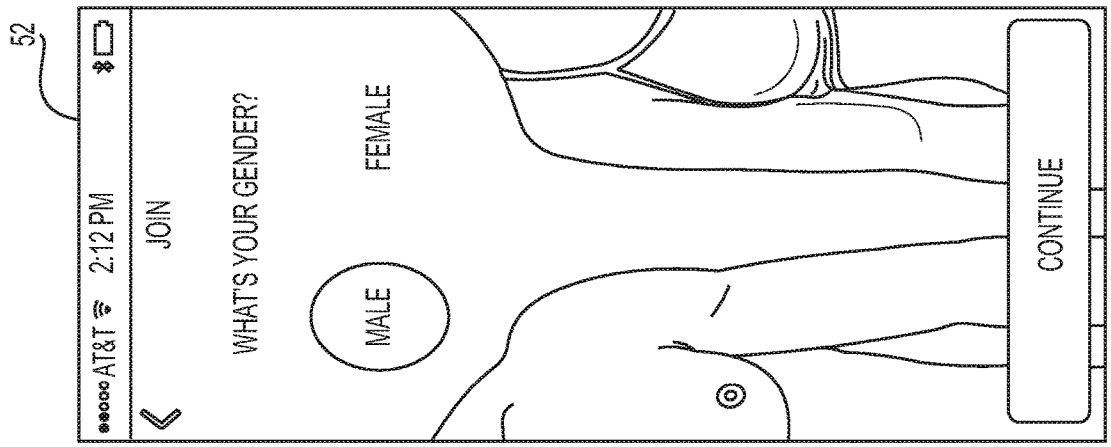
Figure 4F:
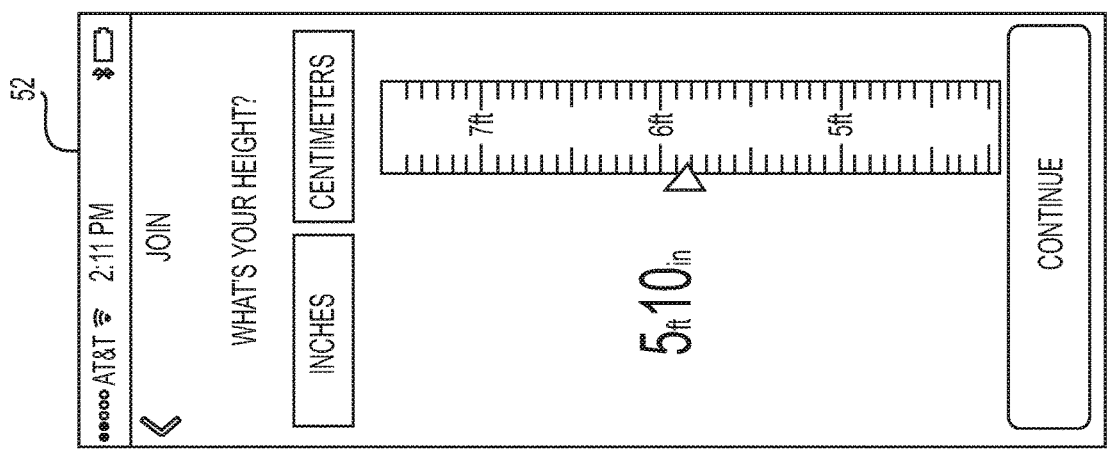
Figure 4I:
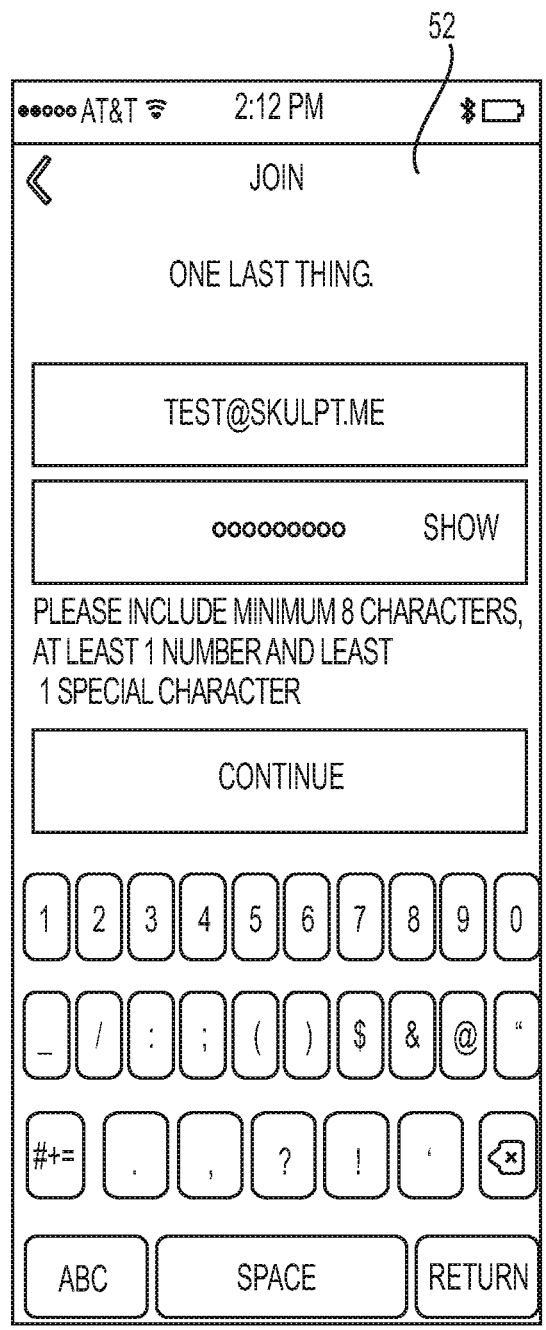
Figure 5C:
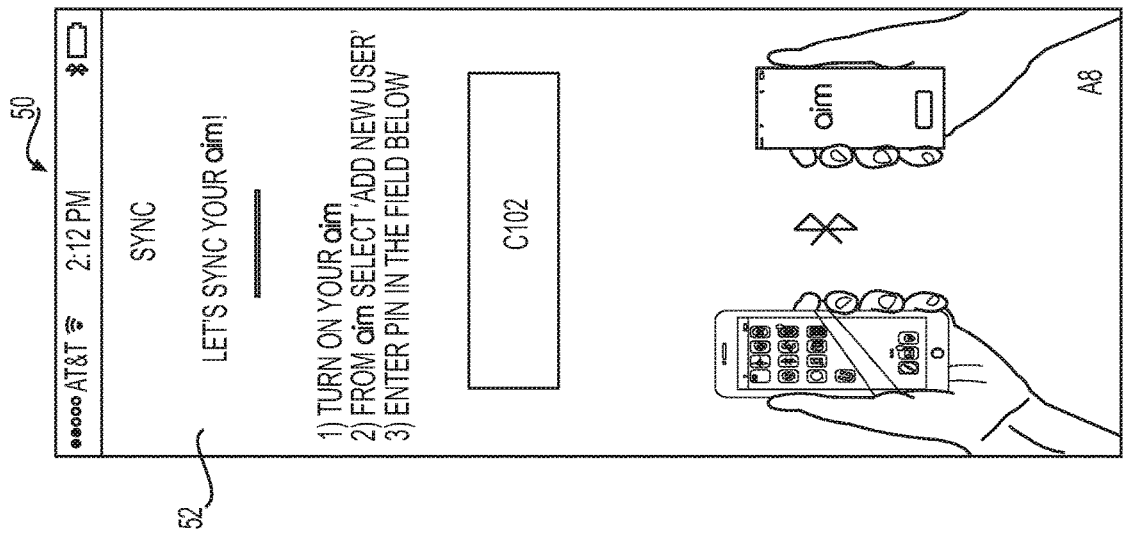
FIGS. 5A-5E illustrate an exemplary process of syncing the associated device with the device of FIG. 2.
Figure 5B:
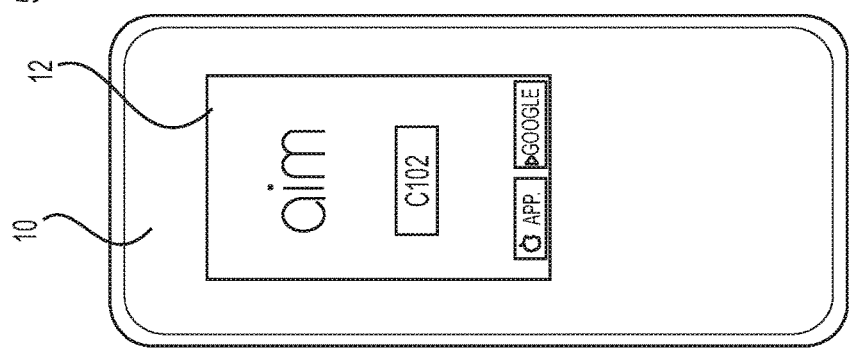
Figure 5A:
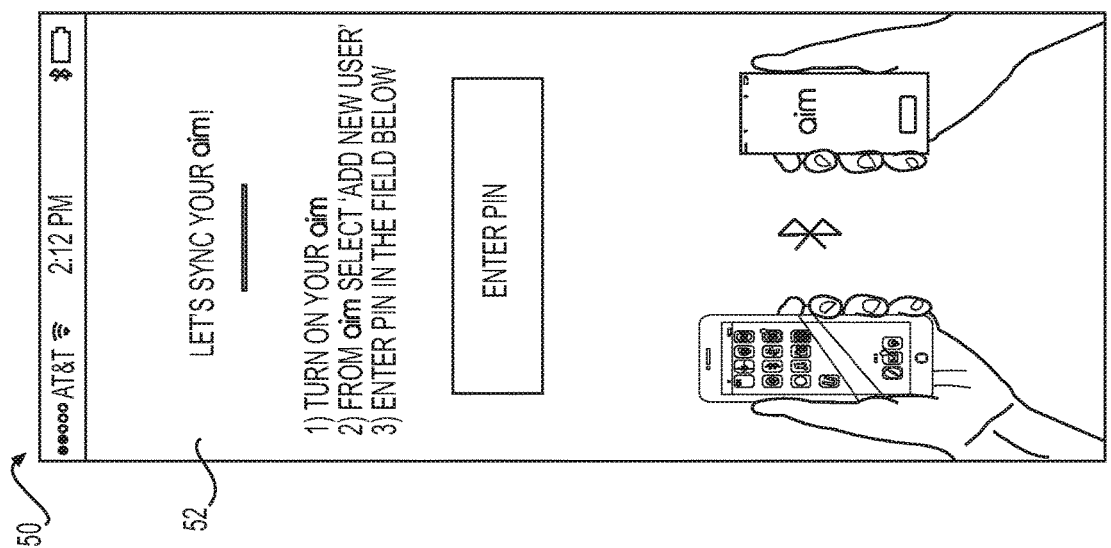
Figure 5E:
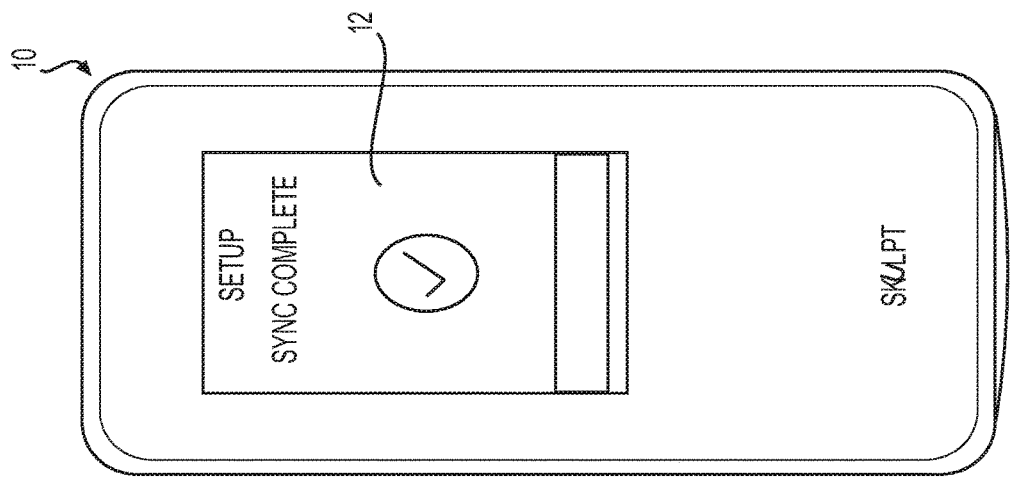
Figure 5D:
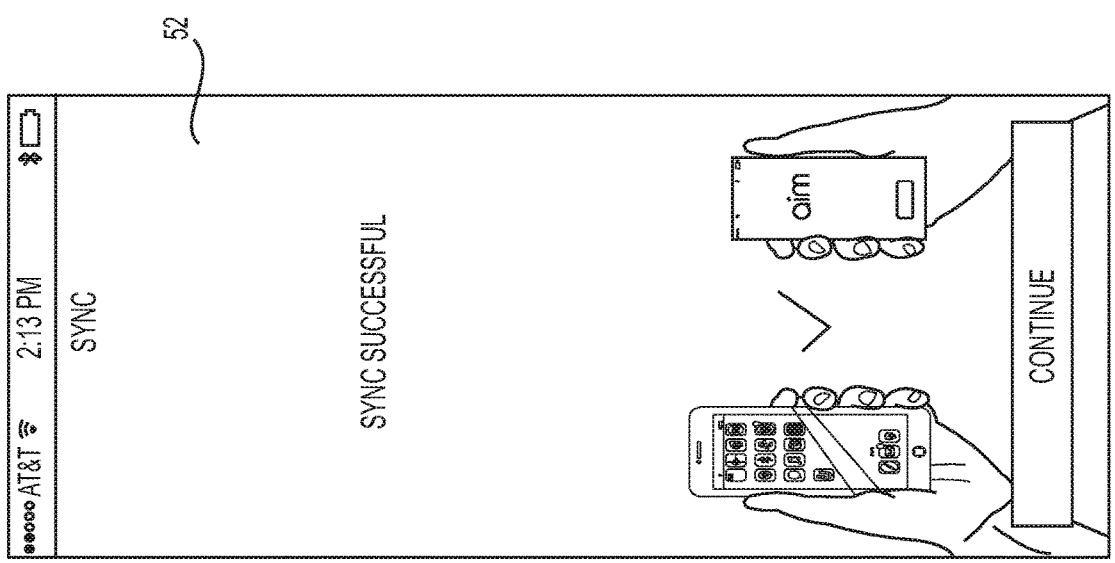

An exemplary method of using an iPhone® as an associated device 37 to operate a disclosed device 10 will now be described with reference to FIGS. 4A-9F. It should be noted that the described associated device 37, device 10, and method are only exemplary and many other variations (as described throughout this specification) are possible. A software application (app 50) is first downloaded to the associated device 37 from a suitable online site (such as, Itunes®). FIG. 4A illustrates the downloaded app 50 on the display screen 52 of device 37. When the app 50 is opened (e.g., by clicking on it), a login window allows a registered user to "log in" and a new user to "sign up" (see FIG. 4B). When the "sign up" icon is selected, the app 50 sequentially displays multiple windows that allow the user to input profile information and select a login ID (e.g., an email address) and password for future login (see FIGS. 4C-4I). In the illustrated example, the requested profile information includes e.g., name, birthday, height, gender, weight, and whether the user is left or right handed. However, as a person of ordinary skill in the art would recognize, any type of information can be requested from the user as profile information. The app 50 then prompts the user to synchronize (sync) or pair the device 10 with the associated device 37 (see FIGS. 5A-5E). Synchronization or pairing operatively couples or links the associated device 37 with the device 10 so that the device 10 may be controlled/operated using the associated device 37. In the synchronization routine illustrated in FIGS. 5A-5E, the app 50 prompts the user to activate (i.e., turn on) the device 10 and select the "Add New User" icon that appears on the display 12 (of device 10) upon activation (see FIG. 5A). Upon following these instructions, the device 10 displays a PIN number on its display 12. Upon entering this PIN number in the app 50 (FIG. 5C), the associated device 37 synchronizes or pairs the device 10 with the associated device 37. The associated device 37 can now be used to control the device 10 (change settings, initiate measurements, perform calculations, review results, etc.). In some embodiments, a single device 10 may be synced with multiple associated devices 37, and multiple devices 10 may be synced with a single associated device 37 using a similar procedure. In some embodiments, multiple users may also create separate accounts in the app 50 to use the same device 10 and associated device 37.

Figure 6A:
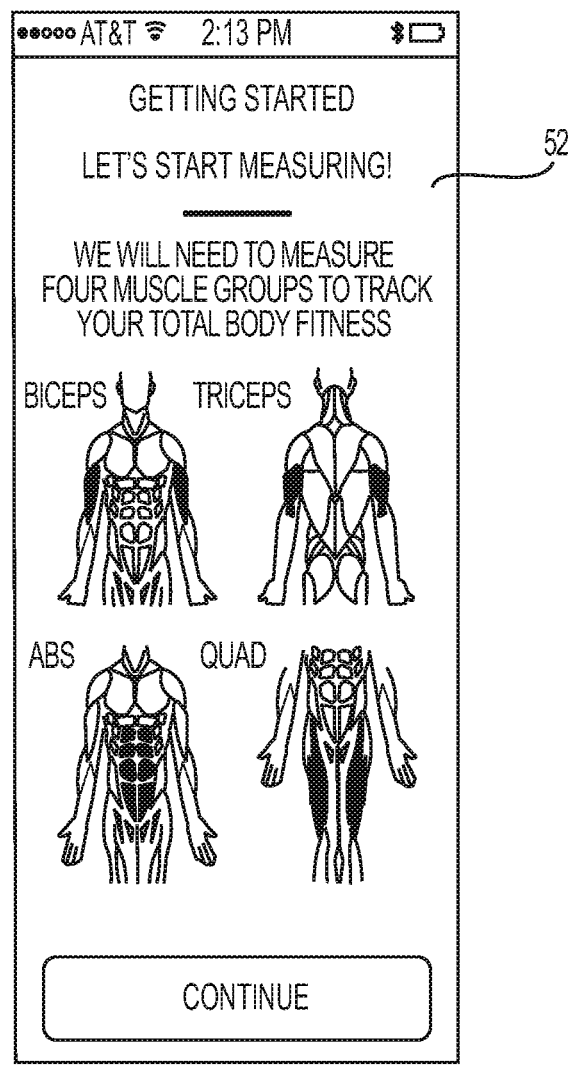
FIGS. 6A-6J illustrate an exemplary process, via screenshots of a mobile device, for obtaining baseline measurements of a user's body using the associated device and methods.
Figure 6D:
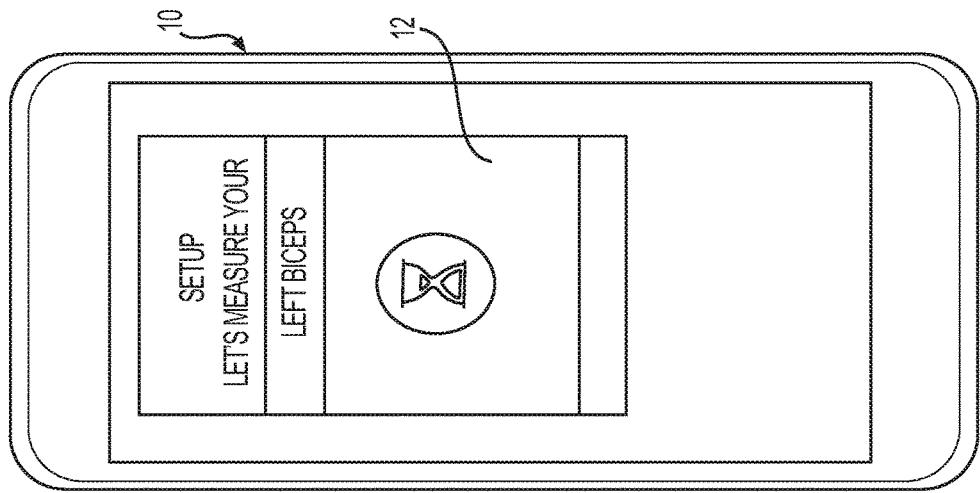
Figure 6C:
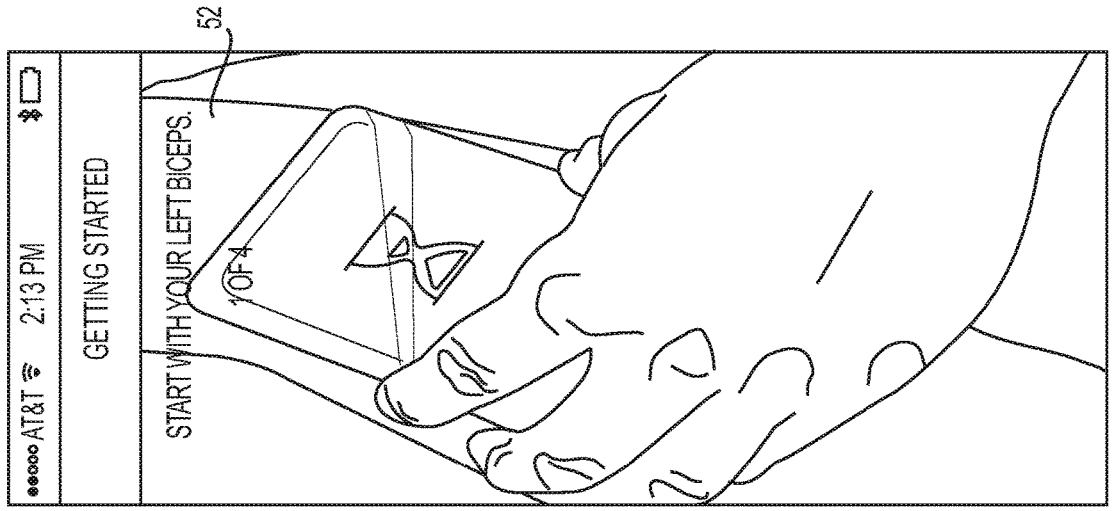
Figure 6B:
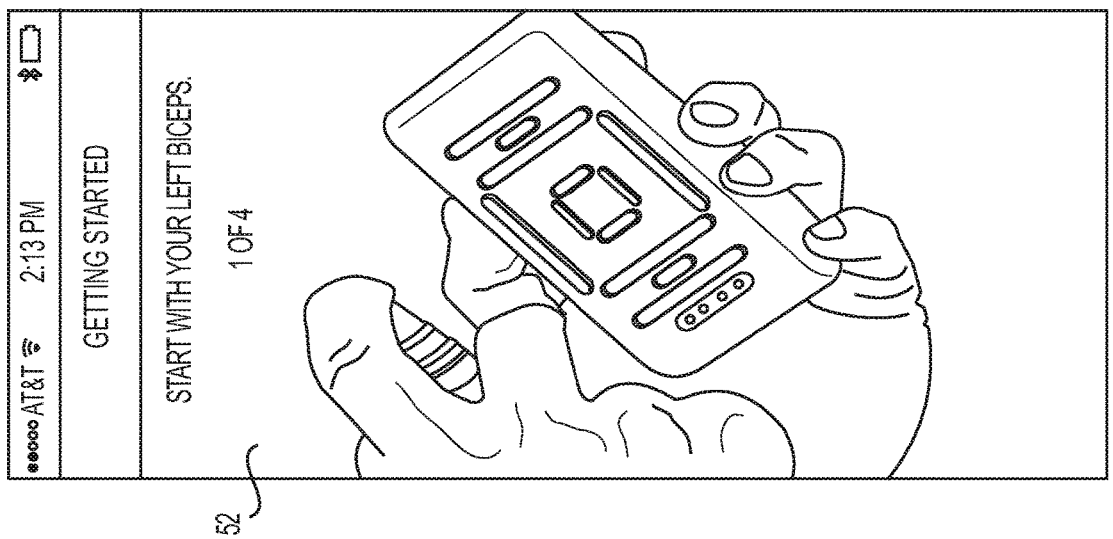
Figure 6E:
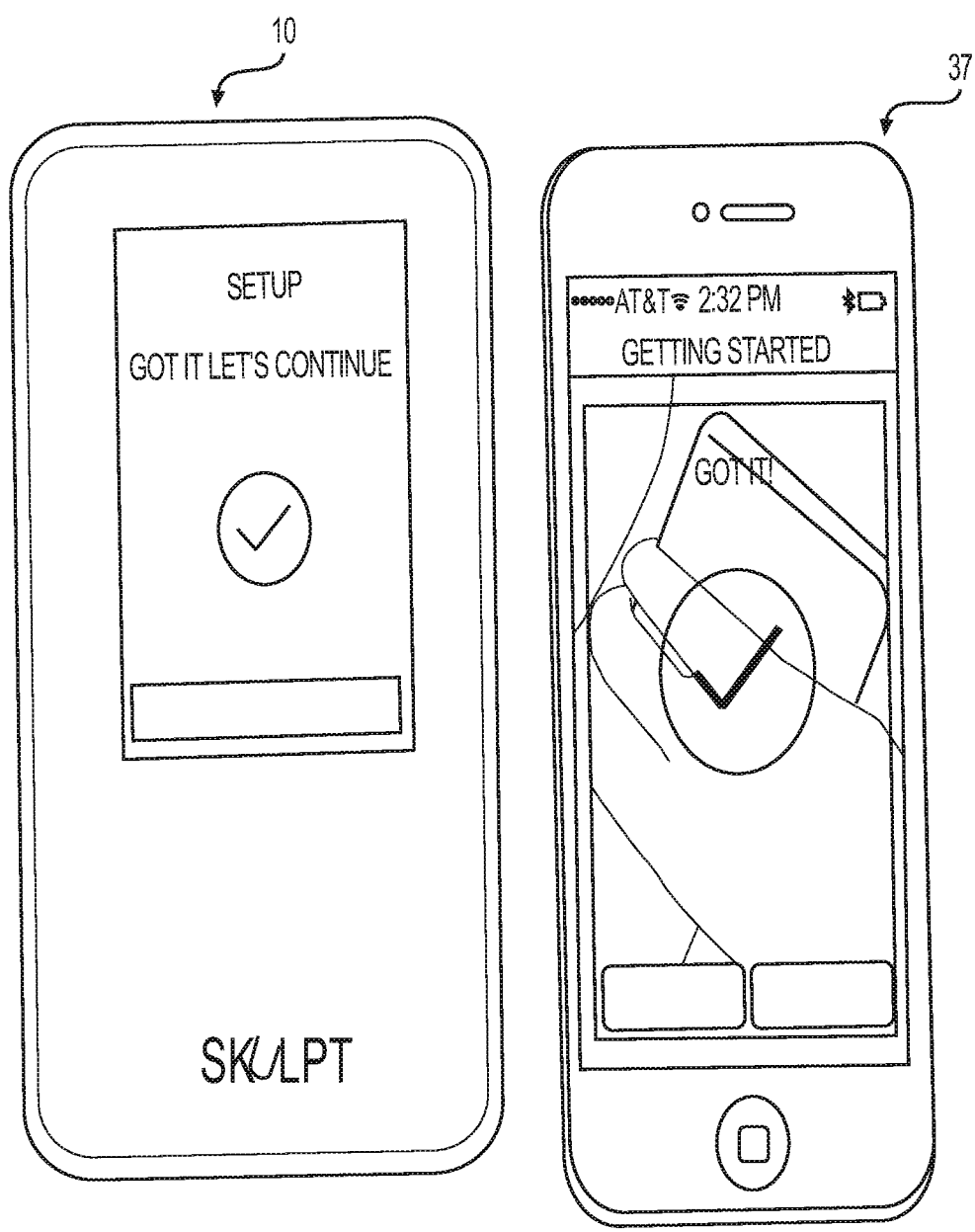
Figure 6F:
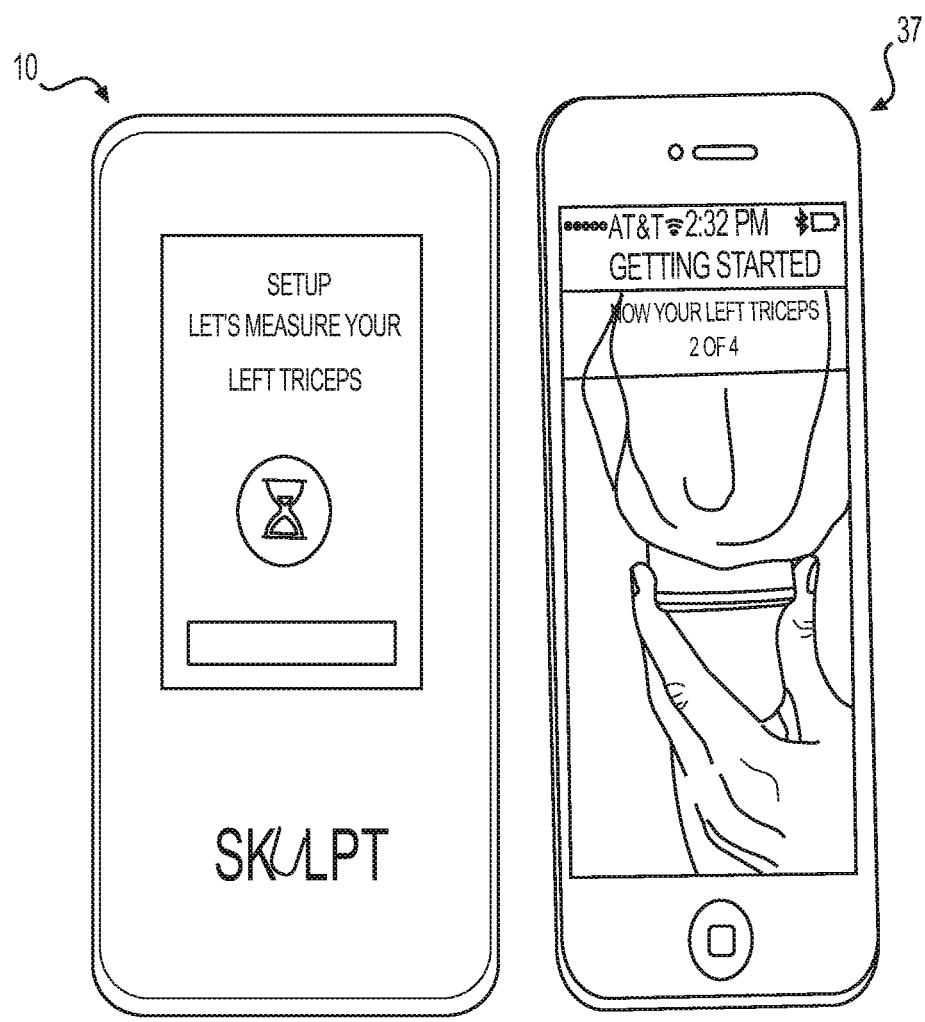
Figure 6G:
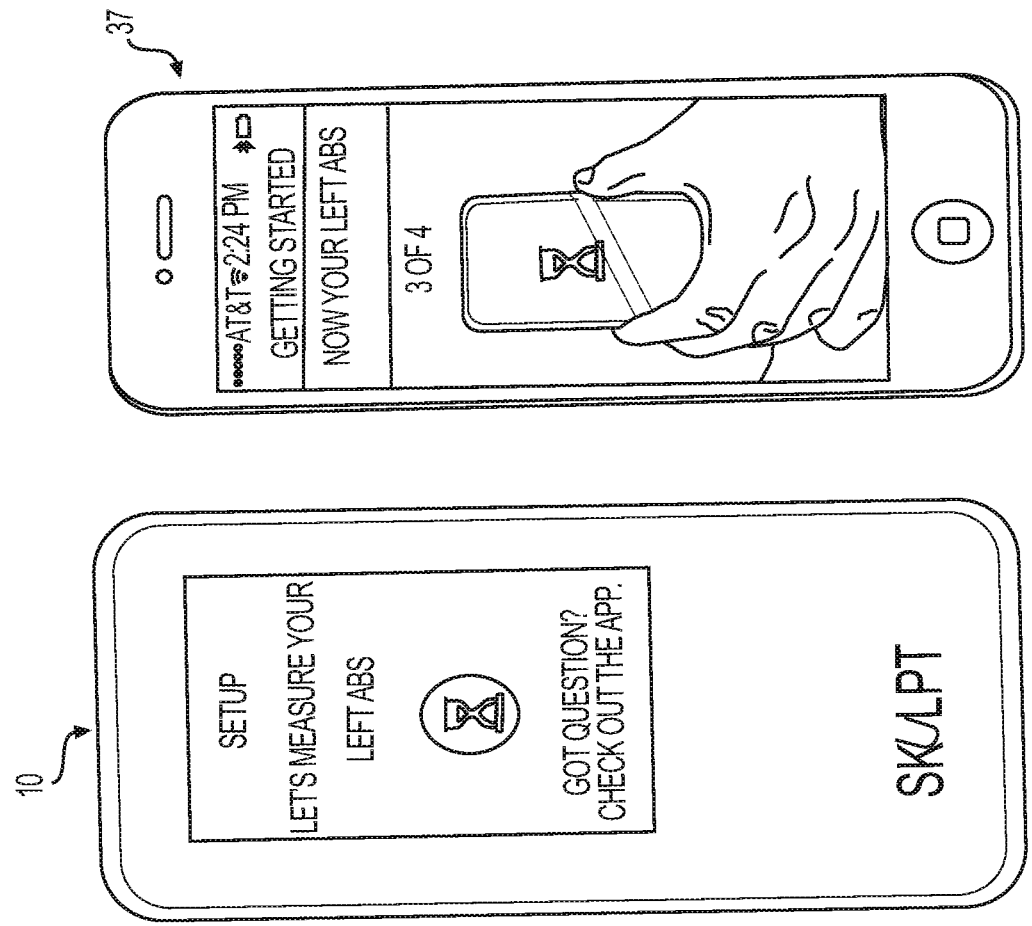
Figure 6H:
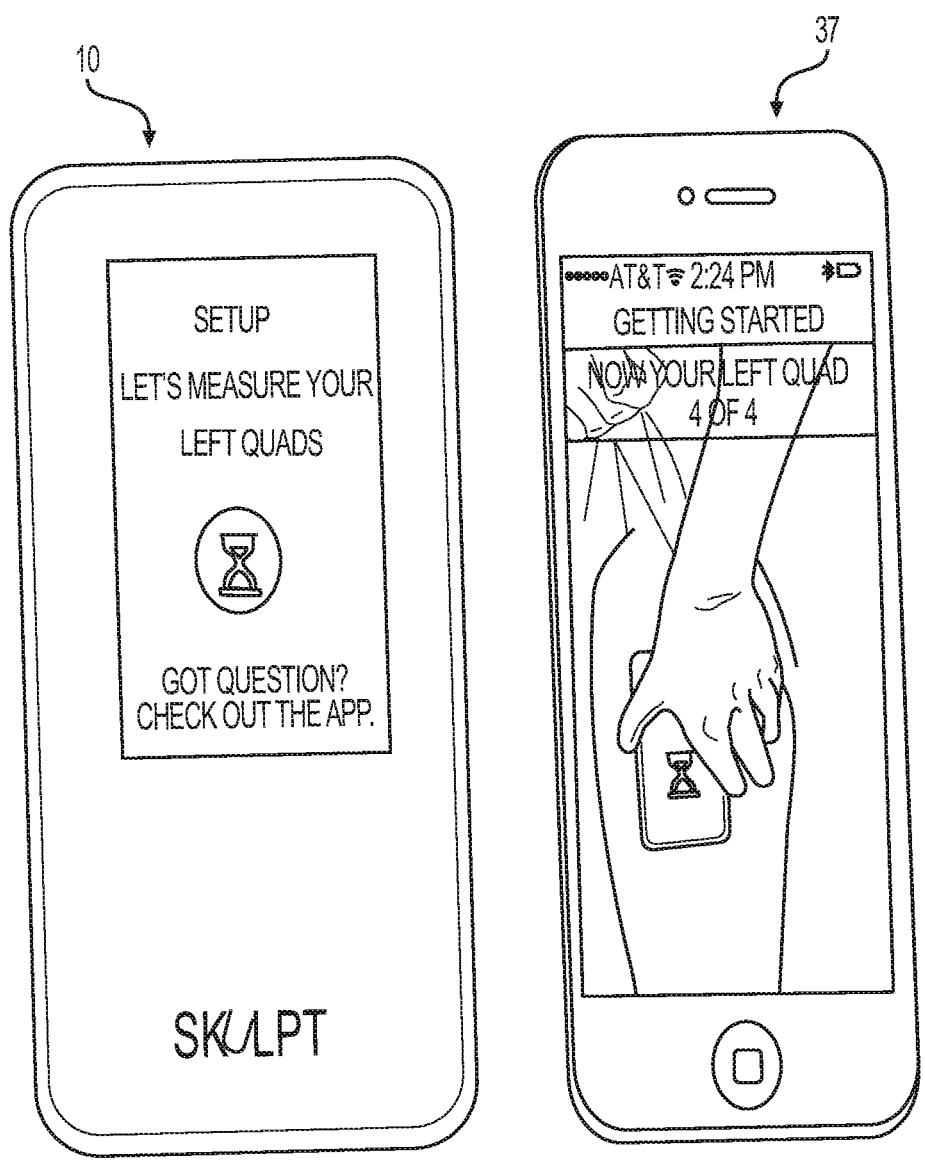
Figure 6I:
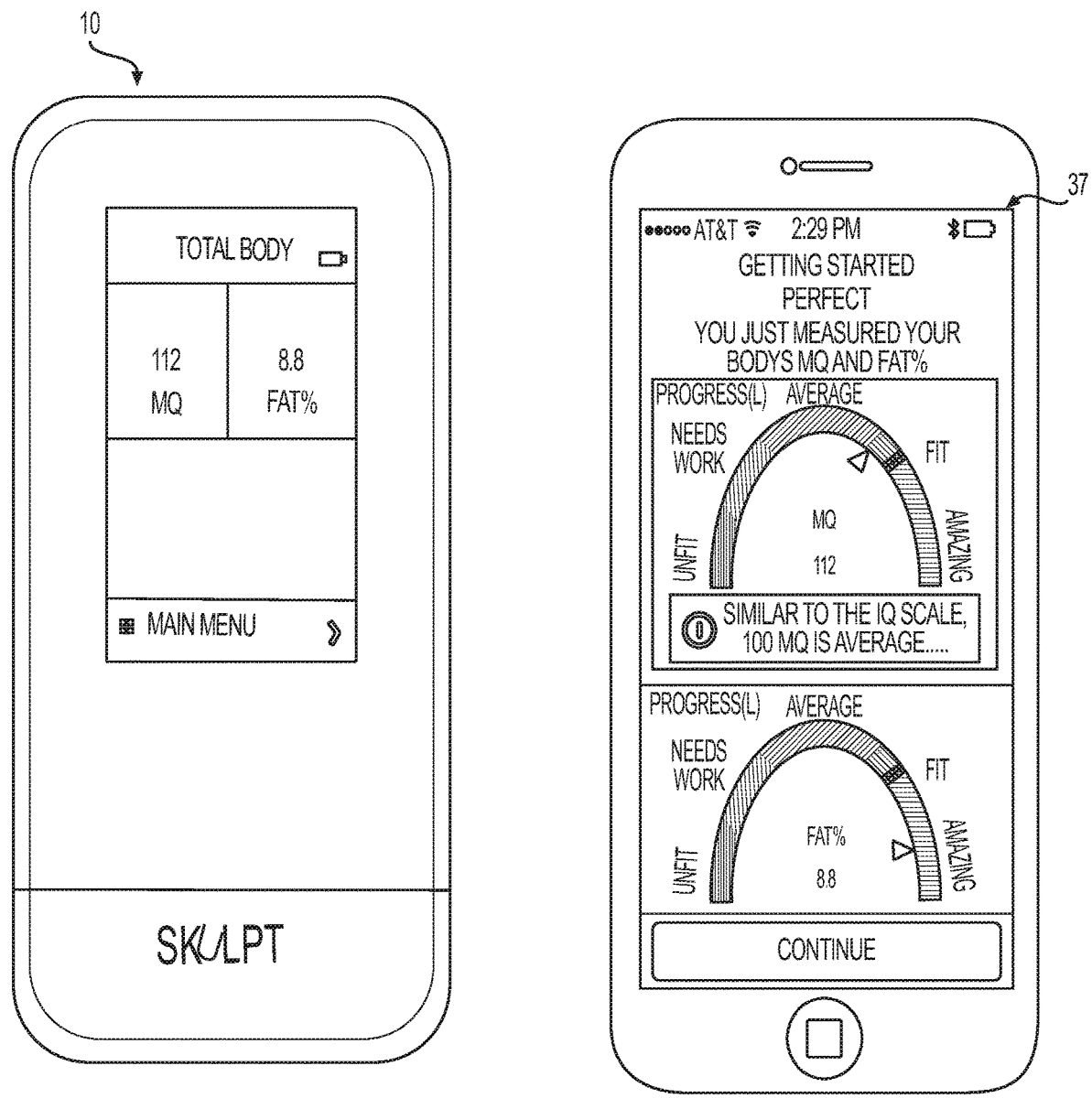
Figure 6J:
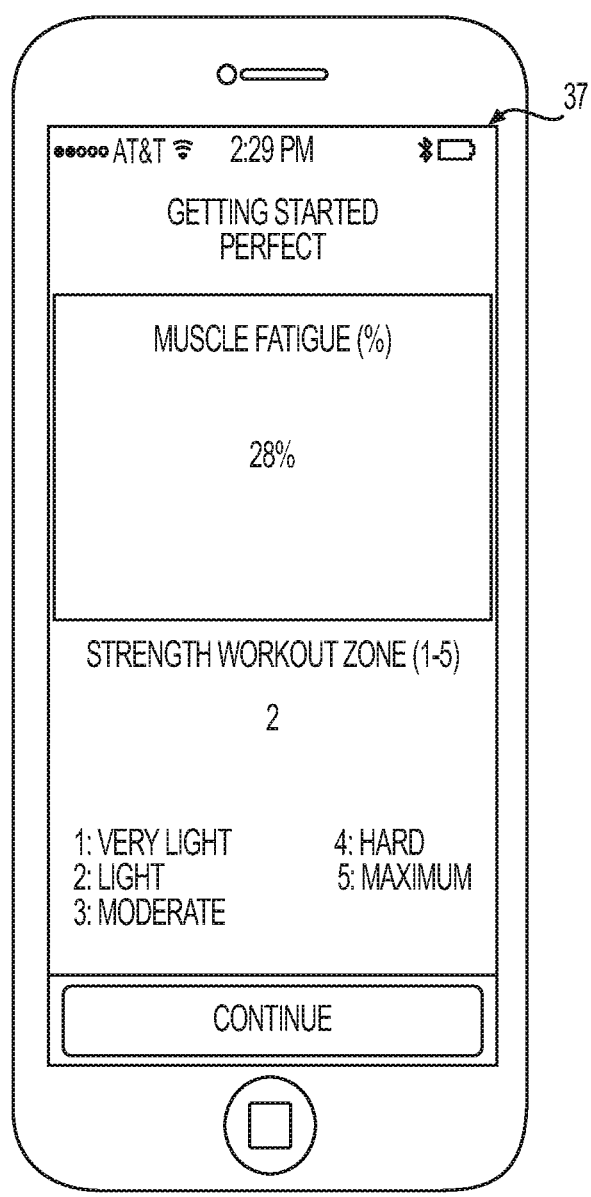

After syncing the device 10 with an associated device 37, the app 50 will now prompt the user to obtain baseline measurements at selected locations (e.g., muscle groups) of the user's body using the device 10 (see FIGS. 6A-6J). These prompts may include illustrations and detailed instructions to assist the user in obtaining the baseline measurements. For example, the app 50 may sequentially display windows with detailed instructions (including illustrations and textual information) on the display 52 of device 37 (and/or display 12 of device 10) to prompt the user to take measurements at the required locations. These instructions may include illustrations showing how to place the electrodes 18 of the device 10 at different body locations and measure the parameters at that location. Following these prompts, the user places the electrodes 18 (of device 10) against the skin at the body locations and initiates a measurement (e.g., by using a button 14 of device 10). In some aspects, the user may be prompted to apply a suitable fluid (e.g., water) to the skin prior to placement of the electrodes to improve electrode contact and conduction of electrical signals. The device 10 (and/or the associated device 37) may indicate when each measurement is successfully completed, for example, by displaying a message on its display 12 and/or by using light ring 16. The device 10 (and/or device 37) may also alert the user about an error in the measurement or setup process (e.g., when the electrodes 18 are not properly placed in contact with the skin) and/or when readings are outside of a normal or expected range. In some embodiments, the device 10 (or 37) may also provide recommendations to rectify the error (e.g., wet the skin prior to placing electrodes thereon, etc.). After the baseline measurements are complete, calculations may be performed by the device 10 and the results presented. The results may be presented in one or both of displays 12, 52 (see, e.g., FIGS. 6I, 6J). The results may include muscle quality (MQ), fat percentage, muscle fatigue percentage, and information relating to muscle strength workout zone, which is discussed below in greater detail. As shown in FIG. 6I, e.g., the results may be displayed in any suitable manner. For example, the results may be displayed as a numerical value, via a heat-map, a position on a scale (e.g., the colored or shaded rainbow scale shown in FIG. 6I), and/or via textual descriptors relating to fitness levels.

As a person of ordinary skill in the art would recognize, many variations of the above-described device and method are possible. For example, in embodiments where the device 10 does not include a display 12, the display 52 of the associated device 37 may be used to make selections (such as, selections for setup, etc.) and review results. Upon initiation of a measurement (through the device 10 or the associated device 37), the device 10 may take the measurements, perform the required calculations, and transmit the results to the associated device 37 for the user to review. Similarly, many variations of the described exemplary setup procedure are possible. In general, any setup process may be used to configure the device 10 using an associated device 37. It is also contemplated that in some embodiments, the entire setup process may be conducted using the device 10 without using an associated device 37.

Figure 7C:
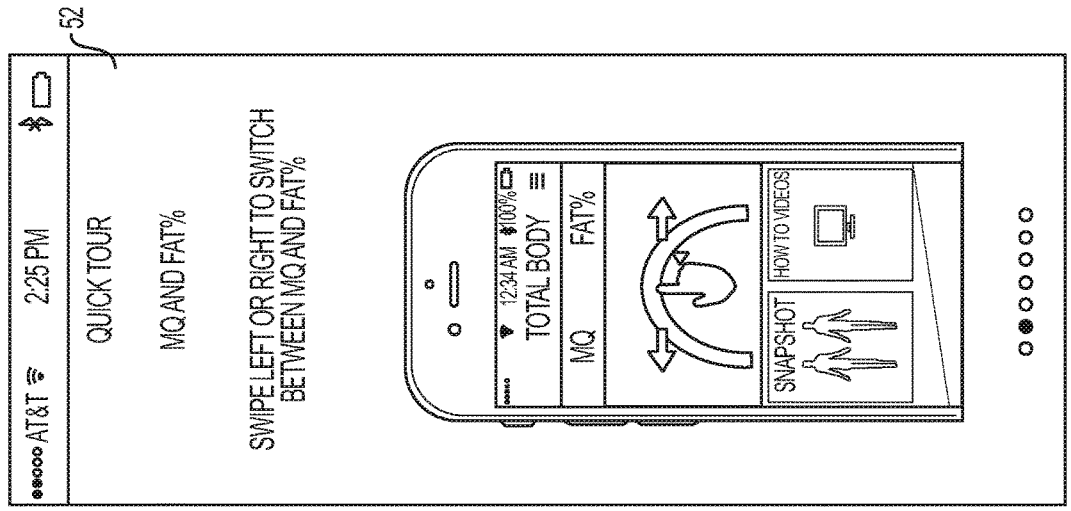
FIGS. 7A-7I illustrate an exemplary process of reviewing tutorials on the associated device.
Figure 7B:
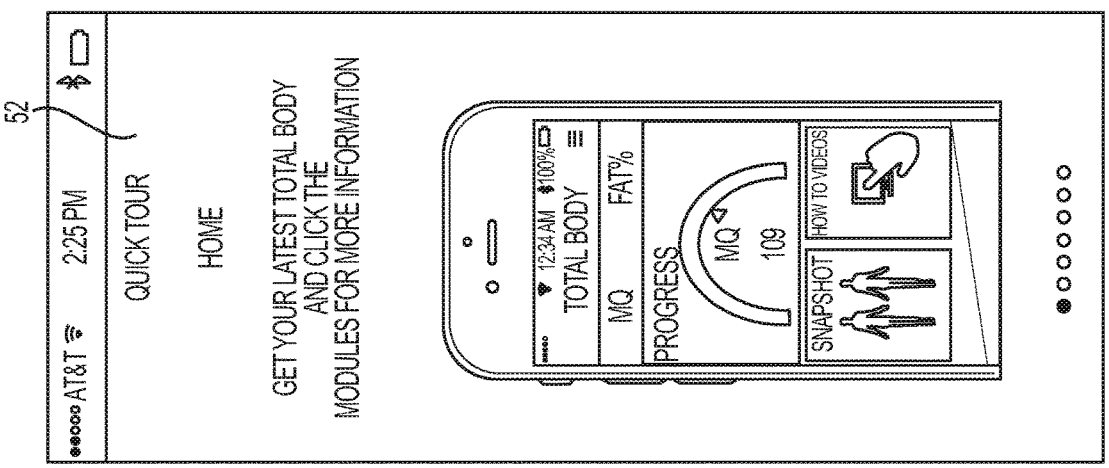
Figure 7A:
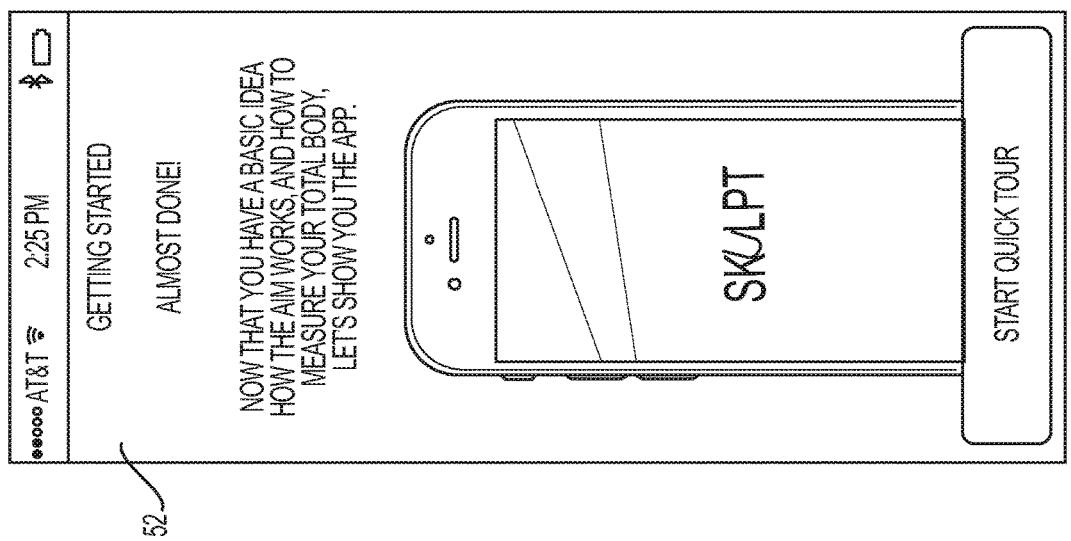
Figures 7D, 7E, 7F:
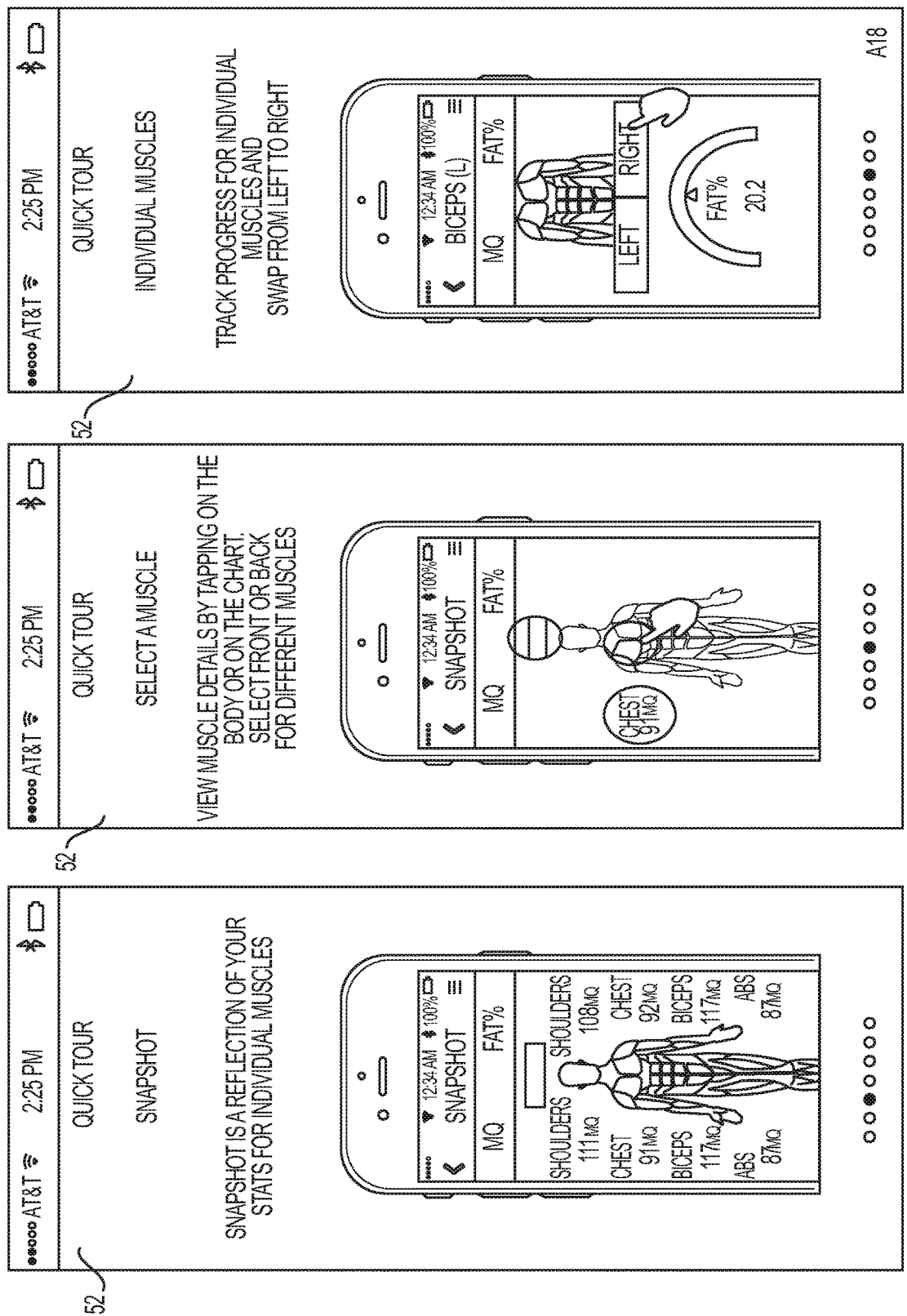
Figure 7G:
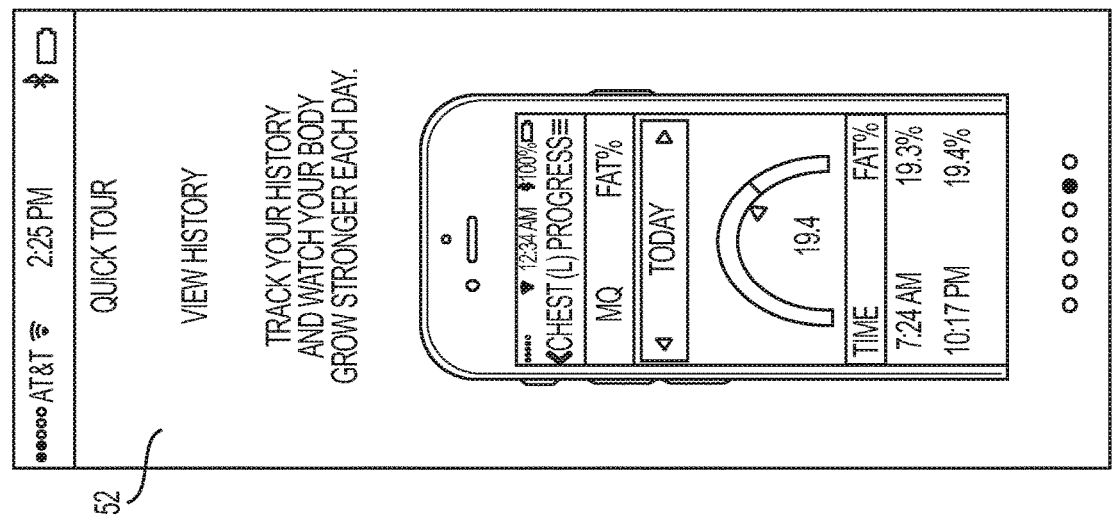
Figure 7H:
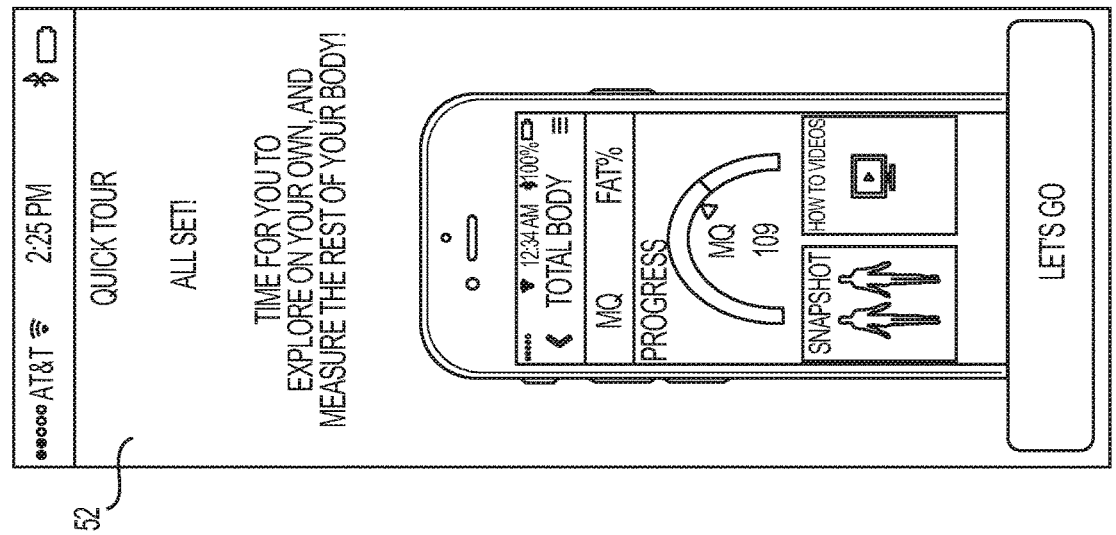
Figure 7I:
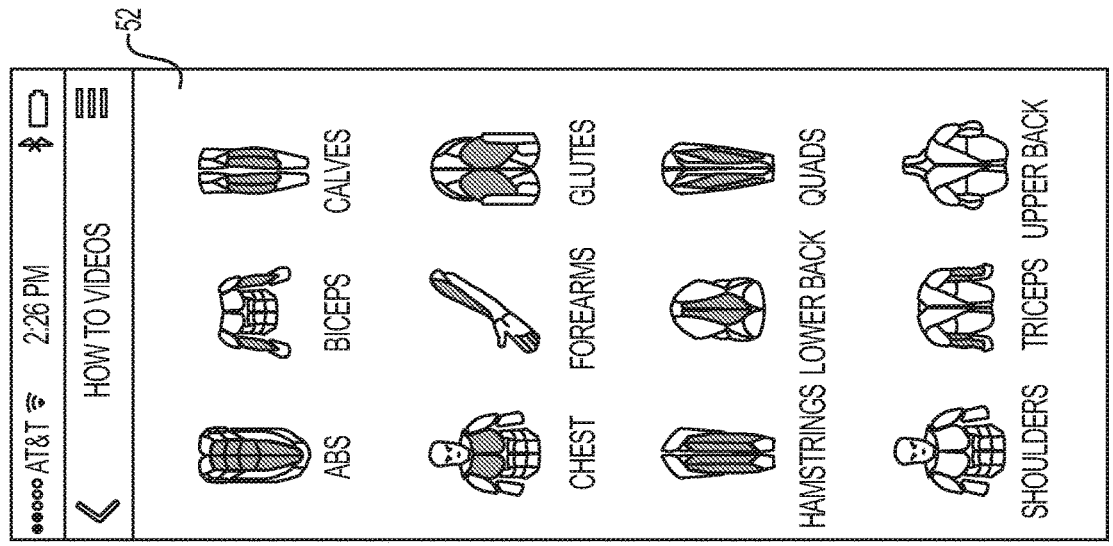
Figure 8E:
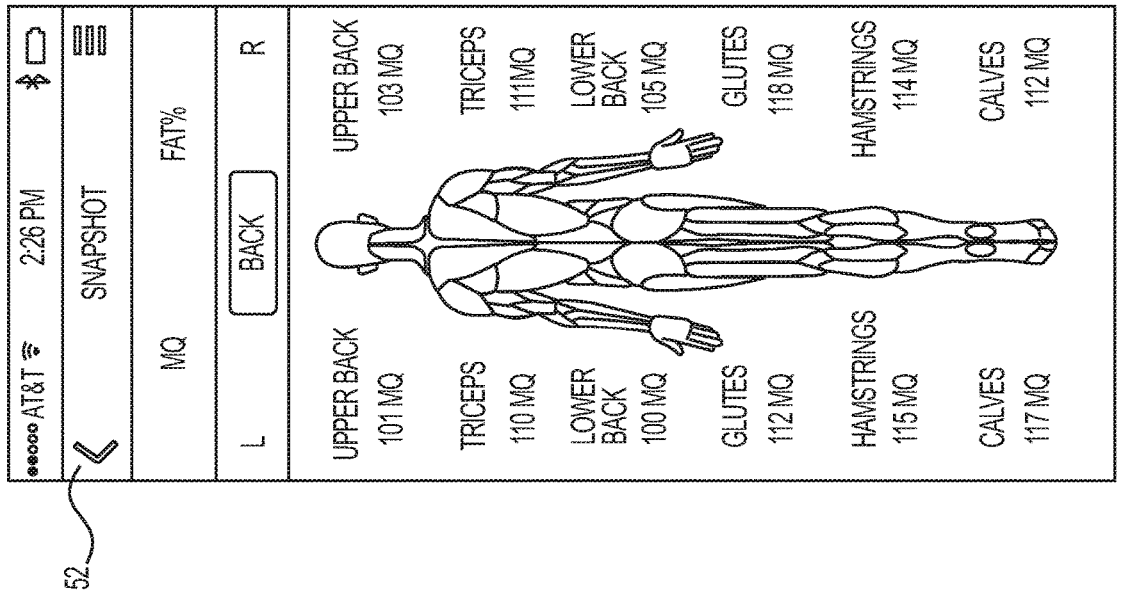
Figure 8D:
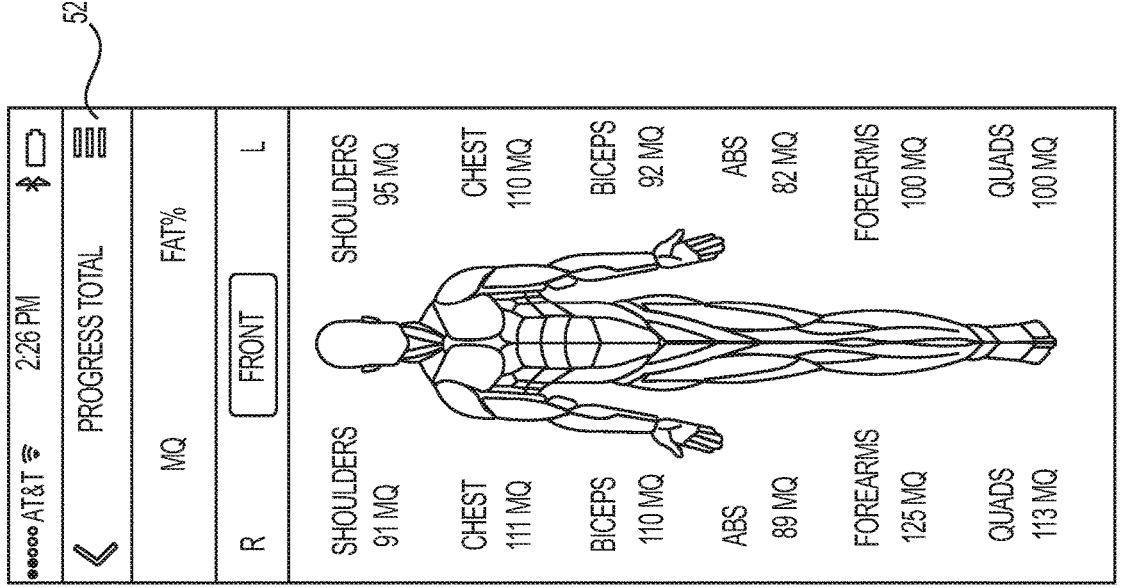
Figure 8F:
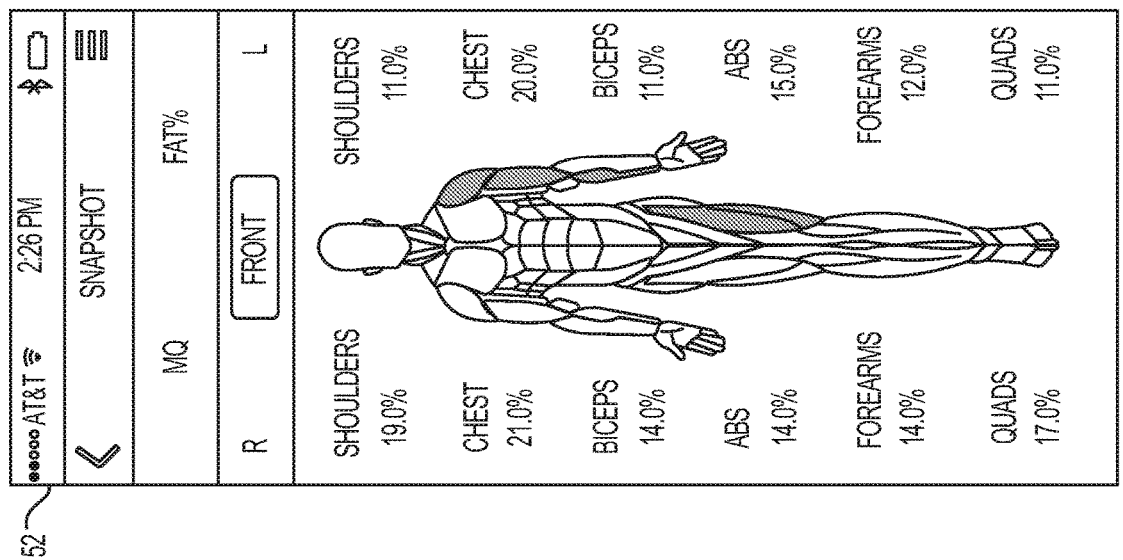

The app 50 may also include tutorials to teach the functionalities of device 10 (see FIGS. 7A-7I). The tutorial guides the user through a plurality of windows that assists the user in using the device 10 and reviewing results. For example, the tutorial may provide detailed information on the health-related parameters (e.g., MQ, FAT percentage, Muscle Fatigue percentage, Strength Workout Zones, etc.) that are computed by the device 10, how to view each of them, and how to switch between different available health-related parameters (see FIGS. 7B-7C). The tutorial may also instruct the user on different formats for viewing the results (e.g., a snapshot of results for all the measured muscles, results of individual muscles, etc.) (see FIGS. 7D-7F), and tracking the change in results over time (see FIGS. 7G-7H). The app 50 may also include detailed information (e.g., instructional videos) on how to improve the health of different muscle groups (FIG. 7I). By selecting a video, the user may be provided with information on how to improve the health of the selected muscle (e.g., suggested exercises, nutritional guidelines, etc.). In some embodiments, clicking on the image of a muscle illustrated on the display 52 may open a link to a website to access third-party information (e.g., third-party companies or information sites) that provides recommendations on how to improve the health of the selected muscle.

Figure 9B:
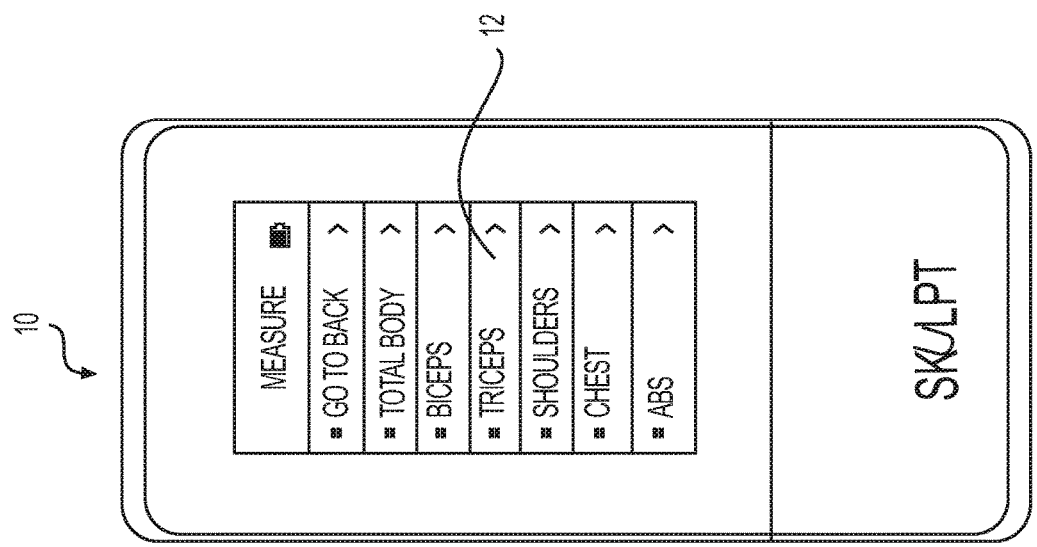
Figure 9A:
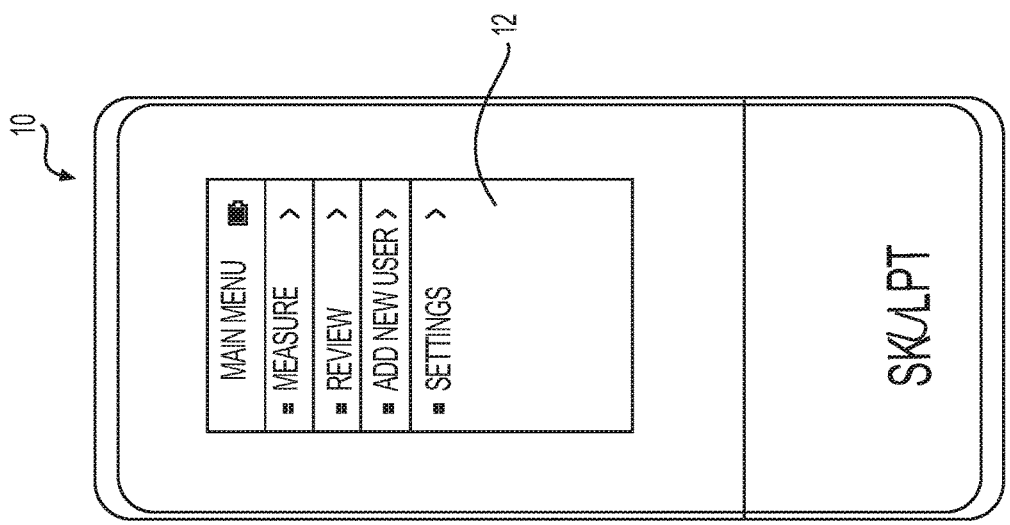
Figure 9F:
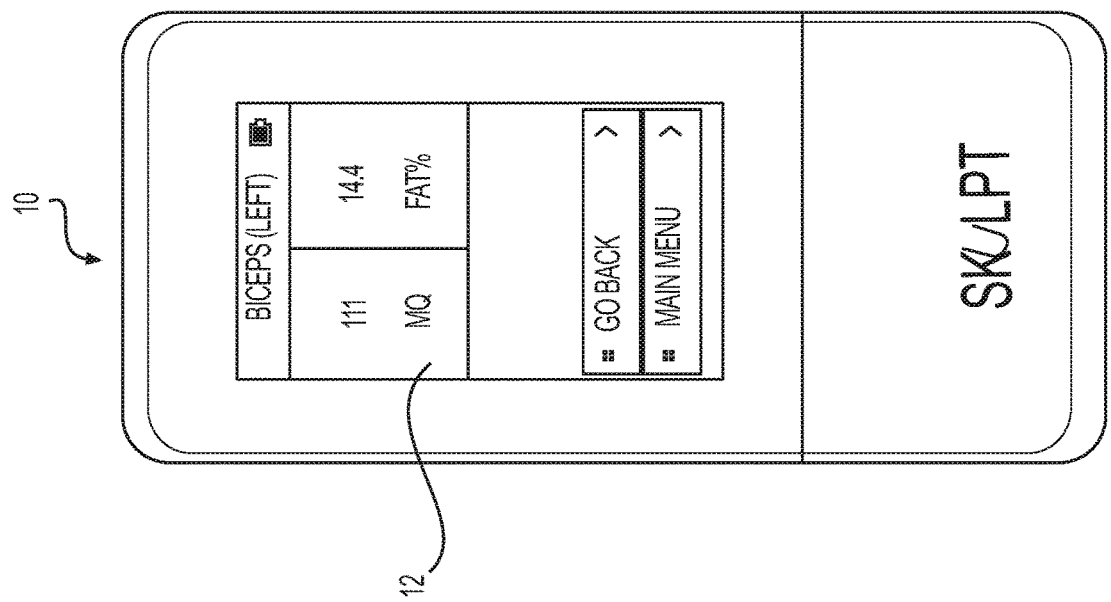
Figure 9E:
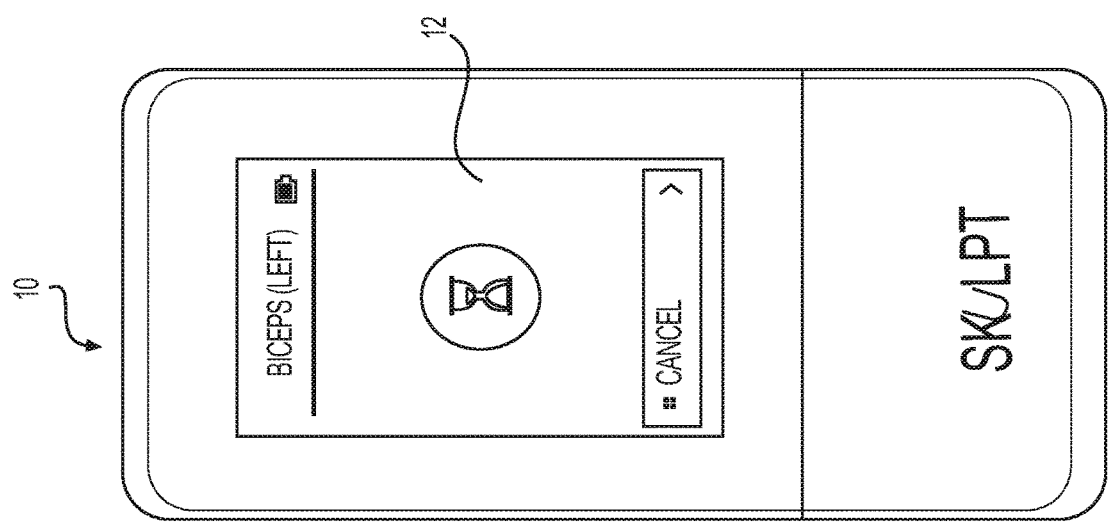

After setting up an account, the user may login to the account at any time to select and view the results from any measurement (see FIGS. 8A-8E). It should be noted that the representation of the results illustrated in these figures are only exemplary. In general, the results may be presented in any manner (table of results, line graphs, bar graphs, etc.). Although reviewing the results and instructions on display 52 of the associated device 37 is described above, the results and instructions may also be viewed on the device 10 (see FIGS. 9A-9F). By selecting (e.g., using a button 14 or by touching the screen) the appropriate tab displayed on display 12 of the device 10, the user may select a result for display (see FIG. 9F). Although FIG. 9F illustrates a textual display of results, the results may be displayed in any manner (pictorially, graphically, etc.).

Multiple users may share a device 10. Each user may be able to create an account that can be used to store and access that user's data separate from other data. Measured and calculated user data may be stored in one or more of the device 10, the associated device 37, or a remote computer 40. A user may be able to select the user for whom measurements will be made. After selecting the user, the selected user's data can be collected, results calculated and presented. In some embodiments, each user may be distinguished by display color (font or any other indicator). For instance, when a first user is selected, the color of the display (or text, etc.) may be, for example, blue, and when a second user is selected, the color of the display/text may be, for example, red. The data of each user may be protected by a password. In some embodiments, groups of users may be created using device 10 or 37. Individual users in a group may be able to compare their data and results with other users in the group. The comparison data may be presented in device 10 or 37. Individual users may be able to create groups, join groups and leave groups. Alternatively, users can be assigned to groups by a third party. In some applications, user groups may formed as teams for competition and awards (or electronic badges) awarded based on improvements in performance or any other metric. Such competitions may be coordinated by, and awards presented by, a user in the group or a third-party. In some embodiments, the device 10 may have the capability to store measurements and data of one or more users when not in communication with the associated device 37, and then transmit the data to the associated device 37 when communication is restored.

In some embodiments, device 10 and/or the associated device 37 may be configured to share information with third-party software (e.g., health-tracking software such as HealthKit). For example, app 50 may include an API (Application Programming Interface) the enables third-party software to access measured data and/or computed results from device 10 and/or 37. The device 10 and/or associated device 37 may also be configured to access and/or receive data from third-party software. For example, data related to the health of the user (e.g., ECG, heart rate, pedometer data, calories burned, etc.) that were recorded by third-party devices (iPhone®, Fitbit®, etc.) or health-tracking software may be accessed by (or received) by device 10 or 37. In some embodiments, the data measured by device 10 and the received data may be used to compile a holistic health report of the user or create an exercise plan or regimen.

FIG. 10A illustrates an exemplary pattern of the electrodes 18 on the backside of device 10. Electrodes 18 may include any electrically conductive material (e.g., copper, aluminum, silver, gold, etc.). In some embodiments, the electrodes 18 may be coated with (or treated with) another material to impart desirable properties to the electrodes 18 (e.g., oxidation, wear, and/or corrosion resistance, decreased interfacial contact resistance, etc.). In some embodiments, the electrodes 18 may protrude from the surface of the device 10 on which they are positioned. In some embodiments, the electrodes 18 may be flush with, or recessed relative to, the surface. The electrodes 18 may include multiple conductive elements 20 arranged in a pattern. In some embodiments, twelve conductive elements 20 may be arranged in a pattern to allow different configurations to be used in a measurement. In general, the conductive elements 20 may be arranged in any desired pattern. In some embodiments, the conductive elements 20 may be arranged in a pattern about a central axis 22 of the device 10 that extends perpendicular to the surface on which the electrodes 18 are positioned. In some embodiments, electrodes 18 may include a plurality of conductive elements 20 spaced apart and arranged along a first axis 24 and a plurality of conductive elements 20 spaced apart and arranged along a second axis 26 perpendicular to the first axis 14. In some embodiments, the conductive elements arranged along the first axis 24 may be symmetrically positioned about the second axis 26, and the conductive elements 20 arranged along the second axis 26 may be symmetrically positioned about the first axis 24. In some embodiments, the conductive elements 20 may be symmetric about both the first and second axes 24, 26.

In some embodiments, as illustrated in FIG. 10A, four conductive elements (20i, 20j, 20k, 20l) may be arranged to form the four sides of an inner square. These four conducive elements may have substantially the same length. In some embodiments, four additional conductive elements (20c, 20d, 20g, 20h) may be arranged to form the four sides of an outer square positioned radially outwards of the inner square. These four conductive elements may have a longer length than the conductive elements that comprise the inner square. Additional conductive elements (20a, 20b, 20e, 20f) having any length may be disposed outside the outer square. In some embodiments, some of these additional conductive elements may have substantially the same length as the conductive elements of the inner square and the remaining conductive elements may have substantially the same length as the conductive elements of the outer square. In some embodiments, one or more conductive elements of a shorter relative length and one or more conductive elements of a larger relative length may be disposed parallel to the conductive elements that make up two opposite sides of the outer square.

Figure 10C:
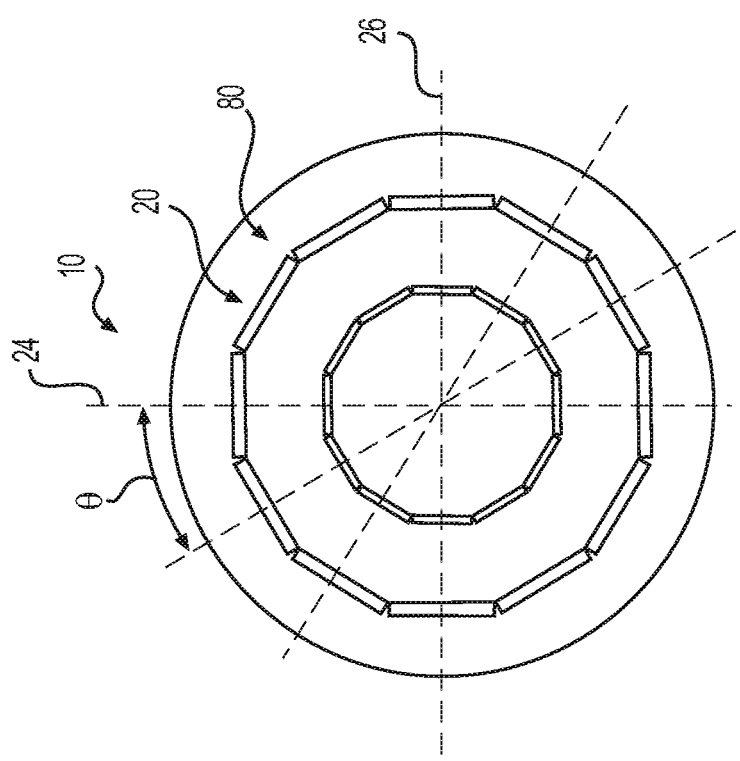

FIGS. 10B and 10C illustrate some other possible arrangement patterns of electrodes 18. In both these embodiments, the plurality of conductive elements 20 are spaced apart and arranged symmetrically about the first and second axes 24, 26. In contrast to the embodiment of FIG. 10A, in the embodiments of FIGS. 10B and 10C, the number of conductive elements positioned along the first axis 24 is the same as the number of conductive elements arranged along the second axis 26. In some embodiments, the spacing of the conductive elements 20 along both the axes (24, 26) may also be substantially identical. In the embodiments of FIGS. 10A and 10B, the conductive elements 20 are arranged along axes (i.e., the first and second axes 24, 26) that are substantially perpendicular to each other (i.e., θ=90°). However, in the embodiment of FIG. 10C, the conductive elements 20 are arranged along axes that make an angle θ of about 30° with each other. In general, angle θ may have any value. Further, in the embodiments of FIGS. 10A and 10B, the conductive elements 20 are arranged in a substantially rectangular (or square) pattern, while in FIG. 10C, the conductive elements are arranged in a substantially circular pattern. For example, as depicted in FIG. 10C, the electrodes 18 may include conductive elements disposed in two (or any number of) concentric circles.

In some embodiments, the electrodes 18 may be oriented along an axis of the device 10, preferably along the long axis. In some embodiments, the electrodes 18 may not be oriented along an axis, but an orientation line or marker may be printed (or otherwise placed) on the device 10 to indicate to the user, the orientation of the electrodes 18. The user may use this marker to align the electrodes while taking a measurement. In some embodiments, to take a measurement, the device 10 may be positioned, with the electrodes 18 in contact with the tissue, over the muscle to be measured such that the orientation marker (or the long axis in embodiments where the electrodes are oriented along the long axis) is roughly oriented with the muscle fibers to be measured. By "roughly oriented," it is intended that the user positions the device 10 by eye and feel such that the electrodes are generally oriented with the muscle fibers. Experiments have indicated that it is not necessary to align the device more accurately (e.g., by using a measuring device or other precise locator).

In one exemplary application, to make measurements at each muscle group, the electrodes 18 (or orientation marker) of device 10 are aligned as described below. Biceps— Oriented along arm bone; Triceps—Oriented along arm bone (between shoulder bone and elbow); Abs (or Waist)— Oriented in front of body roughly parallel to (and in some cases, laterally offset from) the backbone (the edge of the device is placed about 1 cm to the left or right of the navel with the vertical center of the device roughly aligned with the navel. The long side of the device may be aligned with the torso); Quads—Oriented along leg bone; Shoulder—

Oriented along the arm bone; Inner Forearm/wrist flexor—Oriented along forearm bone; Outer Forearm/wrist extensor—Oriented along forearm bone; Chest—Oriented roughly parallel to the torso (for men, middle of device is positioned over nipple, and for women, the bottom of the device is positioned about 1 cm above the nipple and the long axis of the device is roughly co-linear with the nipple and parallel to the torso); Upper Back—Oriented roughly parallel to the spine with the top of the device about 1 cm below the shoulder blade and the side of the device about 1 cm to the side of the spine such that none of the electrodes are directly over the spine; Lower Back—Oriented parallel to the spine with the bottom of the device about 1 cm above the waist line and the side of the device about 1 cm to the side of the spine such that none of the electrodes are directly over the spine; Hamstrings—Oriented along a long leg bone, half way between the bend of the leg opposite the knee and the gluteal fold; Calves (gastrocnemius)—Oriented along leg bone; Glutes—Oriented parallel to the leg bone with the edge of the sensor about 2 cm from the intergluteal cleft; Calf—Oriented along leg bone; Hip—Oriented roughly diagonally about 2 cm above the hipbone (the angle of the sensor may be about the same angle as the hipbone); Thigh—Oriented along leg bone. However, it should be noted the above described alignment is only exemplary and the device 10 may be positioned over the muscle in any manner.

To take a measurement at a region of a user's body, all the conductive elements 20 of the electrodes 18 are positioned in contact with the region. The conductive elements 20 are arranged at different distances and orientations to each other to make measurements using multiple electrode configurations. Each electrode configuration is composed of a pair of conductive elements 20 (current elements) to direct an alternating current through the body, and a pair of conductive elements 20 (voltage elements) to measure the voltage across them. The table below shows some of the exemplary electrode configurations (with reference to FIG. 10A) that may be used in a measurement. These configurations are described in further detail and referred to below.

TABLE 1

Electrode pairs in exemplary configurations

| | Current electrodes | Voltage electrodes |
|---|---|---|
| Configuration 1 | 20a and 20f | 20b and 20e |
| Configuration 2 | 20a and 20f | 20j and 20l |
| Configuration 3 | 20c and 20d | 20j and 20l |
| Configuration 4 | 20g and 20h | 20i and 20k |

For example, in configuration 1, conductive elements 20a and 20f may be used to apply an alternating current through the body and conductive elements 20b and 20e may be used to measure the differential voltage across them. In general, any pair of current elements may combine with another pair of voltage elements to form a configuration. Although only four configurations are listed in the table above, other configurations are also contemplated. In some embodiments, each current element (20a, 20f, 20g, 20h, etc.) of a configuration may be wider than each voltage element (20b, 20e, 20i, 20k, etc.) of the configuration. In some embodiments, each voltage element pair of a configuration (e.g., 20b, 20e of configuration 1) may be positioned radially inwards of the current element pair of the configuration (20a, 20f). The alternating current directed through a current element pair is typically between about 5 micro-amps and about 500 micro-amps at a frequency between about 1 kHz and about 1 MHz, and the voltage measured across each voltage element pair is typically between about 500 microvolts and 50 millivolts. Although current and voltage electrode pairs are only described with reference to the electrode pattern of FIG. 10A, using the concepts described herein, a person of ordinary skill in the art will be able to identify the current and voltage electrode pairs in the electrode patterns of FIGS. 10B and 10C as well.

In some embodiments, when device 10 is used to take a measurement of a region, the device may take voltage measurements using multiple different configurations of electrodes 18 at multiple frequencies. That is, in some embodiments, in a single measurement, the device 10 may take voltage measurements using the above-described configurations 1, 2, 3, and 4 at different frequencies of current (e.g., 25 KHz, 50 KHz, 100 KHz, 200 KHz, etc.) before indicating that the measurement is complete. In some embodiments, the device 10 may take measurements of some (but not all) of the configurations (e.g., configurations 1 and 2). In some embodiments, the device 10 may take measurements in only one configuration (e.g., configuration 1) before indicating that the measurement is complete. In some embodiments, the number of configurations to use may be selected before a measurement is initiated. The measurements in the multiple configurations may be taken simultaneously or sequentially.

The purpose of using multiple electrode configurations is that, depending on the distances and orientations between the conductive elements 20, a particular configuration may yield bioimpedance parameters that correlate better with physiological characteristics of interest. For example, in the embodiment of electrodes 18 illustrated in FIG. 10A, the distance between conductive elements 20a and 20b (and conductive elements 20f and 20e) is about 0.3 inches (7.62 mm) and the distance between conductive elements 20a and 20j (and conductive elements 20f and 20l) is about 1.17 inches (29.72 mm). It has been observed that bioimpedence measurements using a configuration (such as configuration 1) in which the voltage elements (such as electrodes 20b and 20e) are closer to the current elements (such as 20a and 20f) correlate strongly with subcutaneous skin fat thickness. In contrast, placing the voltage electrodes farther from the current electrodes (e.g., configuration 2 with conductive elements 20a and 2f as the current elements and conductive elements 20j and 20l as the voltage elements) results in measurements of bioimpedance that are less sensitive to subcutaneous fat and more sensitive to muscle quality, fatigue, recovery, health, and fitness.

Figure 11:
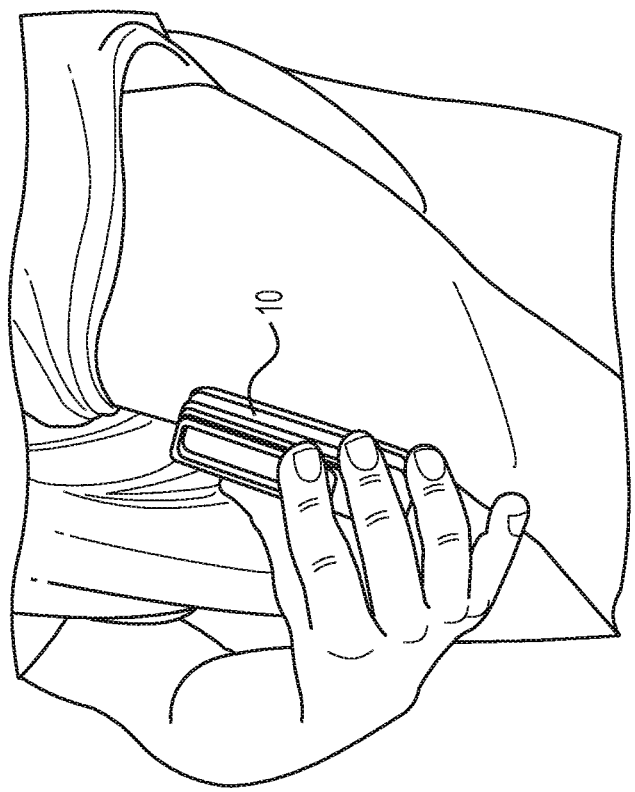
FIG. 11 illustrates the device of FIG. 2 being used to take measurements on a muscle, such as, e.g., the bicep of a user.

Without intending to be limiting, an exemplary measurement of parameters 35 related to bioimpedance of a biceps using device 10 is described below. In this exemplary measurement, the four electrode configurations listed in Table 1 above (i.e., configurations 1, 2, 3, and 4) and four discrete frequencies are used for the measurements. The four current frequencies used may include 25 KHz, 50 KHz, 100 KHz, and 200 KHz, respectively. Those of ordinary skill will recognize that these frequencies are exemplary and that any suitable magnitude and number of frequencies may be used with any electrode configuration. As illustrated in FIG. 11, the device 10 may be positioned on the bicep of the user with the electrodes 18 in contact with the skin of the bicep. The light ring 16 (or the display 52 of the associated device 37) may indicate when good contact is made with the skin. Measurement may then be initiated by depressing a button 14 (or using device 37). The device 10 may measure bioimpedance data (e.g., impedance, resistance, phase angle, etc.) using the four electrode configurations at the four different frequencies and indicate that the measurement is complete.

Using the measured data, several health parameters 35 related to tissue health may be determined. These health parameters 35 may include parameters related to the percentage of fat and muscle at the measured location (biceps in this example) and parameters related to overall muscle quality at that location. In some embodiments, these parameters may include simple biceps fat percentage, biceps fat percentage, biceps muscle percentage, biceps muscle quality, modified biceps muscle quality, biceps muscle fatigue, and biceps strength workout zone. These health parameters 35 may be determined as a function of the measured data (resistance, phase angle, etc.) at some or all of the frequencies at some or all of the electrode configurations. For example, in some embodiments, the parameters related to fat percentage (such as, simple biceps fat percentage and biceps fat percentage) may be calculated as a function of the measured resistance at multiple current frequencies using the same electrode configuration, and the parameters related to muscle percentage (such as, bicep muscle percentage) may be calculated as a function of the measured phase angle at the same current frequency at multiple electrode configurations. And, the parameters related to muscle quality may be calculated as a function of the ratio of the muscle percentage to the fat percentage. In some embodiments, muscle quality may not be calculated as a ratio of muscle percentage to fat percentage. Instead, muscle quality may be calculated directly from measured impedance values.

In some embodiments, simple biceps fat percentage, biceps fat percentage, biceps muscle percentage, biceps muscle quality, and modified biceps muscle quality may be measured using the equations presented below. Simple Biceps Fat Percentage=0.35/ohms×({Biceps resistance at configuration 1 at 50 kHz}+{Biceps Resistance at configuration 1 at 100 kHz}+{Biceps Resistance at configuration 1 at 200 kHz}); Biceps Fat Percentage=100×tanh (0.0036× [{Biceps Resistance at configuration 1 at 50 kHz}+{Biceps Resistance at configuration 1 at 100 kHz}+{Biceps Resistance at configuration 1 at 200 kHz})]; Biceps Muscle Percentage=100×tanh (0.025×{Biceps Phase at configuration 1 at 50 kHz}×({Biceps Phase at configuration 3 at 50 kHz}/{Biceps Phase at configuration 4 at 50 kHz}). The Bicep Muscle Quality may then be determined as 100×tanh (Biceps Muscle Percentage/Biceps Fat Percentage/4.5), and modified Biceps Muscle Quality may be computed as Biceps Muscle Quality+2.1×Gender+0.1×weight/height$^2$ using 1 for males and 0 for females for the constant "Gender."

The above described equations and configurations are only exemplary. In general, good measures of fat percentage may be obtained using a single electrode configuration and good measures of MQ may be obtained using one or two electrode configurations. In some embodiments, only a single electrode configuration (e.g., configuration 2 of Table 1) may be used for measurement of individual muscles. In some embodiments, the most suitable configurations for individual muscles and total body MQ measurements may be configurations 2 and 3 of Table 1.

In some embodiments, fat percentage and MQ may be calculated using the equations below. Fat Percentage= R50C1−7; MQ=M(k1*P100C1^2+k2*P50C3^2+(k3/R25C1)^2+(k4/R50C1)^2+(k5/R100C1)^2+(k6/R200C1)^2)^0.5+N. Where P100C1, for example, means phase at 100 kHz using configuration 1, P50C3 means phase at 50 kHz using configuration 3, R25C1 means resistance at 25 kHz using configuration 1, R50C1 means resistance at 50 kHz using configuration 1, R100C1 means resistance at 100 kHz using configuration 1, R200C1 means resistance at 200 kHz using configuration 1, etc. In the equation for MQ, the following constants and parameters may be used: M=1.1, k1=3.6, k2=3.4, k3=480, k4=720, k5=240, k6=240. And, the following values may be used for N depending upon specific muscle or body part. Biceps N: 30, Triceps N: 35, Shoulders N: 30, Forearms N: 30, Chest N: 30, Abs N: 55, Thighs N: 45, Hamstrings N: 30, Calves N: 30, Gluteus Maximus N: 30, Lower Back N: 30, and Upper Back N: 30. In some embodiments, gender specific values may be used for N in the equations above.

In some embodiments, additional health parameters 35 also may be calculated using the measured data. These health parameters may include parameters related to muscle status and muscle fatigue. In some embodiments, these parameters may be calculated using the formulas presented below (for biceps). Biceps Muscle Status=100×tanh (Biceps Muscle Phase at 25 kHz using configuration 1−Biceps Muscle Phase at 25 kHz using configuration 2); Modified Biceps Muscle Status=Biceps Muscle Status+2.1×Gender+ 0.1×weight/height$^2$; Biceps Muscle Fatigue=Biceps Muscle Status at baseline−Biceps Muscle Status at current time; Biceps Muscle Fatigue as Percentage=(Biceps Muscle Status at baseline−Biceps Muscle Status at current time)/(Biceps Muscle Status at baseline)×100%. In these formulas, 1 is used for males and 0 for females for the constant "Gender."

In some embodiments, Biceps Strength Workout Zone may be calculated based on the description below:

Biceps Strength Workout Zone=1 if Biceps Muscle Fatigue is between 0% and 20%; Biceps Strength Workout Zone=2 if Biceps Muscle Fatigue is between 20% and 40%; Biceps Strength Workout Zone=3 if Biceps Muscle Fatigue is between 40% and 60%; Biceps Strength Workout Zone=4 if Biceps Muscle Fatigue is between 60% and 80%; Biceps Strength Workout Zone=5 if Biceps Muscle Fatigue is between 80% and 100%;

The device 10 then may be moved to other locations on the body (such as, the stomach, quadriceps, scapula, etc.) and the measurements repeated in those localized regions. Using these measurements, health parameters 35 for a location may be calculated using the above-described formulas using the measured data at the location. Using the computed parameters 35 from different parts of the body, and in some cases, information from the user's profile, whole body parameters such as Total Body Fat Percentage, Total Body Muscle Percentage, and Total Body Muscle Quality may be computed in any suitable manner. For example, characteristics (e.g., Total Body Fat Percentage, Total Body Muscle Percentage, and Total Body Muscle Quality) may be calculated based upon the various localized measurements and/or localized health parameters 35 based on those measurements. In one aspect, e.g., the total body characteristics may be calculated by performing a suitable statistical calculation, e.g., taking the average, weighted average, mean, median, standard deviation, liner regression, etc. of health parameters 35 calculated from the local measurements. In some embodiments, these parameters may be calculated as: Total Body Fat Percentage=0.19×Biceps Fat Percentage+0.30×Abdominal Fat Percentage+0.28× Quadriceps Fat Percentage+0.23×Scapula Fat Percentage+ 1.5×Gender−0.02×weight/height$^2$+0.05×age; Total Body Muscle Percentage=0.15×Biceps Muscle Percentage+0.25× Abdominal Muscle Percentage+0.23×Quadriceps Muscle Percentage+0.15×Scapula Muscle Percentage+1.1×Gender− 0.3×weight/height$^2$+0.03×age; and Total Body Muscle Quality=0.30×(Biceps Muscle Quality+Abdominal Muscle Quality+Quadriceps Muscle Quality+Scapula Muscle Quality)−3.2×Gender−0.2×weight/height$^2$+0.09×age.

In the equations above, 1 and 0 may be used for males and females, respectively, for the constant Gender. Height may be measured in meters, and weight may be measured in kilograms. The example above illustrates how device 10 may be used to compute health-related parameters based on the measured data. Without intending to be limiting or to suggest that "Muscle Quality" may not be further refined, "Muscle Quality" is a figure of merit for muscle capability. The higher the "Muscle Quality," the more capable is the muscle being measured. Also, without intending to be limiting or to suggest that "Muscle Fatigue" may not be further refined, "Muscle Fatigue" is a measure of a muscle's reduced capacity to exert force.

Total body fat (and/or other total body health parameters such as total muscle percentage, total MQ, etc.) may be obtained using several methods. In some embodiments, the total body fat may be obtained by combining the readings obtained from measurements of multiple individual body regions or muscles. That is, the fat percentage of multiple individual body regions and/or muscles (e.g., triceps, abs, quadriceps, etc.) is first obtained and then the data is combined to obtain the total body fat. The individual data may be combined in any manner (e.g., average, weighted average, nonlinear equations, etc.). In some embodiments, the total body fat is calculated directly using impedance values measured from individual body regions and/or muscles. For example: total body fat=b0+b1*{triceps resistance @200 kHz using configuration 1}+b2*{abs resistance @200 kHz using configuration 1}+b3*{quads resistance @200 kHz using configuration 1}+b4*{abs resistance @200 k using configuration 1}*{quads resistance @100 kHz using configuration 2}. In some embodiments, the total body fat calculated using any of the above described methods may be combined with demographic information such as gender, age, weight, or height.

Figure 12:
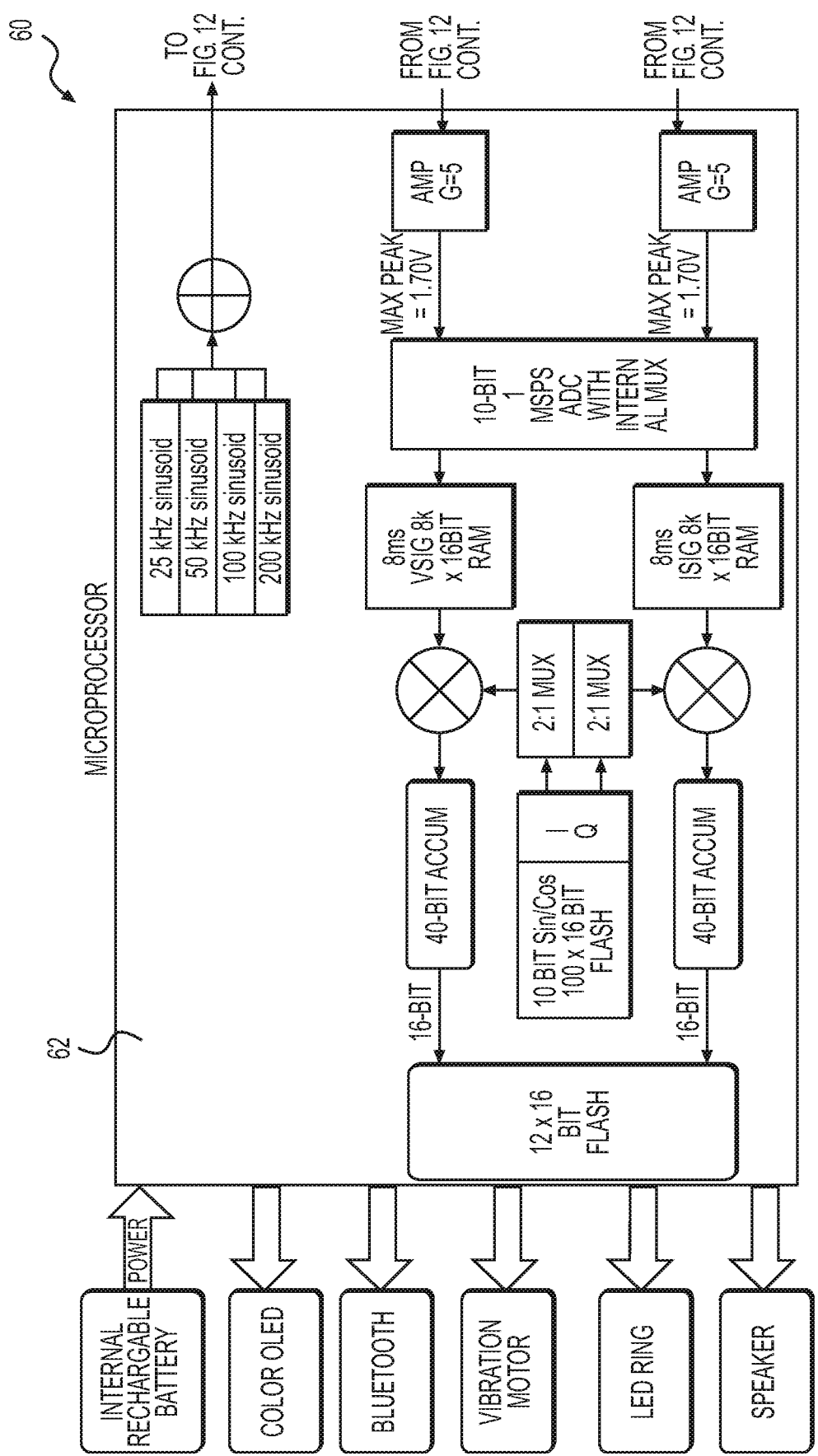
FIG. 12 is a schematic illustration of exemplary electronic circuitry of the device of FIG. 2.
Figure 12:
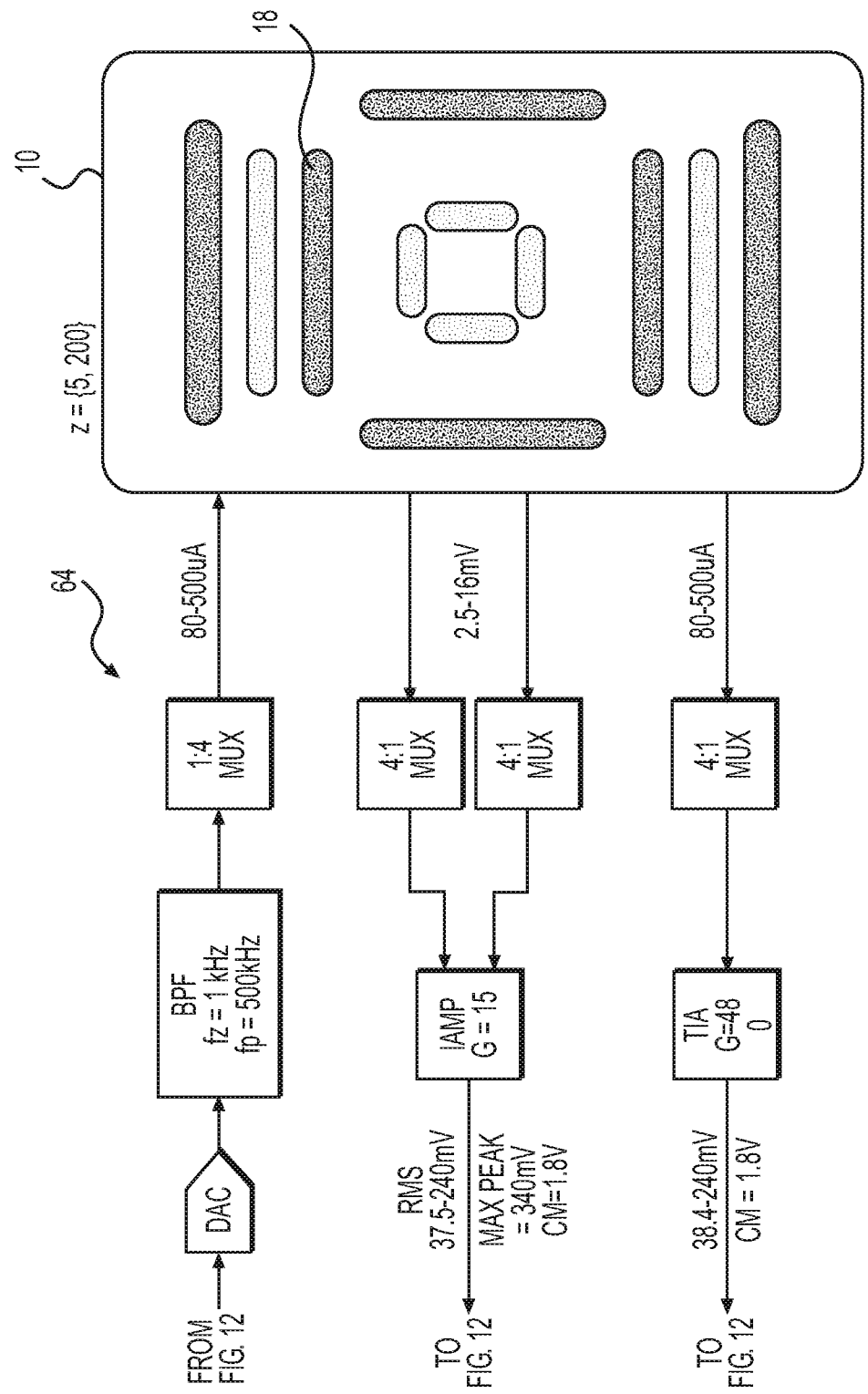

Device 10 may include electronic devices and circuitry configured to measure and compute the above-described parameters 35. FIG. 12 illustrates an exemplary circuit 60 included in device 10. Circuit 60 may include a microprocessor 62 with digital signal processing (DSP) capability, multiplexers (MUX) 64, amplifiers 66, and other electronic devices adapted to acquire the data and perform the computations to determine the parameters 35. Other exemplary circuits that may be included in device 10 are described in U.S. Pat. Nos. 8,892,198 and 9,113,808, and U.S. Provisional Patent Application Nos. 61/869,757 and 61/916,635, each of which are incorporated herein in their entirety by reference. Several exemplary embodiments of device 10 and methods of using the device are described below.

In an exemplary embodiment of circuit 60, the electrical signal applied across a pair of current elements (or electrodes 18) is digitally generated in the microprocessor 62 by adding sinusoidal signals of different amplitudes and frequencies. The digital signal is converted into an analog voltage signal using a digital-to-analog converter (DAC) and then filtered using a bandpass filter (BPF). An analog multiplexer (MUX) 64 is used to apply the signal to one of multiple electrodes 18. By applying this voltage signal to a muscle through an electrode 18, an electrical current is generated between that electrode and a second electrode connected to a transimpedance amplifier (TIA) 66 via a separate multiplexer 64. The TIA 66 accurately measures the current. The differential voltages generated on the surface of the skin are measured using an instrumentation amplifier (IAMP) 66 that is attached to two electrodes 18 via a differential multiplexer 64. The multiplexer 64 allows the IAMP 66 to be connected to multiple sets of voltage-sensing electrodes 18. The microprocessor 62 has additional amplifiers that are used to amplify the outputs of the TIA 66 and IAMP 66. Impedance calculations are then performed by the microprocessor 62 using a lock-in architecture, using methods well known to a person of ordinary skill in the art as is described in the literature. The following example illustrates how information from the user's profile and the measuring conditions may be used to measure data and compute parameters 35 by the device 10.

Profile Information: Gender: male, Weight=80 kgs, Height=1.75 m, Age=32.

Electrode Configurations: Configuration 1=current elements 20a, 20f and voltage elements 20b, 20e; Configuration 2=current elements 20a, 20f and voltage elements 20j and 20l; Configuration 3=current elements 20c, 20d and voltage elements 20j and 20l; and configuration 4=current elements 20g, 20h and voltage elements 20i and 20k.

Frequencies: F1=25 kHz; F2=50 kHz; F3=100 kHz; and F4=200 kHz

Bicep Data measured using device 10: Biceps Resistance at configuration 1 at 50 kHz=18.5 Ohms; Biceps Resistance at configuration 1 at 100 kHz=14.7 Ohms; Biceps Resistance at configuration 1 at 200 kHz=12.0 Ohms; Biceps Phase at configuration 1 at 50 kHz=24.3 degrees; Biceps Phase at configuration 2 at 50 kHz=18.6 degrees; Biceps Phase at configuration 3 at 50 kHz=14.8 degrees; Biceps Phase at configuration 4 at 50 kHz=12.1 degrees.

Using the measured data and the equations presented previously, the biceps fat percentage may be calculated as: Biceps fat percentage=0.35/ohms*(18.5 ohms+14.7 ohms+12.0 ohms)=15.8%. Data similar to bicep data described above may be measured at different locations of the body and the fat and muscle percentages at these locations may be calculated (using the equations described previously) as Abdominal Fat Percentage=29%; Quadriceps Fat Percentage=20%; Scapula Fat Percentage=22%; Abdominal Muscle Percentage=49%; Quadriceps Muscle Percentage=68%; Scapula Muscle Percentage=42%; Abdominal Muscle Quality=36; Quadriceps Muscle Quality=65; Scapula Muscle Quality=40.

These parameters are then used to calculate the physiological measures of interest as follows: Simple Biceps Fat Percentage=0.35×(18.5+14.7+12.0)=15.8%; Biceps Fat Percentage=100×tanh (0.0036×18.5+14.7+12.0)=16.1%; Biceps Muscle Percentage=100×tanh (0.025×24.3×14.8/12.1)=63.1%; Biceps Muscle Quality=100×tanh (63.1/16.1/4.5)=70.2; Modified Biceps Muscle Quality=70.2+2.1+0.1×(80/1.75$^2$)=74.9; Total Body Fat Percentage=0.19×16.1+0.30×29+0.28×20+0.23×22+1.5−0.02×(80/1.75$^2$)+0.05×32=25.0%; Total Body Muscle Percentage=0.15×63.1+0.25×49+0.23×68+0.15×42+1.1−0.3×(80/1.75$^2$)+0.03×32=38.5%; Total Body Muscle Quality=0.30×(70+36+65+40)−3.2−0.2×(80/1.75$^2$)+0.09×32=57.8.

In some embodiments, the measured data and/or the computed parameters 35 may be displayed on display 12 of device 10. In some embodiments, as explained previously, the data and/or the computed parameters 35 may be wirelessly transmitted from device 10 to the associated device 37. As also explained previously, any wireless communication technology (e.g., Bluetooth, low power Bluetooth, Wi Fi, ZigBee, etc.) may be used to transmit the information to device 37. In some embodiments, the information may be transferred to device 37 by an optical method of transmission (e.g., using visible radiation or infrared radiation), an ultrasound signal, or a wired connection.

In some embodiments, the system may include an apparatus of some type (housing, flexible substrate, etc.) to support the electrodes, a power supply and electronics to supply and measure the current, a voltage measuring system to measure the voltage resulting from the current, analytical capability to analyze the current and resulting voltage, display capability to display the calculated parameters (such as fat percentage, muscle percentage and muscle quality), and optionally data transmission capability to transmit either raw data or analyzed results to a remote data storage and/or analysis station. The apparatus may be a single integrated unit or may comprise multiple components. Without intending to be limiting, several embodiments and arrangements of the apparatus and components of the apparatus are described below.

Figure 13:
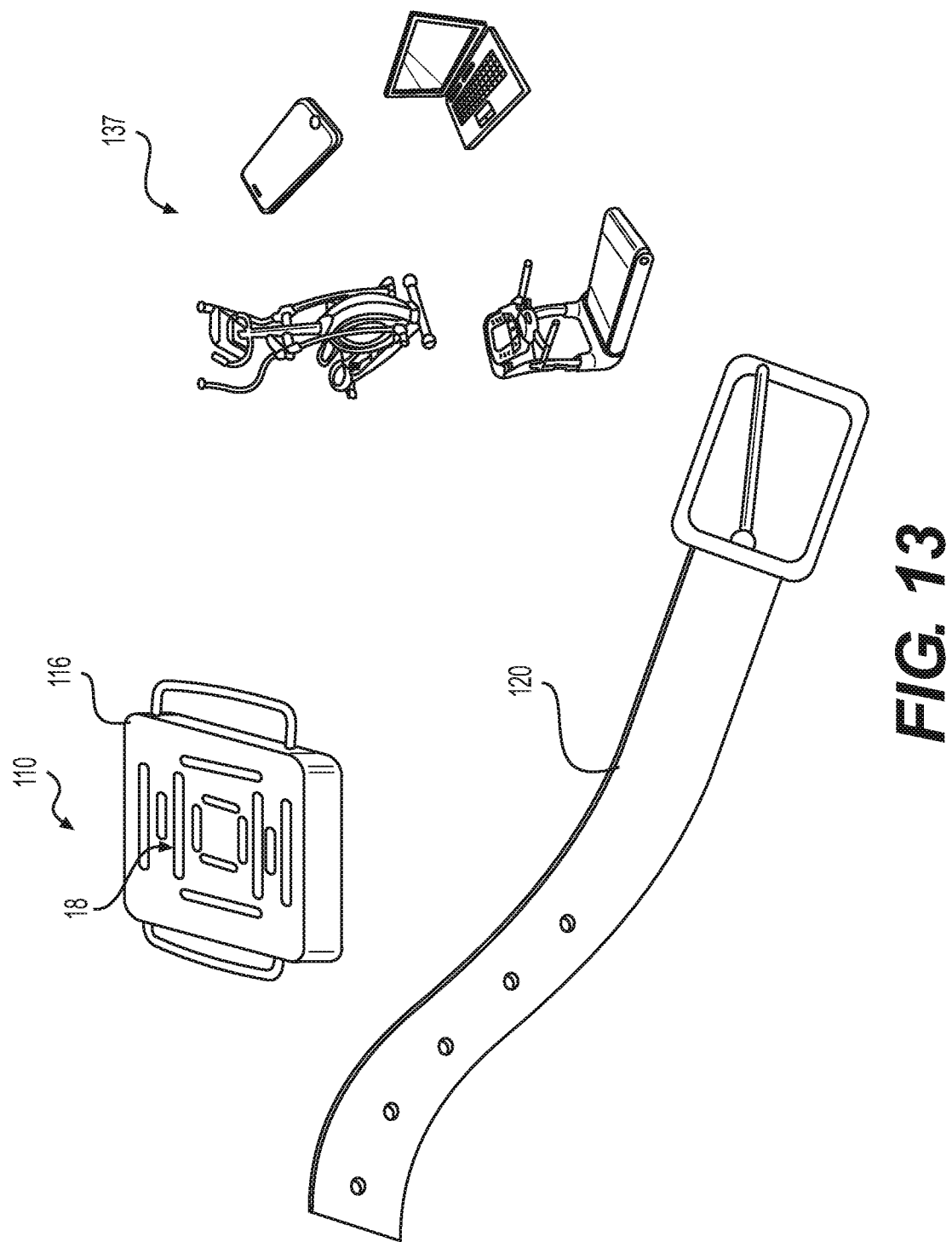
FIG. 13 illustrates another exemplary embodiment of the disclosed device.

With reference to FIG. 13, in some embodiments, electrodes 18 (which, as described previously, may include multiple current electrode pairs and voltage electrode pairs) may be incorporated into a housing 116. The housing 116 may also include (e.g., enclose) electronics to control the electrodes 18. These electronics may include circuitry to supply current to the current electrode pairs and measure the voltage across the voltage electrode pairs. In some embodiments, the electronics may also include circuits (e.g., transceiver circuits) to transmit data to an associated device 137 (e.g., a synced cellphone, computer, exercise machine, etc.) and receive instructions (e.g., to initiate measurement, select electrode pairs, configure the electronics, etc.) from the associated device 137. In some embodiments, the electronics may also include circuits configured to perform calculations on the measured data and obtain the parameters 35 from the measured data. Housing 116 may be affixed to (attached, adhered, snapped into, stitched on, using a Velcro® like attachment method, etc.) a supporting apparatus 120 (band, belt, strap, lanyard, etc.) or garment (shirt, shorts, cap, etc.) that may be worn or carried by a user. It is also contemplated that, in some embodiments, the housing 116 may be a free-standing component (i.e., not attached to a supporting apparatus 120).

In use, the user may position the supporting apparatus 120 (e.g., attach the band, wear the garment, etc.) such that the electrodes 18 are in intimate contact with the skin of the user. In embodiments, where the housing 116 is a free-standing component, the user may merely press the electrodes 18 against the skin at the desired location to make intimate contact with the skin. The associated device 137 may then initiate a measurement at the location by triggering the electronics in housing 116 to provide current to the current electrode pairs of the electrodes 18, and measure the data (e.g., voltage) across the voltage electrode pairs. In some embodiments, a button (not shown) provided on housing 116 may be pressed to initiate the measurements. The electronics in housing 116 may also and calculate the parameters 35 using the measured data (e.g., by using the previously described equations). The computed parameters 35 may then be transmitted to the associated device 137 or a remote computer system for display and/or storage. Any known wireless or wired communication technology can be used for the transmission. In some embodiments, the electronics in the housing 116 may transmit the measured raw data to the associated device 137, and the associated device 137 may perform the calculations. The housing 116 may now be repositioned to a different location (e.g., over another muscle) and the measurements repeated. In some embodiments, the housing 116 may be configured to be removed from one location and attached to a new location of the user's body to make measurements at the new location. For example, the housing 116 may be attached to the user's skin or clothing using a separable attachment mechanism (e.g., elastic band, belt like strap, gel, clip, adhesive strip, Velcro® like attachment mechanism, etc.) that may be removed from one location and repositioned to another location.

Figure 14C:
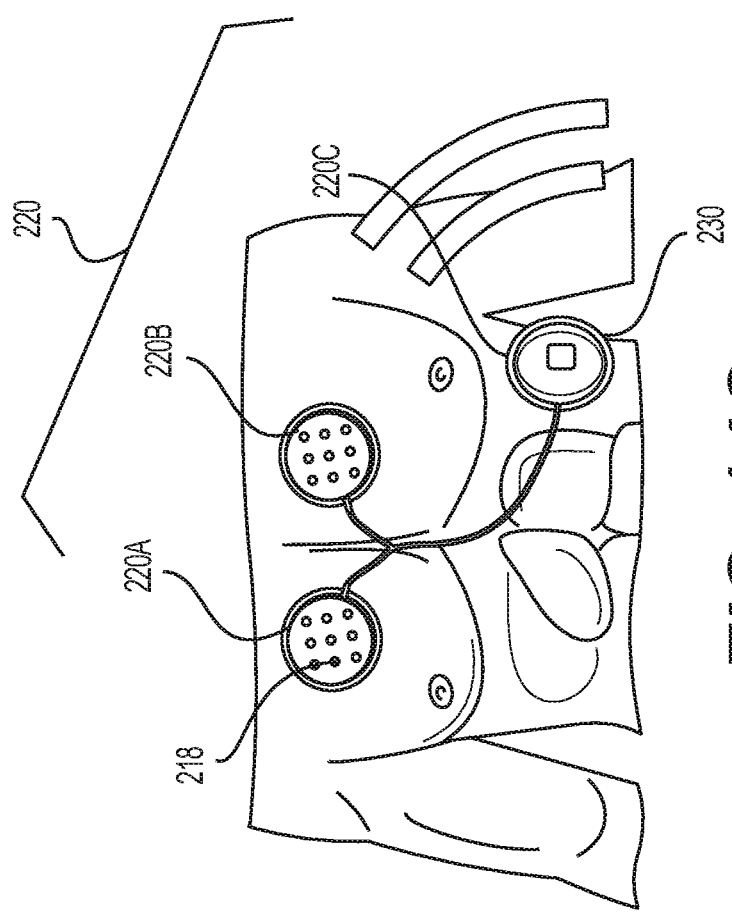
FIGS. 14A-14C illustrates another exemplary embodiment of the disclosed device.
Figure 14A:
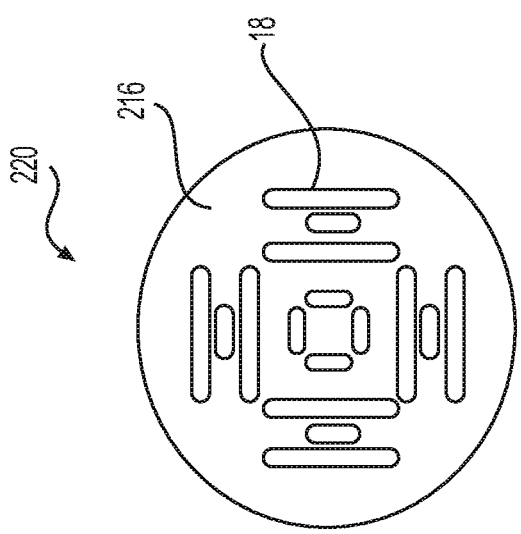
Figure 14B:
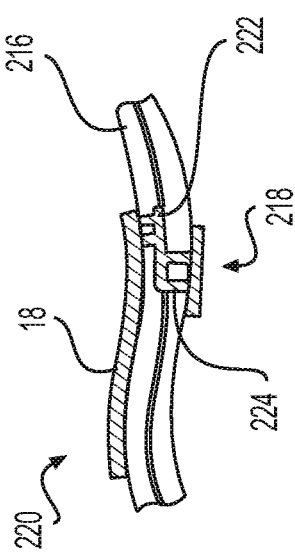

In some embodiments, as illustrated in FIGS. 14A and 14B, a device 220 may include electrodes 18 patterned on a flexible substrate 216 (e.g., a sticker-like strip). FIG. 14A illustrates a top view of the substrate 216 and FIG. 14B illustrates a cross-sectional view. In addition to the electrodes 18, the substrate 216 may include patterned circuits (e.g., conductive traces 222, plated through holes 224, and other known conductive elements) that electrically connect the electrodes 18 on one side of the substrate 216 to electrical contacts or pads 218 on the opposite side of the substrate 216. These patterned flexible substrates 216 may be made using any known material (e.g., polyimide, polyester, etc.) used for such purposes using any suitable process known in the art (e.g., lamination, deposition, masking, etching, etc.). In some embodiments, the device 220 may be self-contained in that the flexible substrate 216 includes the necessary circuitry (power supply, transceiver, etc.) to make a measurement and transmit data to a linked associated device (of any type described previously). In some embodiments, as discussed below, a separate module that includes a power supply and the required electronics may couple with the device 220 to make measurements.

FIG. 14C illustrates an exemplary method of using a device 220 of the type described with reference to FIGS. 14A and 14B. The device 220 may be attached to the user's skin at the desired location such that the electrodes 18 are in contact with the skin. In some embodiments, multiple devices 220 may be attached at several desired locations (e.g., over multiple muscles) on the user. The device 220 may be attached to the skin by any method (e.g., using a gel, glue, tape, etc.). In some embodiments, similar to the structure of a band-aid, the substrate 216 may include an adhesive layer over the electrodes 18 that is covered using a protective strip. To attach device 220 to the skin, the user may peel off the protective strip and attach the substrate 216 at the desired location with the electrodes 18 in contact with the skin. In some embodiments, a gel layer may also be provided under the protective strip to enhance electrical contact between the electrodes and the user's skin.

To make measurements using a self-contained device 220, the associated device may wirelessly initiate a measurement by sending a signal to the one or more devices 220 attached to the user. In response, the device 220 may make a measurement and send the measured data to the associated device. The associated device may calculate the parameters 35 using the data and present results on its display. It is also contemplated that, in some embodiments, the device 220 may perform some or all of the calculations and transmit the results to the associated device. In some embodiments, as illustrated in FIG. 14C, a separate module 230 that includes a power supply (battery) and the electronics (needed to make a measurement), may be electrically coupled to the device 220 to make a measurement.

In the illustration of FIG. 14C, three flexible devices 220A, 220B, and 220C are shown attached to the user to illustrate different exemplary methods of electrically coupling the module 230 to the devices 220. In general, the module 230 may be electrically coupled to a device 220 in any manner. In some embodiments, the module 230 may include electrical contacts that align and mate with the pads 218 on the flexible substrate 216 of the device 220. In some such embodiments, the module 230 may be attached to a device 220 such that the contacts on the module 230 mate with the corresponding contacts on the device 220 (see device 220C of FIG. 14C). The module 230 may be attached to the device 220C in any manner. In some embodiments, the top surface of the device 220 may also include an adhesive layer (similar to the adhesive layer over the electrodes 18) covered by a peelable strip of material, and the module 230 may be attached to the device 230C using this adhesive layer. However, this attachment method is only exemplary and other attachment methods (such as, a clip, band, or a Velcro® like attachment mechanism) may be used to attach the module 230 to the device 230C. Upon initiation of a measurement (using the module 230 or an associated device linked to the module 230), the module 230 may supply power to the electrodes 18, acquire data, and compute results. The results may then be transmitted to the associated device for display. In some embodiments, the raw data may be transmitted to the associated device for calculations and display of results.

In some embodiments, as illustrated using devices 220A and 220B of FIG. 14C, the module 230 may be connected to the devices 220 using wires, and the module 230 may trigger and make a measurement as discussed above. It is also contemplated that, in some embodiments, the module 230 may be wirelessly coupled to the devices 220. In some embodiments, as illustrated in FIG. 14C, the module 230 may be directly mounted on one device 220 attached to the user (e.g., device 220C), and connected to the other devices (e.g., device 220A, 220B) using wires. In some embodiments, the module 230 may be carried by the user (e.g., hooked to a belt, in a pocket, etc.) and coupled to the one or more devices 220 using wires. The module 230 may make take measurements of all the devices 220 attached to the user simultaneously (i.e., devices 220A, 220B, and 220C measured at the same time) or sequentially (i.e., devices 220A first, 220B second, and 220C third, etc.)

Figure 15:
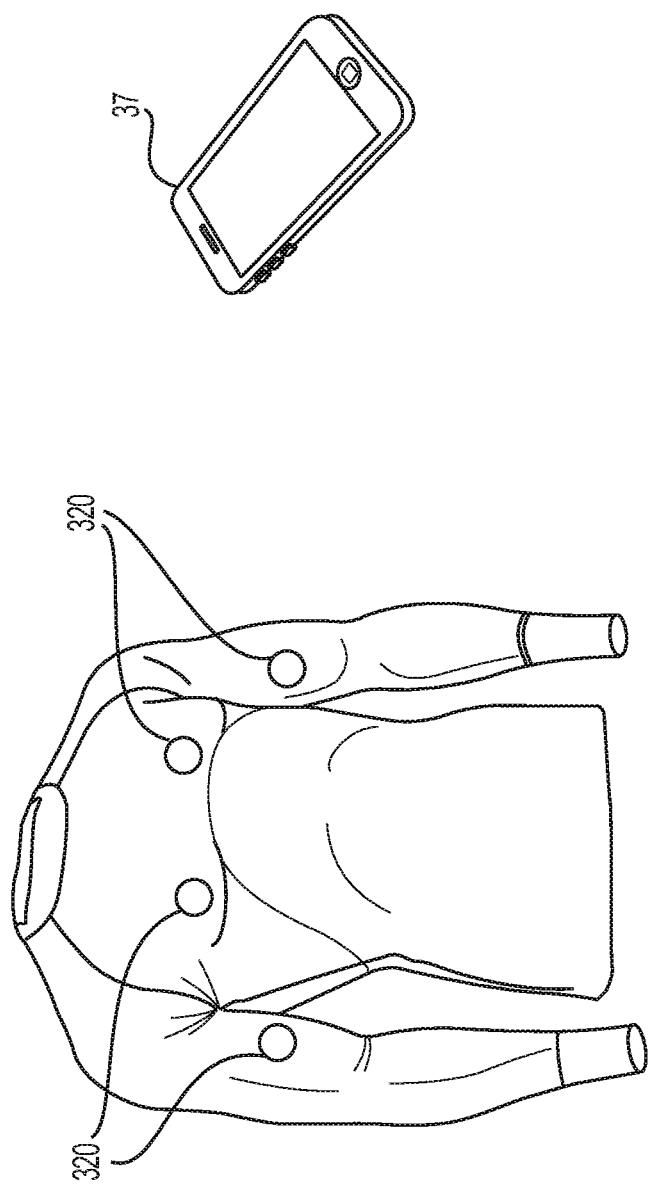
FIG. 15 illustrates another exemplary embodiment of the disclosed device.

FIG. 15 illustrates another embodiment of the disclosed device. In this embodiment, one or more devices 320 (similar to the devices discussed above) may be incorporated into a garment worn by the user. In device 320, an electrode array (similar to those discussed previously) and associated circuitry may be stitched or weaved into the garment at desired locations. In some embodiments, the electrodes may be woven into the fabric on a garment such as a shirt, shorts, pants, socks, etc. and connected to electronics that perform the measurements. The electrodes also may be configured for placement into prefabricated "pockets" in the garment. These locations may correspond to the location of the desired muscles groups in the body. When worn by the user, the electrodes of the device 320 may snugly contact the skin of the user. Generally, the garment may include any tight fitting clothing. In some embodiments, a module (similar to module 230 of FIG. 14C) may electrically couple with the one or more devices 320 in the garment to control the devices 320, make a measurement, and transfer results to an associated device 37. The module may electrically couple with and make a measurement using any of the methods described with reference to the embodiment of FIGS. 14A-14C. In some embodiments, the module may be eliminated and the associated device 37 may be used to control the devices 320.

Figure 16A:
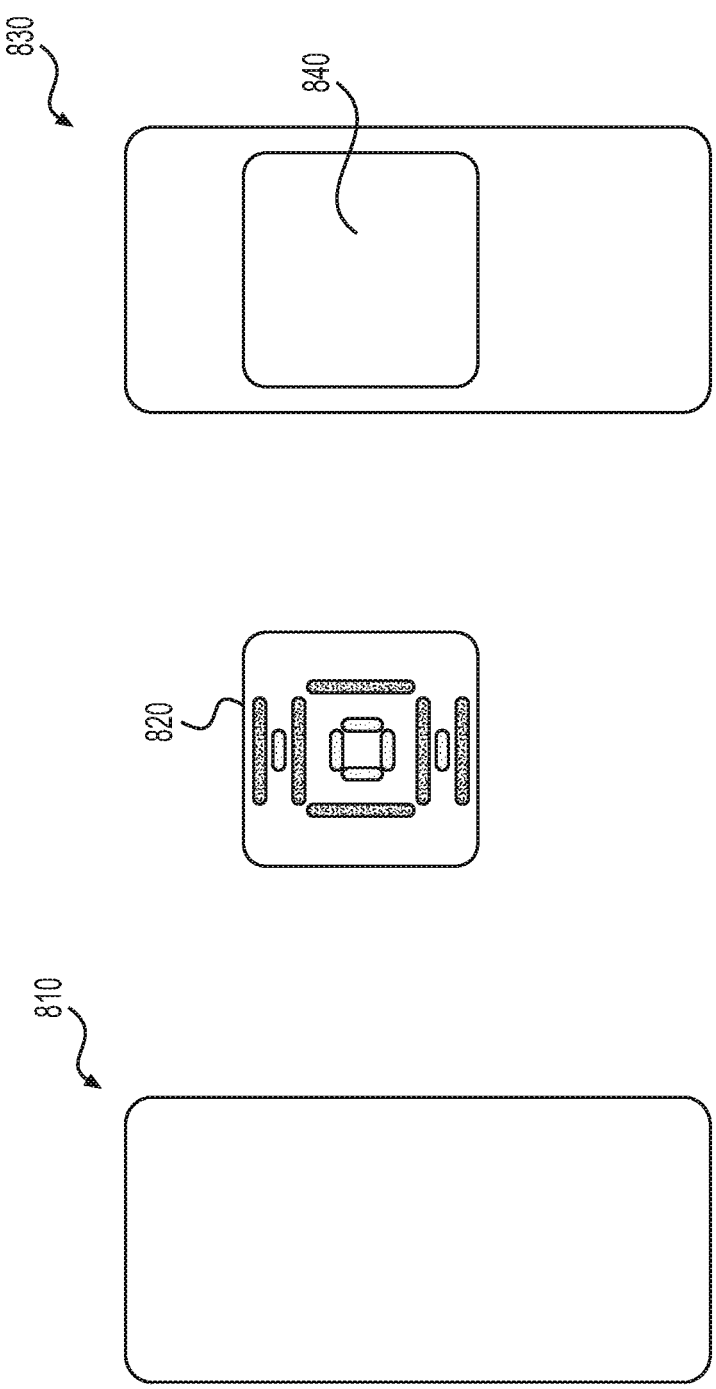
FIGS. 16A-16B illustrates other exemplary embodiments of the disclosed device.
Figure 16B:
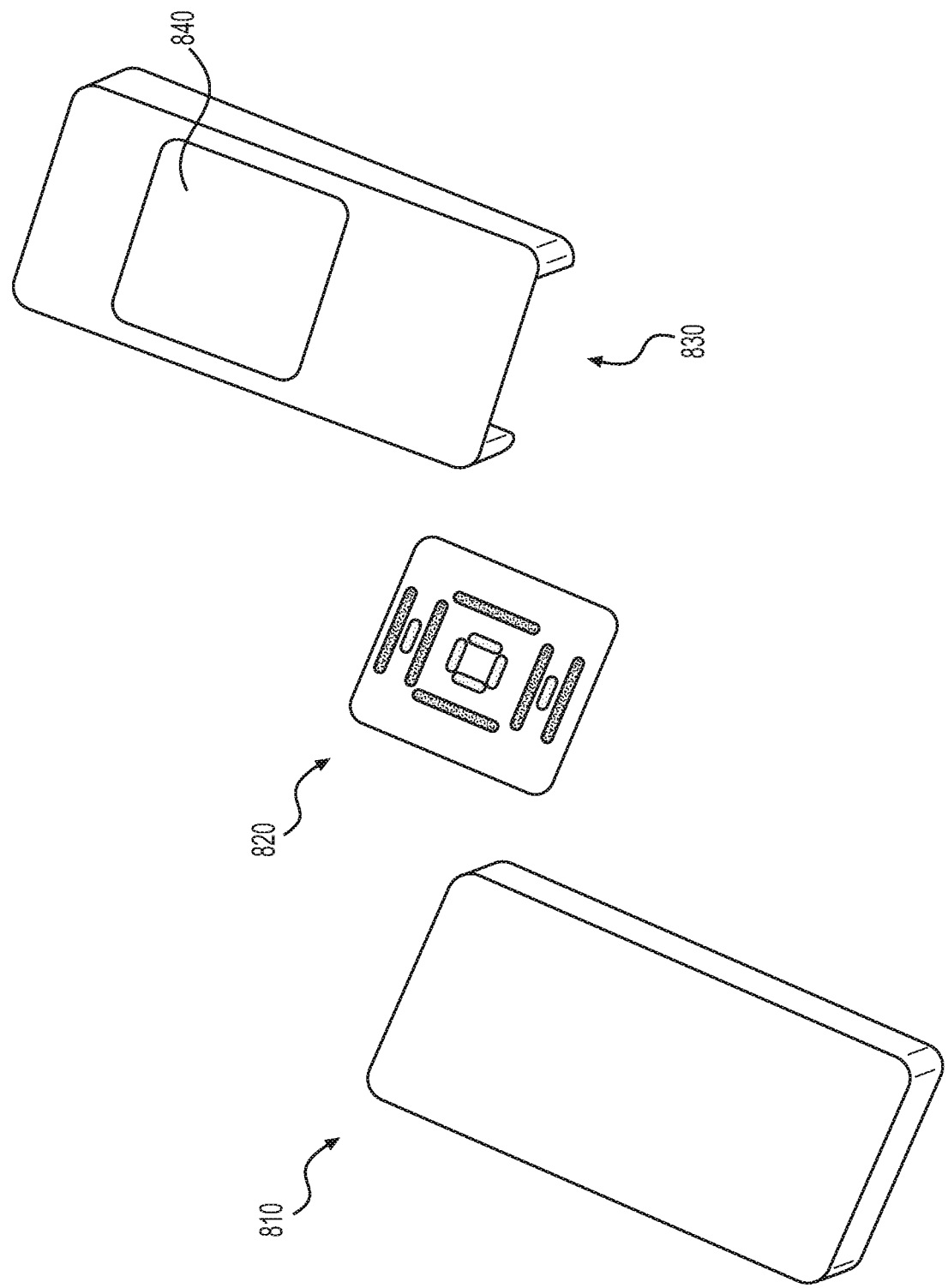

In some embodiments, as illustrated in FIGS. 16A and 16B, the electrodes 18 may be incorporated into the body of a portable music player (e.g., Apple IPod®) or a cellphone 810 (e.g., Apple iPhone®, Samsung Galaxy®, etc.), and an application may be used to control the measurement of the data and calculate parameters 35 based on the measured data. For example, the cellphone 810 may be powered by its internal power supply (such as a battery), or a separate power supply. A software application (or app) on the cellphone may be used together with the computational capability of the cellphone to control the supply and measurement of current. In some embodiments, hardware-based or software-based voltage measuring capability may be built into the cellphone 810 and the application may be used to analyze the measured voltage and current, and perform calculations. This application can either be the same application used to control the supply of current or a different application. The display of the cellphone 810 may be used to display the measured data and the computed parameters 35. In some embodiments, the data transmission capability of the cellphone 810 may be used to transmit the measured data and/or analysis results to a remote station for data storage and/or analysis. In some embodiments, the cellphone's mobile communication network may be used for this transmission and in other embodiments, any of the previously described wireless communication mechanisms may be used.

Several other modifications of the above described embodiment are also contemplated. For instance, in some embodiments, the electrodes 18 may be incorporated into a case 830 which is used to hold and/or protect a cellphone 810 or a portable music player. The cellphone 810 may be configured to fit into (slip, slide, fastened, etc.) the case 830. In some embodiments, as the cellphone 810 is positioned in the case 830, electrical contacts on the case (connected to the electrodes 18) and corresponding contacts on the cellphone 810 make contact to establish an electric connection. It is also contemplated that, in some embodiments, information (data, instructions, signals, etc.) may be transferred between the cellphone 810 and the case 830 wirelessly (e.g., using known communication technology). The power supply that provides power to the electrodes 18 may be a separate power supply in the case 830 or may be the power supply of the cellphone 810. Computational capability may be built into the case 830 (or may be incorporated in a cellphone application) to control the current delivery. Voltage and current measuring capability may be built into the case 830 and/or the cellphone 810.

In some embodiments, the user may activate an electrical connection between the case 830 and the cellphone 810 (for instance, by inserting a wire connecting them, by activating a switch, etc.) when desired. This electrical connection between the case 830 and the cellphone 810 may then be used to transfer electrical power, data, information, or signals between the two. An application on the cellphone 810 may be used to analyze current and voltage and compute the parameters 35. The display of the cellphone 810 may be used to display the data or a separate display (an external display, etc.) may be used. The mobile communication capability of the cellphone 810, or any wireless communication capability may be used to transmit the data and parameters 35 to a remote station for data storage and analysis.

In another embodiment, the electrodes 18 may be housed in a module 820 separate from the cellphone 810 and the case 830 as shown in FIG. 16B. The module 820 may be positioned such that its electrodes are kept in contact with skin. In some embodiments, the module 820 may be attached to the user using a strap or an elastic band. However, any attachment mechanism may be used to attach the module 820 to the user. In some embodiments, the module 820 may transmit the measured data and/or analysis results to the phone 830. In some embodiments, wires may connect the module 820 to the phone 810. In some embodiments, the module 820 may include memory to store the measured data. After measurements are taken at one or more locations of the user's body, the stored data may be transferred from the module 820 to the phone 810. Data may be transferred wirelessly or through a wired connection. In some embodiments, the user may establish a connection between the phone 810 and the module 820 (e.g., by connecting a wire between them). The wired connection may be removable at both ends or may be permanently attached to the electrode apparatus. Power may be provided to the module 820 and to the electrodes 18 from the phone 810 using this connection or using a separate power supply in the module 820. Similar to the embodiments discussed above, the cellphone 810 may perform the necessary computations to determine the parameters 35 and display the parameters 35 on the cellphone display and/or transfer them to a remote location using the wireless capability of the cellphone 810. Although data is described as being transferred to a phone 810, in general, data can be transferred to ant associated device described previously.

In some embodiments, data may be transferred between the module 820 and the phone 810 (or another associated device) by inserting the module 820 (or a connector attached to the module 820) to a cavity or a port (USB port, Lightning connector port, etc.) in the phone 810. In some embodiments, data may be transferred from the module 820 to the case 830 using any of the methods described above. In some embodiments, a separate power supply may be provided in the module 820. In some embodiments, the phone 810 or the case 830 may provide power to the module 820 and computational capability may be provided by a cellphone app. In some embodiments, current and voltage measuring capability may be built into the cellphone case 830 and data may be transmitted from the module 820 to the cellphone 810. A cellphone app may be used to analyze current and voltage and perform calculations, and the display of the cellphone 810 may be used to display the data. In some embodiments, data and/or results may be transmitted from the phone 810 to a remote computer for data storage and/or analysis. The mobile communication network or wireless capability of the cellphone 810 may be used for the transmission. In some embodiments, the module 820 may directly transfer the measured data (wirelessly or through a wired connection) to a remote station (such as, computer system 40 of FIG. 1) where it is stored and/or analyzed.

Throughout this disclosure, the terms, "phone," "cellphone," and "smartphone" are used interchangeably. Examples of smartphones include iPhones, Android phones and other similar phones. A smartphone based device as described with reference to FIGS. 16A and 16B is used to make the measurements described below. This device includes at least three parts—the smartphone 810; module 820 with the electrodes 18 in contact with the tissue; and a case 830 or holder which holds the module 820 and snaps or fastens securely onto the smartphone 810. There is a hole 840 in the case 830 which allows the electrodes 18 on the module 820 to come into direct contact with the tissue. The module 820 is located between the smartphone 810 and the case 830 and is held securely in place by the case. There may be locating pins or another similar mechanism on the module 820 and the case 830 to ensure that the electrodes 18 are properly oriented (e.g., along the axis of the smartphone 810 or in some other desired orientation).

This arrangement allows a single design of module 820 to be used with a number of designs of smartphones 810. The module 820 can communicate with the smartphone 810 by wire, wireless or direct plug in communication. The module 820 can be powered by the smartphone 810 or internally powered. In this arrangement, by using a unique case 830 for each smartphone design, a single (or a small number) of module designs may enable the use of the module 820 with essentially any design of smartphone or corresponding case. We contemplate the use of this technology with iPhones, Android devices, and other such phones. It is contemplated that a case 830 can be designed for new designs of smartphone to be used with the module 820.

An exemplary application of the disclosed system and method will now be described. The determination of the effect of vigorous exercise and recovery on EIM of the bicep of a male human user (of age 35, height 5'9", and weight 182 lbs) using device 10 of FIG. 2 is described. The electrodes 18 (FIG. 10A) of device 10 was applied to the skin of the subject as shown in FIG. 11. Nine baseline pre-exercise EIM measurements were taken over the course of 80 minutes (one every ten minutes) using configuration 1 described previously, and Muscle Quality (MQ) computed using the equation, MQ=3×Phase at 50 kHz+25. For example, if for a particular measurement, the phase at 50 kHz is 30, the MQ would be (3×30)+25=90+25=115. The average MQ for the baseline measurements was 106.4 with a standard deviation of 0.53.

Four minutes after the final baseline measurement, the user exercised the right biceps muscle by performing biceps curls 10 times using a 20 pound dumbbell (this took approximately one minute). In a bicep curl, the arm is extended straight and approximately horizontal holding the weight. The muscle is then contracted so that the elbow is bent approximately 90 degrees, with the upper arm (nearest the shoulder) remaining approximately horizontal and the lower arm including the hand holding the weight is approximately vertical. A measurement was performed immediately following the final repetition of exercise and the value of MQ was computed to be 116. The user rested for one minute and then performed an additional 10 repetitions of biceps curls. Another measurement was made immediately after resulting in an MQ value of 127. The subject rested for an additional minute and a third set of 10 repetitions of bicep curls were performed followed by another measurement yielding an MQ value of 117. Two minutes later, another measurement was made showing an MQ value of 107. Measurements were then conducted every 2 minutes for the next 20 minutes (a total of 10 measurements at 2 minute intervals), then every 5 minutes for the next 50 minutes (a total of 10 measurements at 5 minute intervals), and then once every 10 minutes. In some cases, multiple measurements were made at the same time. A total of 85 measurements were conducted and MQ computed using device 10.

Figure 17:
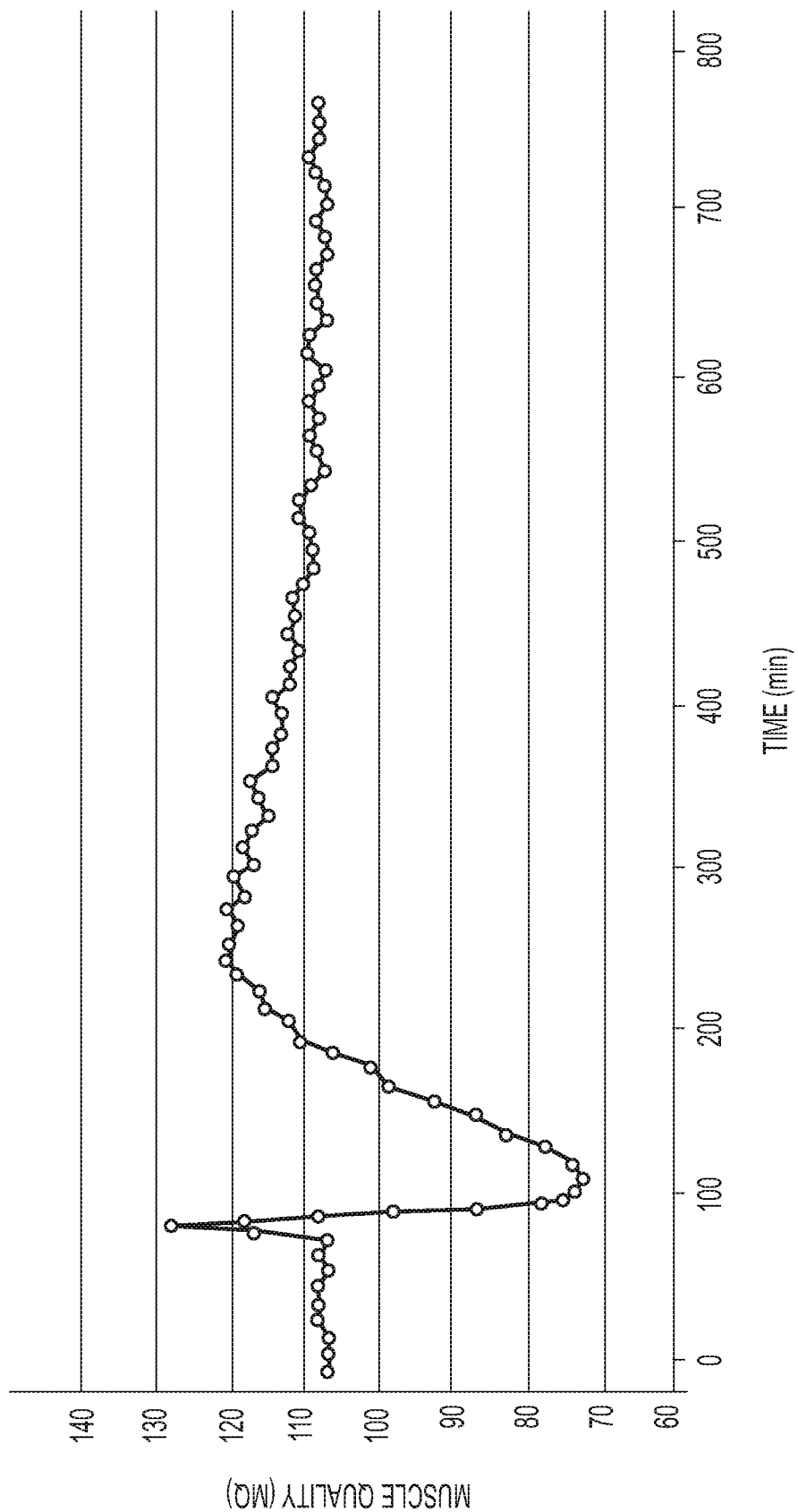
FIG. 17 is a plot of exemplary results obtained by the device as a function of time.

FIG. 17 is a graph showing the computed MQ results and FIG. 18 is a table of these results. As shown in FIG. 17, the subject's MQ was stable during the baseline measurements, then spiked sharply during the sets of biceps curls, and then dropped significantly below baseline reaching a minimum value of 72 approximately 20 minutes after the final set. The MQ then rose slowly above the baseline value and then slowly came back down to approximately the same value seen at baseline.

In other embodiments, impedance values such as resistance, phase, or reactance at one or more frequencies and one or more configurations can be used to calculate muscle fatigue. For example, the resistance at 50 kHz for configuration 1 can be monitored in a similar fashion as described above in place of MQ.

Using the method described above, or by following a similar method in which the fatigue and/or recovery of an exercising muscle is quantitatively measured, an exercise program may be designed by a physical therapist, personal trainer or other appropriately skilled person. The information from the measurements may be used in designing the exercise program. Over time, the user carries out the exercise program and, at appropriate times and intervals, the fatigue and/or recovery is measured. For example, the measurements might be once per week, once every two weeks or at other appropriate intervals. The change in fatigue and/or recovery measurements may be noted and the exercise program may be continued or modified as appropriate to enhance muscle improvement, muscle capability retention or minimize muscle deterioration.

In a further example, measurements and calculation of fat percentage and MQ were obtained. Measurements of EIM were made on a number of individuals and body fat percentages and MQ were calculated for each person. The equations used to calculate fat percentages and MQ were the following: Fat Percentage=R50C1−7; MQ=M(k1*P100-C1^2+k2*P50C3^2+(k3/R25C1)^2+(k4/R50C1)^2+(k5/R100C1)^2+(k6/R200C1)^2)^0.5+N. Where P100C1, for example, means phase at 100 kHz using configuration 1, P50C3 means phase at 50 kHz using configuration 3, R25C1 means resistance at 25 kHz using configuration 1, R50C1 means resistance at 50 kHz using configuration 1, R100C1 means resistance at 100 kHz using configuration 1, R200C1 means resistance at 200 kHz using configuration 1. In the equation for MQ, the following constants and parameters are used: M=1.1, k1=3.6, k2=3.4, k3=480, k4=720, k5=240, k6=240. And, the following values are used for N depending upon specific muscle or body part. Biceps N: 30, Triceps N: 35, Shoulders N: 30, Forearms N: 30, Chest N: 30, Abs N: 55, Thighs N: 45, Hamstrings N: 30, Calves N: 30, Gluteus Maximus N: 30, Lower Back N: 30, and Upper Back N: 30. These equations may be used in conjunction or alternatively those discussed elsewhere in the present disclosure.

As would be recognized by a person of ordinary skill in the art, electrode separation is the distance between two electrodes of electrodes 18, for example, electrode 20a and electrode 20e in FIG. 10A. Set of electrode separations refers to the separation of the electrodes in a configuration. For example, for configuration 1, the set of electrode separations would be the separation between electrode 20a and electrode 20e (the current electrodes) and the separation between electrode 20b and electrode 20f (the voltage electrodes). A plurality of sets of electrode separations, refers to two or more sets of electrode separations. For example, this could be the set of electrode separations of configuration 1 and the set of electrode separations of configuration 3. In the equation for MQ listed above, the calculations use information taken using a plurality of sets of electrode separations, namely configuration 1 and configuration 3.

Test protocol refers to the conditions involved in making one or more measurements including device position(s), test frequencies, electrode arrangement, electrode separations, configurations used and other test parameters. Device position refers to the location in which the device is positioned on the tissue with the electrodes in contact with the tissue. Single device position indicates that the device is positioned on the tissue and not moved. Measurements made during a single device position refers to the measurements made during a single device position during which the device and electrodes are not moved or realigned. As explained previously, these measurements may involve measurements from multiple electrodes or multiple configurations.

FIG. 19 presents the data from measurements discussed above. In the data of FIG. 19, values are given for total body MQ and total body fat percentage. The formulae used to calculate these values are: Total MQ=average of MQ of biceps, triceps, quadriceps and abdominals; Total body fat percentage=average of body fat percentage of biceps, triceps, quadriceps, and abdominals. However, as discussed previously, measured data of individual body regions may be combined in any manner (e.g., average, weighted average, nonlinear equations, etc.) to get the total body health parameters.

In another example, gender specific measurements of MQ were obtained. These results are presented in FIG. 20. EIM measurements were made using the methods discussed above and calculated using the equation: MQ=M(k1*P100C1^2+k2*P50C2^2+(k3/R25C1)^2+(k4/R50C1)^2+(k5/R100C1)^2+(k6/R200C1)^2)^0.5+N; M=1.1; Gender specific values were used for N in the equation above.

Although exemplary embodiments of devices 10 and 37 and methods of using these devices are described herein, a person of ordinary skill in the art would recognize that numerous variations of these devices and methods are possible. For example, in some embodiments, the device 10 and/or 37 may have the capability for audio output or for audio input. Audio output may include, for example, audio output of data, training information, etc., audio repetition of textually displayed information, or audio information synched with displayed video, etc. Audio input may include various commands used to control the device 10 and/or 37. That is, device 10 and/or 37 may be activated and/or controlled by audio commands. In some embodiments, device 10 and/or 37 may turn itself off to save power after a predetermined period of inactivity. This predetermined time may be a preprogrammed value that may be changed by the user. In some embodiments, whenever a measurement is made or a control signal is entered into device 10 and/or 37, a timer for automatically turning off may be reset. In some methods of using the device 10, the electrodes 18 may be moistened (i.e., pre-moistened) before being placed in contact with skin to improve contact of the electrodes 18 with the skin. In some embodiments, this pre-moistening may not be needed since sufficient electrical contact may be achieved without pre-moistening. Pre-moistening may be achieved by a spray, cloth, a wipe, or any other method which provides sufficient moisture.

While principles of the present disclosure are described herein with reference to illustrative embodiments for particular applications, it should be understood that the disclosure is not limited thereto. Those having ordinary skill in the art and access to the teachings provided herein will recognize additional modifications, applications, embodiments, and substitution of equivalents all fall within the scope of the embodiments described herein. Accordingly, the invention is not to be considered as limited by the foregoing description.

We claim:

1. A method for quantitatively measuring fatigue and recovery of a muscle or muscle group comprising:
   a. placing a plurality of electrodes on skin above the muscle or muscle group or on the muscle or muscle group,
   b. using a first device for measuring at least one bioimpedance-related property of tissue, comprising: a housing; a power supply in the housing; the plurality of electrodes, the plurality of electrodes including a first pair of current electrodes and a corresponding first pair of voltage electrodes positioned between the first pair of current electrodes; and electronic circuitry in the housing, the electronic circuitry being configured to (1) obtain data by performing first EIM measurements on the muscle or muscle group prior to beginning exercising of the muscle or muscle group to establish a baseline value by directing current into tissue through the first pair of current electrodes and measuring a voltage across the corresponding first pair of voltage electrodes and (2) calculate a first value for the at least one bioimpedance-related property of the tissue selected from a group consisting of resistance, reactance, phase, and impedance based on the obtained data c. while the muscle or muscle group is exercising, using the device to perform a second at least one EIM measurement on the muscle or muscle group and calculating a second value of the at least one bioimpedance-related property, in which the second calculated value of the at least one bioimpedance-related property is less than the established baseline value, d. continuing to perform the second at least one EIM measurement until the second calculated value of the at least one bioimpedance-related property is about the same as the calculated baseline value, e. determining a time after exercise when a third value of the at least one bioimpedance-related property is about the same as the calculated baseline value, in which a time for recovery is 210 minutes or less.

2. The method of claim 1 in which the at least one bioimpedance-related property comprises resistance.

3. The method of claim 1 in which the at least one bioimpedance-related property comprises reactance.

4. The method of claim 1 in which the at least one bioimpedance-related property comprises phase.

5. The method of claim 1 in which the at least one bioimpedance-related property comprises impedance.

6. The method of claim 1 in which one or more of the first EIM measurements and the second at least one EIM measurement, are used to measure quantitatively at least one of fatigue and recovery of the exercising muscle or muscle group.

7. The method of claim 6 in which a measure of the at least one of fatigue and recovery of the exercising muscle or muscle group is used to design an exercise program.

8. The method of claim 7 further comprising making additional EIM measurements at subsequent times and continuing or modifying the exercise program to enhance muscle improvement, enhance muscle capability retention or minimize muscle deterioration.

9. The method of claim 1 in which one or more of the first EIM measurements and the second at least one EIM measurement are used to calculate a Muscle Quality (MQ).

10. The method of claim 1 further comprising an associated device, wherein the electronic circuitry of the first device is further configured to wirelessly transmit at least one of the first and second calculated value of the bioimpedance-related property to the associated device adapted to display at least one of the calculated first value for the at least one bioimpedance-related property or the calculated second value of the at least one bioimpedance-related property, the associated device including one of a cellular phone, a computer, a tablet, and an exercise machine.

11. A method for quantitatively measuring a fatigue or recovery of a muscle or muscle group comprising:

a. placing a plurality of electrodes on the muscle or muscle group or on skin above the muscle or muscle group, b. using a first device for measuring bioimpedance-related properties of tissue, comprising: a housing; a power supply in the housing; the plurality of electrodes, the plurality of electrodes including a first pair of current electrodes and a corresponding first pair of voltage electrodes positioned between the first pair of current electrodes; and electronic circuitry in the housing, the electronic circuitry being configured to (1) obtain data by directing current into tissue through the first pair of current electrodes and measuring a voltage across the corresponding first pair of voltage electrodes wherein the data comprises at least one value, and (2) calculate a first value for at least one bioimpedance-related property of the tissue selected from a group consisting of resistance, reactance, phase and impedance based on the obtained data, to perform first EIM measurements on the muscle or muscle group while the muscle or muscle group is exercising, c. using the device to perform second EIM measurements on the muscle or muscle group while the muscle or muscle group continues to exercise, d. using the first and second EIM measurements to measure the fatigue or recovery quantitatively of the exercising muscle or muscle group, in which the first and second EIM measurements are used to measure the recovery of the exercising muscle or muscle group and in which a time for recovery is 210 minutes or less, further comprising performing third EIM measurements prior to beginning the exercising of the muscle or muscle group to establish a baseline value, further comprising performing fourth EIM measurements after the exercising of the muscle or muscle group has stopped, further comprising continuing to perform additional EIM measurements until a value resulting from the additional EIM measurements is about the baseline value.

12. The method of claim 11 in which the at least one bioimpedance-related property comprises resistance.

13. The method of claim 11 in which the at least one bioimpedance-related property comprises reactance.

14. The method of claim 11 in which the at least one bioimpedance-related property comprises phase.

15. The method of claim 11 in which the at least one bioimpedance-related property comprises impedance.

16. The method of claim 11 in which a measure of at least one of the fatigue and recovery of the exercising muscle is used to design an exercise program.

17. The method of claim 16 further comprising making further additional measurements at subsequent times and continuing or modifying the exercise program to enhance muscle improvement, enhance muscle capability retention or minimize muscle deterioration.

18. The method of claim 11 in which one or more of the first EIM measurements, the second EIM measurements, the third EIM measurements, and the fourth EIM measurements are used to calculate a Muscle Quality (MQ).

19. The method of claim 11 further comprising an associated device, wherein the electronic circuitry of the first device is further configured to wirelessly transmit the calculated first value of the bioimpedance-related property to the associated device adapted to display the calculated first value of the bioimpedance-related property, the associated device including one of a cellular phone, a computer, a tablet, and an exercise machine.

20. The method of claim 11 in which each of the first, second, third, fourth, and additional EIM measurements comprise at least one frequency selected from a group consisting of about 25 kHz, about 50 kHz, about 100 kHz and about 200 kHz.

* * * * *